(12) United States Patent
Coppola et al.

(10) Patent No.: US 7,291,635 B2
(45) Date of Patent: Nov. 6, 2007

(54) 5-SUBSTITUTED 1,1-DIOXO-1,2,5,-THIADIAZOLIDIN-3-ONE DERIVATIVES

(75) Inventors: Gary Mark Coppola, Budd Lake, NJ (US); John William Davies, Winchester, MA (US); Charles Francis Jewell, Jr., Sudbury, MA (US); Yu-Chin Li, Edison, NJ (US); James Richard Wareing, Stow, MA (US); Donald Mark Sperbeck, Berkeley Heights, NJ (US); Travis Mathew Stams, Stow, MA (US); Sidney Wolf Topiol, Fair Lawn, NJ (US); Isidoros Vlattas, Summit, NJ (US)

(73) Assignee: Novartis AG, Basel (CH)

( * ) Notice: Subject to any disclaimer, the term of this patent is extended or adjusted under 35 U.S.C. 154(b) by 71 days.

(21) Appl. No.: 10/510,026

(22) PCT Filed: Apr. 2, 2003

(86) PCT No.: PCT/EP03/03466

§ 371 (c)(1),
(2), (4) Date: Dec. 16, 2004

(87) PCT Pub. No.: WO03/082841

PCT Pub. Date: Oct. 9, 2003

(65) Prior Publication Data

US 2005/0090502 A1    Apr. 28, 2005

Related U.S. Application Data

(60) Provisional application No. 60/369,930, filed on Apr. 3, 2002, provisional application No. 60/369,779, filed on Apr. 3, 2002.

(51) Int. Cl.
*A61K 31/433* (2006.01)
*C07D 285/10* (2006.01)
(52) U.S. Cl. .......................... 514/362; 548/135
(58) Field of Classification Search ................ 548/135; 514/362
See application file for complete search history.

(56) References Cited

U.S. PATENT DOCUMENTS

| | | | | |
|---|---|---|---|---|
| 5,162,340 | A | 11/1992 | Chakravarty et al. | 514/309 |
| 5,281,614 | A | 1/1994 | Ashton et al. | 514/359 |
| 5,412,097 | A | 5/1995 | Chakravarty et al. | 546/118 |
| 5,958,957 | A | 9/1999 | Anderson et al. | 514/364 |
| 5,972,978 | A | 10/1999 | Anderson et al. | 514/361 |
| 6,063,800 | A | 5/2000 | Anderson et al. | 514/369 |
| 6,080,770 | A | 6/2000 | Anderson et al. | 514/359 |

FOREIGN PATENT DOCUMENTS

EP     501568 A1 *    9/1992

| EP | 0 512 870 | 11/1992 |
|---|---|---|
| WO | WO92/20687 | 11/1992 |
| WO | WO97/40017 | 10/1997 |
| WO | WO 01/19831 | 3/2001 |

OTHER PUBLICATIONS

Groutas et al. "Inhibition of Serine Proteases by Functionalized Sulfonamides Coupled to the 1,2,5-thiadiazolidin-3-one 1,1 Dioxide Scaffold" Bioorganic and Medicinal Chemistry, 2001, vol. 9, pp. 1543-1548.*
Albericio et al., "Synthesis of a Sulfahydantoin Library", J. Comb. Chem. vol. 3, pp. 290-300 (2001).
Bright et al., "Competitive particle concentration fluorescence immunoassays for measuring antidiabetic drug levels in mouse plasma" Journal of Immunological Methods, vol. 207, pp. 23-31(1997).
Abstract, Eberle et al., Preparation of microbiocidal N-phenyl-N [4-(-pyridyl)-pyrimidin-2-yl) amines.
Ducry et al., "Synthesis of 1,2,5-Thiadiazolidin-3-one 1,1-Dioxide Derivatives and evaluation of their affinity for MHC Class-II Proteins", Helvetica Chimica, Acta, vol. 82, No. 12, pp. 2432-2447 (1999).
Mantegani et al., "Synthesis and Antihypertensive Activity of 2,4-dioxoimidazolidin-1yl and perhydro-2,4-dioxopyrimidin-1-yl ergoline derivatives", IL FARMACO, vol. 53, pp. 293-304 (1998).

* cited by examiner

*Primary Examiner*—Rebecca Anderson
*Assistant Examiner*—Joseph R. Kosack
(74) *Attorney, Agent, or Firm*—Novartis AG; Mark Milstead

(57) ABSTRACT

Compounds of the formula

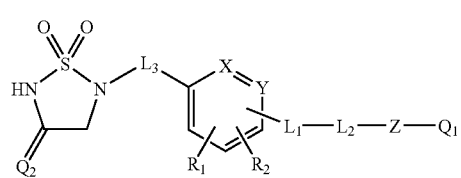

(I)

provide pharmacological agents which are inhibitors of PTPases, in particular, the compounds of formula I inhibit PTP-1B and TC PTP, and thus may be employed for the treatment of conditions associated with PTPase activity. The compounds of the present invention may also be employed for inhibition of other enzymes with a phosphotyrosine binding region such as the SH2 domain. Accordingly, the compounds of formula I may be employed for prevention or treatment of insulin resistance associated with obesity, glucose intolerance, diabetes mellitus, hypertension and ischemic diseases of the large and small blood vessels. The compounds of the present invention may also be employed in the treatment, prevention or control of a number of conditions that accompany Type 2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat or prevent cancer, osteoporosis, neurodegenerative and infectious diseases, and diseases involving inflammation and the immune system.

16 Claims, No Drawings

5-SUBSTITUTED 1,1-DIOXO-1,2,5,-THIADIAZOLIDIN-3-ONE DERIVATIVES

This application claims the benefit of U.S. provisional application No. 60/369,930, filed Apr. 3, 2002 and U.S. provisional application No. 60/369,779, filed Apr. 3, 2002, the contents of which are incorporated herein by reference.

The present invention provides compounds of the formula

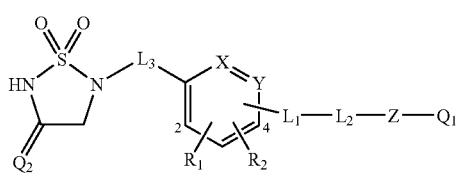

(I)

wherein $R_1$ is hydrogen, halogen, hydroxy, alkoxy, carboxy, cyano, nitro, trifluoromethyl, alkynyl, alkylthio, heteroaralkyl, heteroaralkoxy or heteroaryloxy provided that $R_1$ is located at the 2-position when $L_3$ is —(CHR)$_s$— in which s is zero; or $R_1$ is optionally substituted alkyl, alkenyl, optionally substituted amino, aralkyl, aralkoxy, aralkylthio, aryloxy, arylthio or cycloalkyl provided that a monocyclic aryl group which is substituted at the para position with a methylene or ethylene bridged nitrogen containing heterocycle does not constitute part of $R_1$ when (i) $R_1$ is located at the 2-position and $L_3$ is —(CHR)$_s$— in which s is zero;
(ii) X and Y each are CH; and
(iii) $Q_2$ is oxygen; or
C—$R_1$ may be replaced with nitrogen or N→O; or $R_1$ and $R_2$ combined together with the carbon atoms to which $R_1$ and $R_2$ are attached form an optionally substituted fused 5- to 6-membered aromatic or heteroaromatic ring provided that $R_1$ and $R_2$ are attached to carbon atoms adjacent to each other; or $R_2$ is hydrogen, halogen, hydroxy, alkoxy, cyano, trifluoromethyl, nitro, optionally substituted amino, optionally substituted alkyl, alkylthio, aralkyl, heteroaralkyl, aralkoxy, heteroaralkoxy, aralkylthio, aryloxy, heteroaryloxy, arylthio or cycloalkyl; or $R_2$ is —C(O)$R_3$ wherein
$R_3$ is hydroxy or optionally substituted alkoxy; or
$R_3$ is —NR$_4$R$_5$ in which $R_4$ and $R_5$ are independently hydrogen, optionally substituted alkyl, alkenyl, alkynyl, cycloalkyl, aryl, heterocyclyl, aralkyl or heteroaralkyl;

$L_1$ is a single bond; or
$L_1$ is carbon which combined together with $R_2$ and the carbon atoms to which $L_1$ and $R_2$ are attached form an optionally substituted fused 5- or 6-membered aromatic or heteroaromatic ring provided that $L_1$ and $R_2$ are attached to carbon atoms adjacent to each other; or
$L_1$ is CH or nitrogen which taken together with $R_2$ and the carbon atoms to which $L_1$ and $R_2$ are attached form a fused 5- to 7-membered ring which may be interrupted with one or two heteroatoms selected from oxygen, nitrogen and sulfur provided that $L_1$ and $R_2$ are attached to carbon atoms adjacent to each other; or
$L_1$ is CH, oxygen, sulfur or nitrogen and $L_2$ is carbon which combined together with $L_1$, $R_2$ and the carbon atoms to which $L_1$ and $R_2$ are attached form an optionally substituted fused 5- or 6-membered aromatic or heteroaromatic ring provided that $L_1$ and $R_2$ are attached to carbon atoms adjacent to each other; or $L_1$ is —CH$_2$—, oxygen, sulfur or —NR$_6$— and $L_2$ is CH which taken together with $L_1$, $R_2$ and the carbon atoms to which $L_1$ and $R_2$ are attached form a fused 5- to 7-membered ring which may be interrupted with one or two heteroatoms selected from oxygen, nitrogen and sulfur wherein $R_6$ is hydrogen, optionally substituted alkyl, aralkyl, heteroaralkyl, alkoxycarbonyl, aryloxycarbonyl, carbamoyl, sulfonyl or acyl provided that $L_1$ and $R_2$ are attached to carbon atoms adjacent to each other;

$L_2$ is —(CHR$_7$)$_n$— wherein
$R_7$ is hydrogen, hydroxy, alkoxy, carboxy, optionally substituted alkyl, cycloalkyl, aryl or heteroaryl;
n is zero or an integer from 1 to 4;
Z is —(CHR$_8$)$_m$—, —(CH$_2$)$_m$O(CHR$_8$)$_r$—, —(CH$_2$)$_m$S(CHR$_8$)$_r$— or —(CH$_2$)$_m$NR$_9$(CHR$_8$)$_r$— wherein
$R_8$ is hydrogen, optionally substituted alkyl, cycloalkyl, aryl or heterocyclyl;
$R_9$ is hydrogen, optionally substituted alkyl, cycloalkyl, aryl, heterocyclyl, aralkyl, heteroaralkyl, alkoxycarbonyl, aryloxycarbonyl, heteroaryloxycarbonyl, carbamoyl, sulfonyl, acyl or acylamino;
m and r are independently zero or an integer of 1 or 2;
$Q_1$ is hydrogen, optionally substituted alkyl, cycloalkyl, aryl or heterocyclyl provided that
(i) $Q_1$ is not 2-phenyloxazol-4-yl when
$R_1$ and $R_2$ are hydrogen;
X and Y each are CH;
$L_1$ is a single bond located at the 4-position;
$L_2$ is —(CHR$_7$)$_n$— wherein n is zero;
$L_3$ is —(CHR)$_s$— wherein s is zero;
Z is —(CH$_2$)$_m$O(CHR$_8$)$_r$— wherein $R_8$ is hydrogen, m is zero and r is 2; and
$Q_2$ is oxygen; or
(ii) $Q_1$ is not hydrogen when
$R_1$ and $R_2$ are hydrogen;
X and Y each are CH;
$L_1$ is a single bond;
$L_2$ is —(CHR$_7$)$_n$— wherein n is zero;
$L_3$ is —(CHR)$_r$— wherein R is hydrogen and s is 1;
Z is —(CHR$_8$)$_m$— wherein m is zero; and
$Q_2$ is oxygen; or
$Q_1$ is —C(O)NR$_{4a}$R$_{5a}$, —C(O)R$_{10}$, —C(O)OR$_{10}$ or —S(O)$_q$R$_{10}$ wherein R$_{4a}$ and R$_{5a}$ are as defined for $R_4$ and $R_5$; R$_{10}$ is optionally substituted alkyl, cycloalkyl, aryl, heterocyclyl, aralkyl or heteroaralkyl; q is an integer of 1 or 2; or
$Q_1$ is a radical of the formula

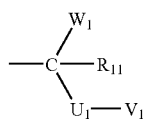

wherein
$W_1$ is aryl, heteroaryl, aralkyl or heteroaralkyl; or
$W_1$ is —C(O)R$_{3a}$ in which R$_{3a}$ is hydroxy or optionally substituted alkoxy; or
R$_{3a}$ is —NR$_{4a}$R$_{5a}$ in which R$_{4a}$ and R$_{5a}$ are as defined for $R_4$ and $R_5$;

$R_{11}$ is hydrogen, alkyl or aryl;
$U_1$ is —C(O)—, —S(O)$_2$— or —(CH$_2$)$_r$— in which r is as defined for Z;
$V_1$ is hydroxy, alkoxy, aryl, heteroaryl, optionally substituted alkyl or cycloalkyl; or
$V_1$ is —NR$_{4b}$R$_{5b}$ in which R$_{4b}$ and R$_{5b}$ are as defined for R$_4$ and R$_5$ provided that
  (i) L$_2$ is —(CHR$_7$)$_n$— in which n is an integer of 1 or 2; and
  (ii) Z is —(CHR$_8$)$_m$— in which m is zero; or
$Q_1$ is a radical of the formula

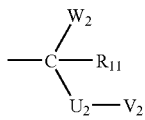

wherein
  $W_2$ is —C(O)R$_{3a}$ in which R$_{3a}$ is hydroxy or optionally substituted alkoxy; or
  $R_{3a}$ is NR$_{4a}$R$_{5a}$ in which R$_{4a}$ and R$_{5a}$ are as defined for R$_4$ and R$_5$;
  $R_{11}$ is hydrogen, alkyl or aryl;
  $U_2$ is —(CH$_2$)$_p$— in which p is zero or 1;
  $V_2$ is —NR$_{4b}$C(O)R$_{5b}$, —NR$_{4b}$C(O)OR$_{5b}$, —NR$_{4b}$C(O)NR$_{4c}$R$_{5b}$ or —NR$_{4b}$S(O)$_2$R$_{5b}$ in which
  $R_{4b}$ and $R_{4c}$ are as defined for R$_{4a}$ and R$_{5b}$ has a meaning as defined for R$_5$ provided that
  (i) L$_2$ is —(CHR$_7$)$_n$— in which n is an integer of 1 or 2; and
  (ii) Z is —(CHR$_8$)$_m$— in which m is zero; or
$Q_1$ is a radical of the formula

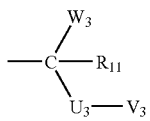

wherein
  $W_3$ is —C(O)R$_{3a}$ in which R$_{3a}$ is hydroxy or optionally substituted alkoxy; or
  $R_{3a}$ is —NR$_{4a}$R$_{5a}$ in which R$_{4a}$ and R$_{5a}$ are as defined for R$_4$ and R$_5$;
  $R_{11}$ is hydrogen, alkyl or aryl;
  $U_3$ is —(CH$_2$)$_p$— in which p is zero or 1;
  $V_3$ is —NHC(O)CHR$_{4b}$NHC(O)R$_{12}$ wherein R$_{4b}$ is as defined for R$_4$; R$_{12}$ is hydrogen, aryl, heterocyclyl, aralkyl, heteroaralkyl, optionally substituted alkyl, alkoxy or cycloalkyl; or
  $R_{12}$ is —NR$_{4c}$R$_{5b}$, in which R$_{4c}$ and R$_{5b}$ are as defined for R$_4$ and R$_5$ provided that
  (i) L$_2$ is —(CHR$_7$)$_n$— in which n is an integer of 1 or 2; and
  (ii) Z is —(CHR$_8$)$_m$— in which m is zero;
$L_3$ is —(CHR)$_s$— wherein
R is hydrogen, carboxy, optionally substituted alkyl, cycloalkyl, aryl or heteroaryl;
s is zero or an integer from 1 to 3;
$Q_2$ is oxygen, sulfur or NR$_{13}$ wherein
$R_{13}$ is hydrogen, hydroxy or lower alkyl;
X and Y are independently CH or nitrogen; or
—X=Y— is sulfur, oxygen or —NR$_{14}$— wherein $R_{14}$ is hydrogen, optionally substituted alkyl, alkoxycarbonyl, acyl, aryloxycarbonyl, heteroaryloxycarbonyl, carbamoyl or sulfonyl;

or a pharmaceutically acceptable salt thereof; or a prodrug derivative thereof.

The compounds of the present invention are inhibitors of protein tyrosine phosphatases (PTPases), in particular, the compounds of formula I inhibit PTPase-1B (PTP-1B) and T-cell PTPase (TC PTP), and thus may be employed for the treatment of conditions mediated by PTPase activity. The compounds of the present invention may also be employed as inhibitors of other enzymes characterized with a phosphotyrosine binding region such as the SH2 domain. Accordingly, the compounds of formula I may be employed for prevention or treatment of insulin resistance associated with obesity, glucose intolerance, diabetes mellitus, hypertension and ischemic diseases of the large and small blood vessels. The compounds of the present invention may also be employed in the treatment, prevention or control of a number of conditions that accompany Type 2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat or prevent cancer, osteoporosis, neurodegenerative and infectious diseases, and diseases involving inflammation and the immune system.

Another embodiment of the present invention is the use of a compound of (I) or a pharmaceutically acceptable salt thereof; or a prodrug derivative thereof for the manufacture of a medicament for inhibiting protein tyrosine phosphatases (PTPases), in particular, the compounds of formula I inhibit PTPase-1B (PTP-1B) and T-cell PTPase (TC PTP), and thus may be employed for the treatment of conditions mediated by PTPase activity, for inhibiting other enzymes characterized with a phosphotyrosine binding region such as the SH2 domain for prevention or treatment of insulin resistance associated with obesity, glucose intolerance, diabetes mellitus, hypertension and ischemic diseases of the large and small blood vessels. The compounds of the present invention may also be employed in the treatment, prevention or control of a number of conditions that accompany Type 2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated, in addition, the for the treatment or prevention of cancer, osteoporosis, neurodegenerative and infectious diseases, and diseases involving inflammation and the immune system.

Likewise the present invention relates to a pharmaceutical composition for inhibiting protein tyrosine phosphatases (PTPases), in particular, the compounds of formula I inhibit PTPase-1B (PTP-1B) and T-cell PTPase (TC PTP), and thus may be employed for the treatment of conditions mediated by PTPase activity, for inhibiting other enzymes characterized with a phosphotyrosine binding region such as the SH2 domain for prevention or treatment of insulin resistance associated with obesity, glucose intolerance, diabetes mellitus, hypertension and ischemic diseases of the large and small blood vessels. The compounds of the present invention may also be employed in the treatment, prevention or control of a number of conditions that accompany Type 2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated, in addition, the for the treatment or prevention of cancer, osteoporosis, neurodegenerative and infectious diseases, and diseases involving inflammation and the immune system.

Listed below are definitions of various terms used to describe the compounds of the instant invention. These definitions apply to the terms as they are used throughout the specification unless they are otherwise limited in specific instances either individually or as part of a larger group.

The term "optionally substituted alkyl" refers to unsubstituted or substituted straight or branched chain hydrocarbon groups having 1 to 20 carbon atoms, preferably 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkanoyl, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those alkyl groups as described above having 1 to 7, preferably 1 to 4 carbon atoms.

The term "halogen" or "halo" refers to fluorine, chlorine, bromine and iodine.

The term "alkenyl" refers to any of the above alkyl groups having at least 2 carbon atoms and containing a carbon to carbon double bond at the point of attachment. Groups having 2 to 4 carbon atoms are preferred.

The term "alkynyl" refers to any of the above alkyl groups having at least two carbon atoms and containing a carbon to carbon triple bond at the point of attachment. Groups having 2 to 4 carbon atoms are preferred.

The term "cycloalkyl" refers to optionally substituted monocyclic, bicyclic or tricyclic hydrocarbon groups of 3 to 12 carbon atoms, each of which may be substituted by one or more substituents such as alkyl, halo, oxo, hydroxy, alkoxy, alkanoyl, acylamino, carbamoyl, alkylamino, dialkylamino, thiol, alkylthio, nitro, cyano, carboxy, carboxyalkyl, alkoxycarbonyl, sulfonyl, sulfonamido, sulfamoyl, heterocyclyl and the like.

Exemplary monocyclic hydrocarbon groups include but are not limited to cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.

The term "alkanoyl" refers to alkyl-C(O)—.

The term "alkanoyloxy" refers to alkyl-C(O)—O—.

The terms "alkylamino" and "dialkylamino" refer to alkyl-NH— and (alkyl)$_2$N—, respectively.

The term "alkanoylamino" refers to alkyl-C(O)—NH—.

The term "alkylthio" refers to alkyl-S—.

The term "alkylaminothiocarbonyl" refers to alkyl-NHC(S)—.

The term "trialkylsilyl" refers to (alkyl)$_3$Si—.

The term "trialkylsilyloxy" refers to (alkyl)$_3$SiO—.

The term "alkylthiono" refers to alkyl-S(O)—.

The term "alkylsulfonyl" refers to alkyl-S(O)$_2$—.

The term "alkoxycarbonyl" refers to alkyl-O—C(O)—.

The term "alkoxycarbonyloxy" refers to alkyl-O—C(O)O—.

The term "carboxycarbonyl" refers to HO—C(O)C(O)—.

The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.

The term "sulfonyl" refers to alkylsulfonyl, arylsulfonyl, heteroarylsulfonyl, aralkylsulfonyl, heteroaralkylsulfonyl and the like.

The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carboxycarbonyl, carbamoyl, alkylaminothiocarbonyl, arylaminothiocarbonyl and the like.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to four substituents such as alkyl, halo, hydroxy, alkoxy, acyl, alkanoyloxy, optionally substituted amino, thiol, alkylthio, nitro, cyano, carboxy, carboxyalkyl, alkoxycarbonyl, carbamoyl, alkylthiono, sulfonyl, sulfonamido, heterocyclyl and the like.

The term "monocyclic aryl" refers to optionally substituted phenyl as described under aryl.

The term "aralkyl" refers to an aryl group bonded directly through an alkyl group, such as benzyl.

The term "aralkanoyl" refers to aralkyl-C(O)—.

The term "aralkylthio" refers to aralkyl-S—.

The term "aralkoxy" refers to an aryl group bonded directly through an alkoxy group.

The term "arylsulfonyl" refers to aryl-S(O)$_2$—.

The term "arylthio" refers to aryl-S—.

The term "aroyl" refers to aryl-C(O)—.

The term "aroylamino" refers to aryl-C(O)—NH—.

The term "aryloxycarbonyl" refers to aryl-O—C(O)—.

The term "heterocyclyl" or "heterocyclo" refers to an optionally substituted, fully saturated or unsaturated, aromatic or nonaromatic cyclic group, for example, which is a 4- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, benzodiazepinyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups that are substituted with 1, 2 or 3 substituents selected from the group consisting of the following:

(a) alkyl;
(b) hydroxy (or protected hydroxy);
(c) halo;
(d) oxo (i.e. =O);
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl or sulfonamido;
(o) aryl;
(p) alkylcarbonyloxy;
(q) arylcarbonyloxy;
(r) arylthio;
(s) aryloxy;
(t) alkylthio;
(u) formyl;
(v) carbamoyl;
(w) aralkyl; and
(x) aryl substituted with alkyl, cycloalkyl, alkoxy, hydroxy, amino, acylamino, alkylamino, dialkylamino or halo.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by e.g. lower alkyl, lower alkoxy or halo.

The term "heteroarylsulfonyl" refers to heteroaryl-S(O)$_2$—.

The term "heteroaroyl" refers to heteroaryl-C(O)—.

The term "heteroaroylamino" refers to heteroaryl-C(O)NH—

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

Pharmaceutically acceptable salts of any compound of the present invention refer to salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methyl-ammonium salts, and salts with amino acids.

Similarly acid addition salts, such as those formed with mineral acids, organic carboxylic acids and organic sulfonic acids e.g. hydrochloric acid, maleic acid and methanesulfonic acid, are possible provided a basic group, such as pyridyl, constitutes part of the structure.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono or disubstituted lower alkyl esters such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester, and the like conventionally used in the art.

The present invention provides cyclic sulfamide derivatives, preferably 1,1-dioxo-1,2,5-thiadiazolidine derivatives, of formula I, pharmaceutical compositions containing them, methods for preparing such compounds and methods of treating conditions associated with PTPase activity, in particular, PTP-1B and TC PTP activity, by administration of a therapeutically effective amount of a compound of the present invention or a pharmaceutical composition thereof. The compounds of the present invention may also be employed in combination with ligands for other enzymes characterized with a phosphotyrosine binding region such as the SH2 domain.

Preferred are the compounds of formula I wherein
Q$_2$ is oxygen;
X and Y each are CH; or
—X=Y— is sulfur;

or a pharmaceutically acceptable salt thereof; or a prodrug derivative thereof.

Further preferred are the compounds of the formula

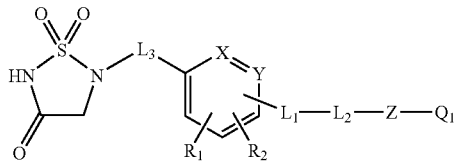

(IA)

wherein
$R_1$ is hydrogen, halogen, hydroxy, alkoxy, trifluoromethyl, alkylthio, heteroaralkyl or heteroaralkoxy provided that $R_1$ is located at the 2-position when $L_3$ is —(CHR)$_s$— in which s is zero; or $R_1$ is optionally substituted alkyl, aralkyl, aralkoxy or aryloxy provided that a monocyclic aryl group which is substituted at the para position with a methylene or ethylene bridged nitrogen containing heterocycle does not constitute part of $R_1$ when
   (i) $R_1$ is located at the 2-position and $L_3$ is —(CHR)$_s$— in which s is zero; and
   (ii) X and Y each are CH;

$R_2$ is hydrogen; or
$R_2$ is —C(O)$R_3$ wherein
$R_3$ is hydroxy or optionally substituted alkoxy; or
$R_3$ is —NR$_4$R$_5$ in which $R_4$ and $R_5$ are independently hydrogen, optionally substituted alkyl, cycloalkyl, aryl, heterocyclyl, aralkyl or heteroaralkyl;

$L_1$ is a single bond; or
$L_1$ is carbon which combined together with $R_2$ and the carbon atoms to which $L_1$ and $R_2$ are attached form an optionally substituted fused 5- or 6-membered aromatic or heteroaromatic ring provided that $L_1$ and $R_2$ are attached to carbon atoms adjacent to each other; or $L_1$ is CH or nitrogen which taken together with $R_2$ and the carbon atoms to which $L_1$ and $R_2$ are attached form a fused 5- to 7-membered ring which may be interrupted with one or two heteroatoms selected from oxygen, nitrogen and sulfur provided that $L_1$ and $R_2$ are attached to carbon atoms adjacent to each other; or $L_1$ is CH, oxygen, sulfur or nitrogen and $L_2$ is carbon which combined together with $L_1$, $R_2$ and the carbon atoms to which $L_1$ and $R_2$ are attached form an optionally substituted fused 5- or 6-membered aromatic or heteroaromatic ring provided that $L_1$ and $R_2$ are attached to carbon atoms adjacent to each other; or $L_1$ is —CH$_2$—, oxygen, sulfur or —NR$_6$— and $L_2$ is CH which taken together with $L_1$, $R_2$ and the carbon atoms to which $L_1$ and $R_2$ are attached form a fused 5- to 7-membered ring which may be interrupted with one or two heteroatoms selected from oxygen, nitrogen and sulfur wherein
   $R_6$ is hydrogen, optionally substituted alkyl, aralkyl, heteroaralkyl, alkoxycarbonyl, aryloxycarbonyl, carbamoyl, sulfonyl or acyl provided that $L_1$ and $R_2$ are attached to carbon atoms adjacent to each other;

$L_2$ is —(CHR$_7$)$_n$— wherein
$R_7$ is hydrogen;
n is zero or an integer of 1 or 2;
Z is —(CHR$_8$)$_m$—, —(CH$_2$)$_m$O(CHR$_8$)$_r$—, —(CH$_2$)$_m$S(CHR$_8$)$_r$— or —(CH$_2$)$_m$NR$_9$(CHR$_8$)$_r$— wherein
$R_8$ is hydrogen or optionally substituted alkyl;

$R_9$ is hydrogen, optionally substituted alkyl, cycloalkyl, aryl, heterocyclyl or acyl;
m and r are independently zero or an integer of 1 or 2;
$Q_1$ is hydrogen, optionally substituted alkyl, cycloalkyl, aryl or heterocyclyl provided that
   (i) $Q_1$ is not 2-phenyloxazol-4-yl when
      $R_1$ and $R_2$ are hydrogen;
      X and Y each are CH;
      $L_1$ is a single bond located at the 4-position;
      $L_2$ is —(CHR$_7$)$_n$— wherein n is zero;
      $L_3$ is —(CHR)$_s$— wherein s is zero; and
      Z is —(CH$_2$)$_m$O(CHR$_8$)$_r$— wherein $R_8$ is hydrogen, m is zero and r is 2; or
   (ii) $Q_1$ is not hydrogen when
      $R_1$ and $R_2$ are hydrogen;
      X and Y each are CH;
      $L_1$ is a single bond;
      $L_2$ is —(CHR$_7$)$_n$— wherein n is zero;
      $L_3$ is —(CHR)$_s$—wherein R is hydrogen and s is 1; and
      Z is —(CHR$_8$)$_m$— wherein m is zero; or
   $Q_1$ is —C(O)NR$_{4a}$R$_{5a}$, —C(O)R$_{10}$, —C(O)OR$_{10}$ or —S(O)$_q$R$_{10}$ wherein $R_{4a}$ and $R_{5a}$ are as defined for $R_4$ and $R_5$; $R_{10}$ is optionally substituted alkyl, cycloalkyl, aryl, heterocyclyl, aralkyl or heteroaralkyl; q is an integer of 1 or 2; or $Q_1$ is a radical of the formula

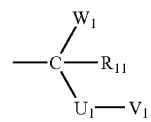

wherein
$W_1$ is aryl, heteroaryl, aralkyl or heteroaralkyl; or
$W_1$ is —C(O)$R_{3a}$ in which $R_{3a}$ is hydroxy or optionally substituted alkoxy; or
$R_{3a}$ is —NR$_{4a}$R$_{5a}$ in which $R_{4a}$ and $R_{5a}$ are as defined for $R_4$ and $R_5$;
$R_{11}$ is hydrogen, alkyl or aryl;
$U_1$ is —C(O)— or —(CH$_2$)$_r$ in which r is as defined for Z;
$V_1$ is hydroxy, alkoxy, aryl, heteroaryl, optionally substituted alkyl or cycloalkyl; or
$V_1$ is —NR$_{4b}$R$_{5b}$ in which $R_{4b}$ and $R_{5b}$ are as defined for $R_4$ and $R_5$ provided that
   (i) $L_2$ is —(CHR$_7$)$_n$— in which n is an integer of 1 or 2; and
   (ii) Z is —(CHR$_8$)$_m$— in which m is zero; or $Q_1$ is a radical of the formula

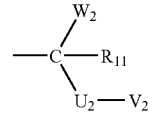

wherein
$W_2$ is —C(O)$R_{3a}$ in which $R_{3a}$ is hydroxy or optionally substituted alkoxy; or
$R_{3a}$ is —NR$_{4a}$R$_{5a}$ in which $R_{4a}$ and $R_{5a}$ are as defined for $R_4$ and $R_5$;
$R_{11}$ is hydrogen, alkyl or aryl;
$U_2$ is —(CH$_2$)$_p$— in which p is zero or 1;

$V_2$ is $-NR_{4b}C(O)R_{5b}$, $-NR_{4b}C(O)OR_{5b}$, $-NR_{4c}C(O)NR_{4c}R_{5b}$ or $-NR_{4b}S(O)_2R_{5b}$ in which $R_{4b}$ and $R_{4c}$ are as defined for $R_4$, and $R_{5b}$ has a meaning as defined for $R_5$ provided that
  (i) $L_2$ is $-(CHR_7)_n-$ in which n is an integer of 1 or 2; and
  (ii) Z is $-(CHR_8)_m-$ in which m is zero; or
$Q_1$ is a radical of the formula

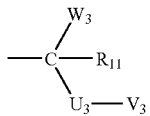

wherein
  $W_3$ is $-C(O)R_{3a}$ in which $R_{3a}$ is hydroxy or optionally substituted alkoxy; or
  $R_{3a}$ is $-NR_{4a}R_{5a}$ in which $R_{4a}$ and $R_{5a}$ are as defined for $R_4$ and $R_5$;
  $R_{11}$ is hydrogen, alkyl or aryl;
  $U_3$ is $-(CH_2)_p-$ in which p is zero or 1;
  $V_3$ is $-NHC(O)CHR_{4b}NHC(O)R_{12}$ wherein $R_{4b}$ is as defined for $R_4$; $R_{12}$ is hydrogen, aryl, heterocyclyl, aralkyl, heteroaralkyl, optionally substituted alkyl, alkoxy or cycloalkyl; or
  $R_{12}$ is $-NR_{4c}R_{5b}$, in which $R_{4c}$ and $R_{5b}$ are as defined for $R_4$ and $R_5$ provided that
    (i) $L_2$ is $-(CHR_7)_n-$ in which n is an integer of 1 or 2; and
    (ii) Z is $-(CHR_8)_m-$ in which m is zero;
  $L_3$ is $-(CHR)_s-$ wherein
  R is hydrogen;
  s is zero or an integer from 1 to 3;
  X and Y each are CH; or
  $-X=Y-$ is sulfur;

or a pharmaceutically acceptable salt thereof; or a prodrug derivative thereof.

Preferred are the compounds of formula IA of the formula

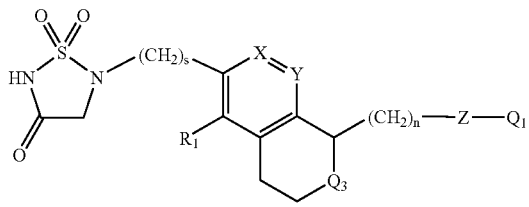

(IB)

wherein
  $R_1$ is hydrogen, halogen, hydroxy, alkoxy, trifluoromethyl, optionally substituted alkyl, alkylthio, aralkyl, aralkoxy, aryloxy, heteroaralkyl or heteroaralkoxy;
  n is zero or an integer of 1 or 2;
  Z is $-(CHR_8)_m-$, $-(CH_2)_mO(CHR_8)_r-$, $(CH_2)_mS(CHR_8)_r-$ or $-(CH_2)_mNR_9(CHR_8)_r-$ wherein
  $R_8$ is hydrogen;
  $R_9$ is hydrogen, optionally substituted alkyl, cycloalkyl, aryl, heterocyclyl or acyl;
  m and r are independently zero or an integer of 1 or 2;
  $Q_1$ is hydrogen, optionally substituted alkyl, cycloalkyl, aryl or heterocyclyl; or $Q_1$ is $C(O)NR_{4a}R_{5a}$, $-C(O)R_{10}$, $-C(O)OR_{10}$ or $-S(O)_qR_{10}$ wherein
  $R_{4a}$ and $R_{5b}$ are independently hydrogen, optionally substituted alkyl, cycloalkyl, aryl, heterocyclyl, aralkyl or heteroaralkyl;
  $R_{10}$ is optionally substituted alkyl, cycloalkyl, aryl, heterocyclyl, aralkyl or heteroaralkyl;
  q is an integer of 1 or 2;
  s is zero or an integer of 1 or 2;
  $Q_3$ is O, S or $-NR_{6a}-$ wherein
  $R_{6a}$ is hydrogen, optionally substituted alkyl, aralkyl, heteroaralkyl, alkoxycarbonyl, aryloxycarbonyl, carbamoyl, sulfonyl or acyl;
  X and Y each are CH; or
  $-X=Y-$ is sulfur;

or a pharmaceutically acceptable salt thereof; or a prodrug derivative thereof.

Preferred are also the compounds of formula IA of the formula

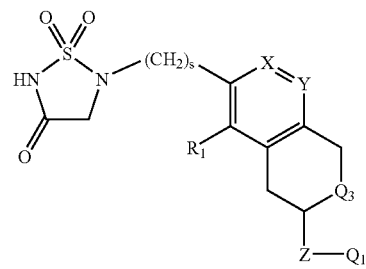

(IC)

wherein
  $R_1$ is hydrogen, halogen, hydroxy, alkoxy, trifluoromethyl, optionally substituted alkyl, alkylthio, aralkyl, aralkoxy, aryloxy, heteroaralkyl or heteroaralkoxy;
  Z is $-(CHR_8)_m-$, $-(CH_2)_mO(CHR_8)_r-$, $(CH_2)_mS(CHR_8)_r-$ or $-(CH_2)_mNR_9(CHR_8)_r-$ wherein
  $R_8$ is hydrogen;
  $R_9$ is hydrogen, optionally substituted alkyl, cycloalkyl, aryl, heterocyclyl or acyl;
  m and r are independently zero or an integer of 1 or 2;
  $Q_1$ is hydrogen, optionally substituted alkyl, cycloalkyl, aryl or heterocyclyl; or
  $Q_1$ is $-C(O)NR_{4a}R_{5a}$, $-C(O)R_{10}$, $-C(O)OR_{10}$ or $-S(O)_qR_{10}$ wherein
  $R_{4a}$ and $R_{5a}$ are independently hydrogen, optionally substituted alkyl, cycloalkyl,1 aryl, heterocyclyl, aralkyl or heteroaralkyl;
  $R_{10}$ is optionally substituted alkyl, cycloalkyl, aryl, heterocyclyl, aralkyl or heteroaralkyl;
  q is an integer of 1 or 2;
  s is zero or an integer of 1 or 2;
  $Q_3$ is O, S or $-NR_{6a}-$ wherein
  $R_{6a}$ is hydrogen, optionally substituted alkyl, aralkyl, heteroaralkyl, alkoxycarbonyl, aryloxycarbonyl, carbamoyl, sulfonyl or acyl;
  X and Y each are CH; or
  $-X=Y-$ is sulfur;

or a pharmaceutically acceptable salt thereof; or a prodrug derivative thereof.

Preferred are also the compounds of formula IA wherein
$R_2$ is hydrogen;
$L_1$ is a single bond;
$L_2$ is —$(CH_2)_n$— in which n is zero or an integer of 1 or 2;

or a pharmaceutically acceptable salt thereof; or a prodrug derivative thereof.

Further preferred are the compounds of formula IA of the formula

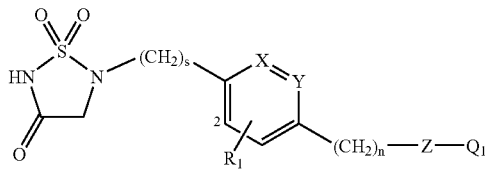

(ID)

wherein
$R_1$ is hydrogen, halogen, hydroxy, alkoxy, trifluoromethyl or alkylthio provided that $R_1$ is located at the 2-position when s is zero; or
$R_1$ is optionally substituted alkyl, aralkyl, aralkoxy or aryloxy provided that a monocyclic aryl group which is substituted at the para position with a methylene or ethylene bridged nitrogen containing heterocycle does not constitute part of $R_1$ when
(i) $R_1$ is located at the 2-position and s is zero; and
(ii) X and Y each are CH;
n is zero or an integer of 1 or 2;
s is zero or 1;
Z is —$(CHR_8)_m$—, —$(CH_2)_mO(CHR_8)_r$—, —$(CH_2)_mS(CHR_8)_r$— or —$(CH_2)_mNR_9(CHR_8)_r$— wherein
$R_8$ is hydrogen;
$R_9$ is hydrogen, optionally substituted alkyl, cycloalkyl, aryl, heteroaryl or acyl;
m and r are independently zero or an integer of 1 or 2;
$Q_1$ is hydrogen, optionally substituted alkyl, cycloalkyl, aryl or heterocyclyl provided that
(i) $Q_1$ is not 2-phenyloxazol-4-yl when
$R_1$ is hydrogen;
X and Y each are CH;
n is zero;
s is zero; and
Z is —$(CH_2)_mO(CHR_8)_r$— wherein $R_8$ is hydrogen, m is zero and r is 2; or
(ii) $Q_1$ is not hydrogen when
$R_1$ is hydrogen;
X and Y each are CH;
n is zero;
s is 1;
Z is —$(CHR_8)_m$— wherein m is zero; or
$Q_1$ is —$C(O)NR_{4a}R_{5a}$, —$C(O)R_{10}$, —$C(O)OR_{10}$ or —$S(O)_qR_{10}$ wherein
$R_{4a}$ and $R_{5a}$ are independently hydrogen, optionally substituted alkyl, cycloalkyl, aryl, heterocyclyl, aralkyl or heteroaralkyl;
$R_{10}$ is optionally substituted alkyl, cycloalkyl, aryl, heterocyclyl, aralkyl or heteroaralkyl;
q is an integer of 1 or 2; or $Q_1$ is a radical of the formula

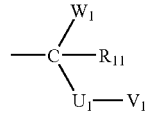

wherein
$W_1$ is aryl, heteroaryl, aralkyl or heteroaralkyl; or
$W_1$ is —$C(O)R_{3a}$ in which $R_{3a}$ is hydroxy or optionally substituted alkoxy; or
$R_{3a}$ is —$NR_{4a}R_{5a}$ in which $R_{4b}$ and $R_{5a}$ are independently hydrogen, optionally substituted alkyl, cycloalkyl, aryl, heterocyclyl, aralkyl or heteroaralkyl;
$R_{11}$ is hydrogen, alkyl or aryl;
$U_1$ is —$C(O)$— or —$(CH_2)_r$— in which r is as defined for Z;
$V_1$ is hydroxy, alkoxy, aryl, heteroaryl, optionally substituted alkyl or cycloalkyl; or
$V_1$ is —$NR_{4b}R_{5b}$ in which $R_{4b}$ and $R_{5b}$ are as defined for $R_{4a}$ and $R_{5a}$ provided that
(i) n is an integer of 1 or 2; and
(ii) Z is —$(CHR_8)_m$— in which m is zero; or
$Q_1$ is a radical of the formula

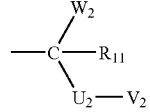

wherein
$W_2$ is —$C(O)R_{3a}$ in which $R_{3a}$ is hydroxy or optionally substituted alkoxy; or
$R_{3a}$ is —$NR_{4a}R_{5a}$ in which $R_{4a}$ and $R_{5a}$ are independently hydrogen, optionally substituted alkyl, cycloalkyl, aryl, heterocyclyl, aralkyl or heteroaralkyl;
$R_{11}$ is hydrogen, alkyl or aryl;
$U_2$ is —$(CH_2)_p$— in which p is zero or 1;
$V_2$ is —$NR_{4b}C(O)R_{5b}$, —$NR_{4b}C(O)OR_{5b}$, —$NR_{4b}C(O)NR_{4c}R_{5b}$ or —$NR_{4b}S(O)_2R_{5b}$ in which
$R_{4b}$ and $R_{4c}$ are as defined for $R_{4a}$, and $R_{5b}$ has a meaning as defined for $R_{5a}$ provided that
(i) n is an integer of 1 or 2; and
(ii) Z is —$(CHR_8)_m$— in which m is zero; or
$Q_1$ is a radical of the formula

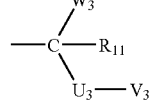

wherein
$W_3$ is —$C(O)R_{3a}$ in which $R_{3a}$ is hydroxy or optionally substituted alkoxy; or
$R_{3a}$ is —$NR_{4a}R_{5a}$ in which $R_{4a}$ and $R_{5a}$ are independently hydrogen, optionally substituted alkyl, cycloalkyl, aryl, heterocyclyl, aralkyl or heteroaralkyl;

$R_{11}$ is hydrogen, alkyl or aryl;
$U_3$ is —$(CH_2)_r$— in which r is zero or 1;
$V_3$ is —NHC(O)CHR$_{4b}$NHC(O)R$_{12}$ wherein $R_{4b}$ is as defined for $R_{4a}$; $R_{12}$ is hydrogen, aryl, heterocyclyl, aralkyl, heteroaralkyl, optionally substituted alkyl, alkoxy or cycloalkyl; or
$R_{12}$ is —NR$_{4c}$R$_{5b}$ in which $R_{4c}$ is as defined for $R_{4a}$, and $R_{5b}$ has a meaning as defined for $R_{5a}$ provided that
(i) n is an integer of 1 or 2; and
(ii) Z is —(CHR$_8$)$_m$— in which m is zero;
X and Y each are CH; or
—X=Y— is sulfur;

or a pharmaceutically acceptable salt thereof; or a prodrug derivative thereof.
Preferred are the compounds of formula ID wherein
—X=Y— is sulfur;

or a pharmaceutically acceptable salt thereof; or a prodrug derivative thereof.
Preferred are also the compounds of formula ID wherein
$R_1$ is bromide;
X and Y each are CH;

or a pharmaceutically acceptable salt thereof; or a prodrug derivative thereof.
Preferred are also the compounds of formula ID wherein
n is zero;
s is 1;
Z is —$(CH_2)_m$— in which m is zero;
$Q_1$ is C(O)NR$_{4a}$R$_{5a}$, —C(O)R$_{10}$, —C(O)OR$_{10}$ or —S(O)$_q$R$_{10}$ wherein
$R_{4a}$ and $R_{5a}$ are independently hydrogen, optionally substituted alkyl, cycloalkyl, aryl, heterocyclyl, aralkyl or heteroaralkyl;
$R_{10}$ is optionally substituted alkyl, cycloalkyl, aryl, heterocyclyl, aralkyl or heteroaralkyl;
q is an integer of 1 or 2;

or a pharmaceutically acceptable salt thereof; or a prodrug derivative thereof.
Preferred are also the compounds of formula ID wherein
n is an integer of 1 or 2;
Z is —$(CH_2)_m$—$(CH_2)_m$O$(CH_2)_r$ or —$(CH_2)_m$S$(CH_2)_r$— wherein
m is zero;
r is zero or 1;
$Q_1$ is optionally substituted alkyl, cycloalkyl, aryl or heterocyclyl;

or a pharmaceutically acceptable salt thereof; or a prodrug derivative thereof.
Preferred are also the compounds of formula ID wherein
n is an integer of 1 or 2;
Z is —$(CH_2)_m$NR$_9$(CH$_2$)$_r$— wherein
$R_9$ is hydrogen, optionally substituted alkyl, cycloalkyl, aryl, heteroaryl or acyl;
m is zero;
r is zero or 1;
$Q_1$ is optionally substituted alkyl, cycloalkyl, aryl or heterocyclyl; or
$Q_1$ is —C(O)NR$_{4a}$R$_{5a}$, —C(O)R$_{10}$, —C(O)OR$_{10}$ or —S(O)$_q$R$_{10}$ wherein
$R_{4a}$ and $R_{5a}$ are independently hydrogen, optionally substituted alkyl, cycloalkyl, aryl, heterocyclyl, aralkyl or heteroaralkyl;

$R_{10}$ is optionally substituted alkyl, cycloalkyl, aryl, heterocyclyl, aralkyl or heteroaralkyl;
q is an integer of 1 or 2;

or a pharmaceutically acceptable salt thereof; or a prodrug derivative thereof.
Preferred are also the compounds of formula ID wherein
n is an integer of 1 or 2;
Z is —$(CH_2)_m$— wherein m is zero;
$Q_1$ is a radical of the formula

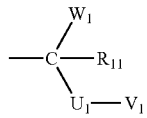

wherein
$W_1$ is aryl, heteroaryl, aralkyl or heteroaralkyl;
$R_{11}$ is hydrogen, alkyl or aryl;
$U_1$ is —C(O)— or —$(CH_2)_r$— in which r is zero;
$V_1$ is aryl, heteroaryl, optionally substituted alkyl or cycloalkyl;

or a pharmaceutically acceptable salt thereof; or a prodrug derivative thereof.
Preferred are also the compounds of formula ID wherein
n is 1;
Z is —$(CH_2)_m$— wherein m is zero;
$Q_1$ is a radical of the formula

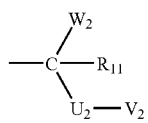

wherein
$W_2$ is —C(O)R$_{3a}$ in which $R_{3a}$ is —NR$_{4a}$R$_{5a}$, and $R_{4a}$ and $R_{5a}$ are independently hydrogen, optionally substituted alkyl, cycloalkyl, aryl, heterocyclyl, aralkyl or heteroaralkyl;
$R_{11}$ is hydrogen;
$U_2$ is —$(CH_2)_p$— in which p is zero;
$V_2$ is —NR$_{4b}$C(O)R$_{5b}$, —NR$_{4b}$C(O)OR$_{5b}$, —NR$_{4b}$C(O)NR$_{4c}$R$_{5b}$ or —NR$_{4b}$S(O)$_2$R$_{5b}$ in which
$R_{4b}$ and $R_{4c}$ are as defined for $R_{4a}$, and $R_{5b}$ has a meaning as defined for $R_{5a}$;

or a pharmaceutically acceptable salt thereof; or a prodrug derivative thereof.
Preferred are also the compounds of formula ID wherein
n is 1;
Z is —$(CH_2)_m$— wherein m is zero;
$Q_1$ is a radical of the formula

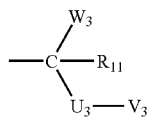

wherein
W$_3$ is —C(O)R$_{3a}$ in which R$_{3a}$ is —NR$_{4a}$R$_{5a}$, and R$_{4a}$ and R$_{5a}$ are independently hydrogen, optionally substituted alkyl, cycloalkyl, aryl, heterocyclyl, aralkyl or heteroaralkyl;
R$_{11}$ is hydrogen;
U$_3$ is —(CH$_2$)$_p$— in which p is zero;
V$_3$ is —NHC(O)CHR$_{4b}$NHC(O)R$_{12}$ wherein R$_{4b}$ is as defined for R$_{4a}$; R$_{12}$ is hydrogen, aryl, heterocyclyl, aralkyl, heteroaralkyl, optionally substituted alkyl or alkoxy; or
R$_{12}$ is —NR$_{4c}$R$_{5b}$ in which R$_{4c}$ and R$_{5b}$ are as defined for R$_{4a}$ and R$_{5a}$;

or a pharmaceutically acceptable salt thereof; or a prodrug derivative thereof.

Particular embodiments of the invention are the compounds of formula I of the working examples, or a pharmaceutically acceptable salt thereof; or a prodrug derivative thereof.

The compounds of the invention depending on the nature of the substituents, may possess one or more asymmetric centers. The resulting diastereoisomers, enantiomers and geometric isomers are encompassed by the instant invention.

Compounds of formula I may be prepared e.g. by cyclizing compounds of the formula

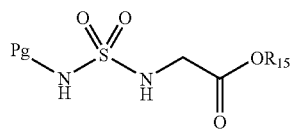

(II)

wherein Pg is an appropriate N-protecting group such as 4-methoxybenzyl, 2,4-dimethoxybenzyl or 2-trimethylsilylethyl, and R$_{15}$ is hydrogen to afford compounds of the formula

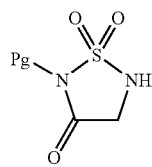

(III)

wherein Pg has a meaning as defined herein above, by treatment with a coupling agent such as diisopropyl carbodiimide (DIC) or 1-ethyl-3-(3-dimethylaminopropyl)carbodiimide hydrochloride (EDCl) in the presence a base such as triethylamine (TEA) or N-methyl-morpholine (NMM) in an organic solvent such as tetrahydrofuran (THF), N,N-dimethyl-formamide (DMF) or dichoromethane (CH$_2$Cl$_2$). The reaction may be carried out in the presence of an additive such as of hydroxybenzotriazole (HOBt).

Compounds of formula II wherein R$_{15}$ is an alkyl group such as methyl, ethyl or t-butyl and the like may be obtained analogously to a literature procedure described by Ducry, L.; Reinelt, S.; Seiler, P.; Diederich, F. *Helvetica Chimica. Acta* 1999, 82, 2432-47.

Compounds of formula II wherein R$_{15}$ is an alkyl group as defined herein above may be converted to compounds of formula II wherein R$_{15}$ is hydrogen according to methods well known in the art, e.g. compounds of formula II in which R$_{15}$ is methyl or ethyl can be treated with an aqueous base such as sodium or potassium hydroxide in an organic solvent such as THF, 1,4-dioxane, methanol (MeOH) or ethanol (EtOH) to afford compounds of formula II wherein R$_{15}$ is hydrogen, or compounds of formula II in which R$_{15}$ is t-butyl may be treated with an acid such as hydrochloric acid (HCl) or trifluoroacetic acid (TFA) in an organic solvent such as CH$_2$Cl$_2$ or ethyl acetate (EtOAc) to afford compounds of formula II wherein R$_{15}$ is hydrogen.

Compounds of formula III wherein Pg has a meaning as defined herein may then be condensed with a variety of alcohols of the formula

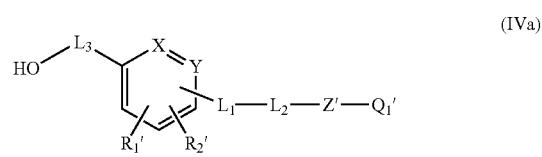

(IVa)

wherein L$_3$ is —(CHR)$_s$— in which s is an integer of 1 to 3; L$_1$, L$_2$, X and Y have meanings as defined herein; and R$_1$', R$_2$', Z' and Q$_1$' represent R$_1$, R$_2$, Z and Q$_1$ as defined herein; or R$_1$', R$_2$', Z' and Q$_1$' are groups convertible to R$_1$, R$_2$, Z and Q$_1$, respectively, under Mitsunobu conditions, e.g., in the presence of reagents such as triphenylphosphine and diethyl azodicarboxylate in an organic solvent such as THF to form compounds of the formula

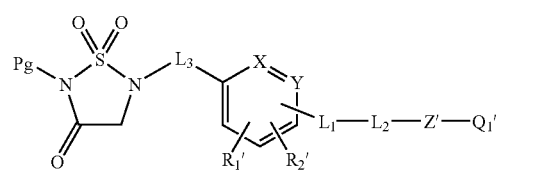

(V)

wherein L$_3$ is —(CHR)$_s$— in which s is an integer of 1 to 3; Pg, L$_1$, L$_2$, X and Y have meanings as defined herein; and R$_1$', R$_2$', Z' and Q$_1$' represent R$_1$, R$_2$, Z and Q$_1$ as de herein; or R$_1$', R$_2$', Z' and Q$_1$' are groups convertible to R$_1$, R$_2$, Z and Q$_1$, respectively.

Alternatively, compounds of formula V wherein L$_3$ is —(CHR)$_s$— in which s is an integer of 1 to 3; Pg, L$_1$, L$_2$, X and Y have meanings as defined herein; and R$_1$', R$_2$', Z' and Q$_1$' represent R$_1$, R$_2$, Z and Q$_1$ as defined herein; or R$_1$', R$_2$', Z' and Q$_1$' are groups convertible to R$_1$, R$_2$, Z and Q$_1$, respectively, may be obtained by condensing a compound of formula III wherein Pg has a meaning as defined herein with an alkylating agent of the formula

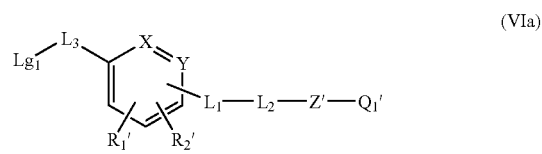

(VIa)

wherein $L_3$ is —(CHR)$_s$— in which s is an integer of 1 to 3; $Lg_1$ represents a leaving group, such as a halide or a sulfonate, especially bromide, chloride, methanesulfonate or trifluoromethanesulfonate;

$L_1$, $L_2$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, in the presence of a base such as 1,8-diazabicyclo[5,4,0]-undec-7-ene (DBU) in an inert solvent such as $CH_2Cl_2$, THF or DMF to afford compounds of formula V.

Compounds of formula II wherein Pg has a meaning as defined herein may also be coupled with a variety of boronic acids of the formula

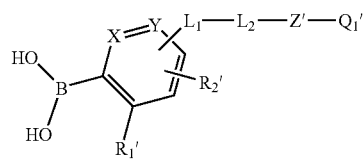
(IVb)

wherein $L_1$, $L_2$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively, in the presence of a copper catalyst such as copper(II) acetate and a base such as cesium(II) carbonate ($Ce_2CO_3$) or TEA in an organic solvent such as THF, 1,4-dioxane or $CH_2Cl_2$ to afford compounds of the formula V wherein wherein $L_3$ is —(CHR)$_s$— in which s is zero; Pg, $L_1$, $L_2$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively.

Alternatively, compounds of formula V wherein $L_3$ is —(CHR)$_s$— in which s is zero; Pg, $L_1$, $L_2$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively, may be obtained by reacting a compound of formula III wherein Pg has a meaning as defined herein with a compound of the formula

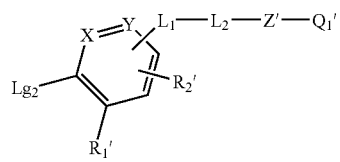
(VIb)

wherein $Lg_2$ represents a leaving group such as halide or trifluoromethanesulfonate, preferably fluoride or chloride; $L_1$, $L_2$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively, using conditions well know in the art or using methods described herein or modifications thereof, e.g., a compound of formula III may be first treated with a base such as $Ce_2CO_3$, or sodium, lithium or potassium bis(trimethylsilyl)amide in an inert organic solvent such as THF or 1,4-dioxane followed by reaction with a compound of formula VIb at a temperature ranging from room temperature (RT) to 110° C.

Compounds of formula V wherein Pg, $L_1$, $L_2$, $L_3$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively, may be converted to compounds of the formula

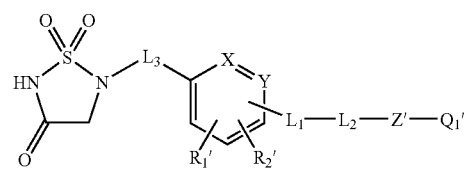
(I')

by removal of the N-protecting group according to methods well known in the art, e.g. in particular when Pg is 4-methoxybenzyl or 2,4-dimethoxybenzyl group using hydrogen in the presence of a catalyst such as palladium on carbon in a polar organic solvent such as MeOH or EtOAc, or by treatment with an acid such as TFA in an organic solvent such as $CH_2Cl_2$, preferably in the presence of an additive such as t-butyldimethylsilane or triethylsilane, or in particular when Pg is 2-trimethylsilylethyl group using a fluoride reagent such as tetra-n-butylammoniumfluoride in an organic solvent such as THF or 1,4-dioxane.

In addition, compounds of formula I' wherein $L_1$, $L_2$, $L_3$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively, may be prepared by condensing compounds of the formula

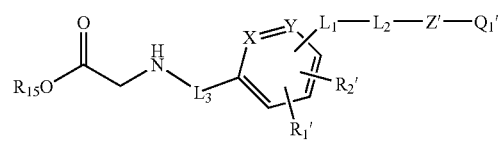
(VII)

wherein $R_{15}$ is an alkyl group as defined herein; and $L_1$, $L_2$, $L_3$, X, Y, $R_1'$, $R_2'$, $Z'$ and $Q_1'$ have meanings as defined for formula I', with a sulfamoyl chloride analog of the formula

$ClS(O)_2NHR_{16}$ (VIII)

wherein $R_{16}$ is hydrogen or alkoxycarbonyl such as t-butoxycarbonyl or 2-trimethylsilyl-ethoxycarbonyl, in the presence of a base such as TEA or NMM in an organic solvent such as acetonitrile (MeCN), $CH_2Cl_2$ or THF to form compounds of the formula

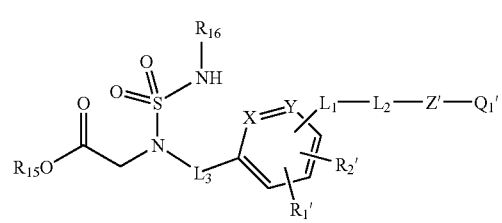
(IX)

wherein $R_{15}$, $R_{16}$, $L_1$, $L_2$, $L_3$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively.

Compounds of formula VIII wherein $R_{16}$ is alkoxycarbonyl may be obtained by reacting chlorosulfonyl isocyanate with the appropriate alcohol in an organic solvent such as MeCN, $CH_2Cl_2$ or THF.

Compounds of formula VII may be prepared using methods well known in the art or according to methods described herein or modifications thereof, e.g., according to the method described by Tohru Fukuyama et. al., *Tet. Lett.* 1997, 38 (33), 5831-34; or by reacting amines of the formula

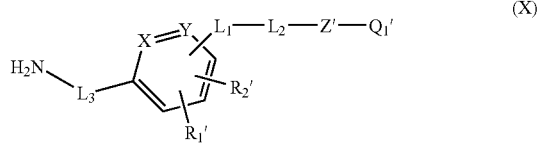
(X)

wherein $L_1$, $L_2$, $L_3$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively, with an acetate of the formula

Lg$_1$-CH$_2$—C(O)—O—R$_{15}$ (XI)

wherein $Lg_1$ and $R_{15}$ have meanings as defined herein, in the presence of a base such as TEA or NMM in an inert solvent such as THF or 1,4-dioxane.

Amines of formula X may be obtained according to methods well known in the art, e.g, as described in PCT Patent Application Publications WO/9946236, WO/9946244, WO/9946268, WO/0119830, WO/0119831, WO/0204458 and WO/0204459, or using methods described herein in the Examples, or modifications thereof.

Compounds of formula IX wherein $R_1$s, $L_1$, $L_2$, $L_3$, X and Y have meanings as defined herein; $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively; and $R_{16}$ is alkoxycarbonyl, may be converted to compounds of formula IX wherein $R_{16}$ is hydrogen according to methods known in the art, or using methods described herein, or modifications thereof, e.g., compounds of formula IX wherein $R_{16}$ is t-butoxycarbonyl may be treated with an acid such as TFA, neat or in an organic solvent such as $CH_2Cl_2$, or compounds of formula IX wherein $R_{16}$ is 2-trimethylsilylethoxycarbonyl may be treated with a fluoride reagent such as tetra-n-butylammoniumfluoride in an organic solvent such as THF or 1,4-dioxane to afford compounds of formula IX wherein $R_{16}$ is hydrogen.

Alternatively, compounds of formula IX wherein $R_{15}$, $L_1$, $L_2$, $L_3$, X and Y have meanings as defined herein; $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively; and $R_{16}$ is hydrogen, may be obtained by first condensing amines of formula X with sulfamide in an aqueous solution and in the presence of a base such as sodium bicarbonate ($NaHCO_3$) at an elevated temperature, preferably at the boiling point of the solution, to afford compounds of the formula

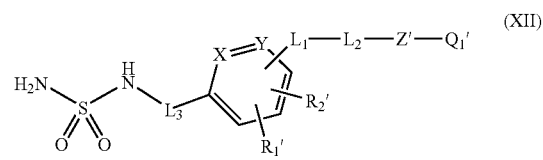
(XII)

wherein $L_1$, $L_2$, $L_3$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively. Compound of formula XII may then be converted to compound of formula IX in which $R_{16}$ is hydrogen by the reaction with acetates of formula XI in the presence of a base such as sodium hydride in an inert solvent such as THF or DMF.

Compounds of formula IX wherein $R_{15}$, $R_{16}$, $L_1$, $L_2$, $L_3$, X and Y have meanings as defined herein; and $R_1'$, $R_2'$, $Z'$ and $Q_1'$ represent $R_1$, $R_2$, Z and $Q_1$ as defined herein; or $R_1'$, $R_2'$, $Z'$ and $Q_1'$ are groups convertible to $R_1$, $R_2$, Z and $Q_1$, respectively, can be cyclized to form compounds of formula I' using methods and conditions well known in the art, or as illustrated herein in the Examples, or modifications thereof.

In a particular embodiment of the invention, compounds of formula I may be prepared as illustrated in Scheme I.

Scheme I

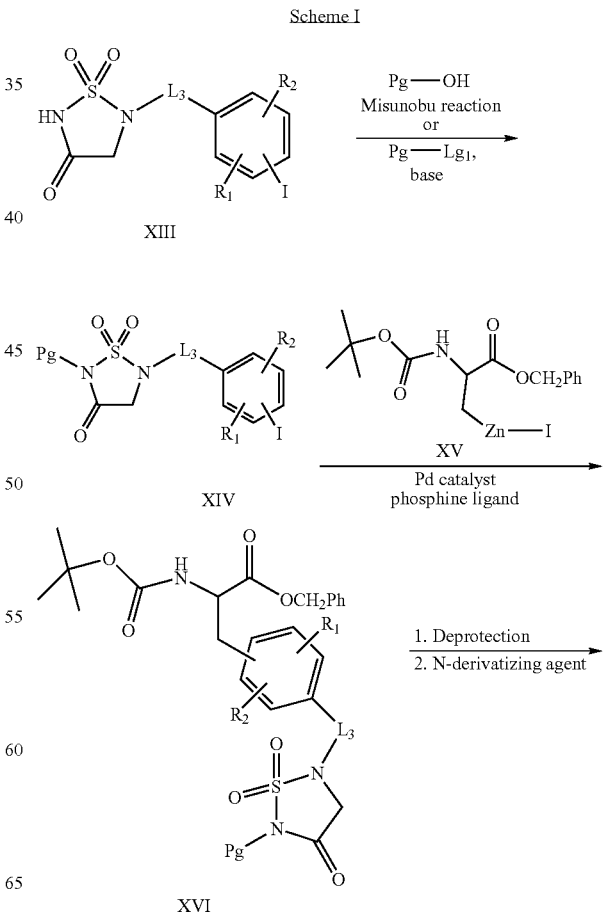

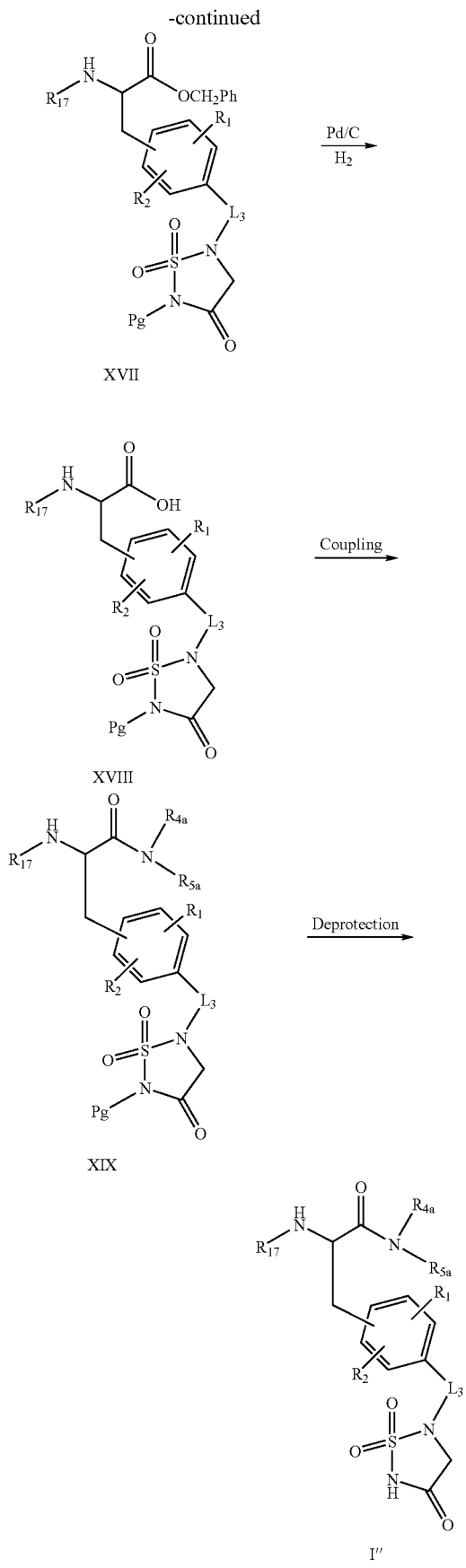

Compounds of formula XIII wherein $R_1$, $R_2$ and $L_3$ have meanings as defined herein, may be reacted with alcohols of the formula Pg-OH wherein Pg is a N-protecting group as defined herein, under Mitsunobu conditions, e.g., in the presence of triphenylphoshine and diethyl azodicarboxylate and an organic solvent such as THF, to afford compounds of formula XIV. Alternatively, compounds of formula XIII may be converted to compounds of formula XIV by treatment with an alkylating agent of the formula Pg-$Lg_1$ in which Pg and $Lg_1$ have meanings as defined herein, in the presence of a base such as DBU in an inert solvent such as $CH_2Cl_2$, THF or DMF. The subsequent reaction between compounds of formula XIV and the organozinc reagent XV may be carried out in the presence of palladium(0) catalyst such as tris (dibenzylideneacetone)-dipalladium(0) acetate and a phosphine ligand such as tritolylphosphine in an organic solvent such as DMF to form compounds of formula XVI. Compounds of formula XVI may be treated with an acid such as TFA to remove the t-butoxycarbonyl protecting group. The resulting amines, or acid addition salts thereof, are then reacted with a N-derivatizing agent, such as an activated derivative of a carboxylic acid, a chloroformate, an isocyanate or a sulfonyl chloride, in the presence of a base such as TEA, diisopropylethylamine or NMM in an inert solvent such as MeCN, $CH_2Cl_2$, DMF or THF to obtain compounds of formula XVII wherein $R_{17}$ is —C(O)$R_{5b}$, —C(O)O$R_{5b}$, —C(O)N$R_{4c}R_{5b}$ or —S(O)$_2R_{5b}$, respectively, and $R_{4a}$ and $R_{5b}$ have meanings as defined herein. The benzyl ester may then be removed, e.g., by catalytic hydrogenation, to afford carboxylic acids of formula XVIII. Coupling of an activated derivative of a carboxylic acid of formula XVIII with amines of the formula HN$R_{4a}R_{5a}$ yields amides of formula XIX wherein $R_{4a}$ and $R_{5a}$ have meanings as defined herein. Finally, treatment with TFA affords compounds of formula I″.

In the processes cited herein, activated derivatives of carboxylic acids, e.g., those of formula XVIII, include acid chlorides, bromides and fluorides, mixed anhydrides, lower alkyl esters, and activated esters thereof, and adducts formed with coupling agents such as EDCl, DIC, O-(1,2-dihydro-2-oxo-1-pyridyl)-N,N,N',N'-tetramethyluronium tetrafluoroborate and the like. Mixed anhydrides are preferably such from pivalic acid, or lower alkyl hemiesters of carbonic acids, such as ethyl or isobutyl analogs. Activated esters include, for example, succinimido, phthalimido or 4-nitrophenyl esters. The reaction of an activated derivative of a carboxylic acid, e.g., those of formula XVIII, with an amine may be carried out in the presence of a base such as TEA, diisopropylethylamine or NMM in an inert solvent such as $CH_2Cl_2$, DMF or THF. Carboxylic acids, e.g. those of formula XVIII, can be converted to their activated derivatives using methods described herein or modifications thereof or using methods well known in the art.

In another embodiment of the invention, compounds of formula I may be prepared as illustrated in Scheme II.

Scheme II
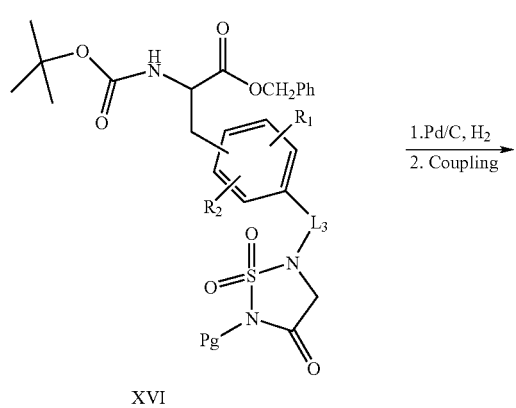
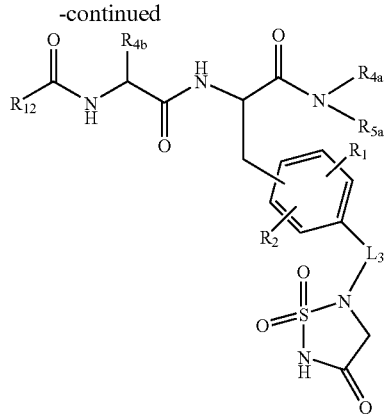
Yet in another embodiment of the invention, compounds of formula I may be prepared as illustrated in Scheme III.
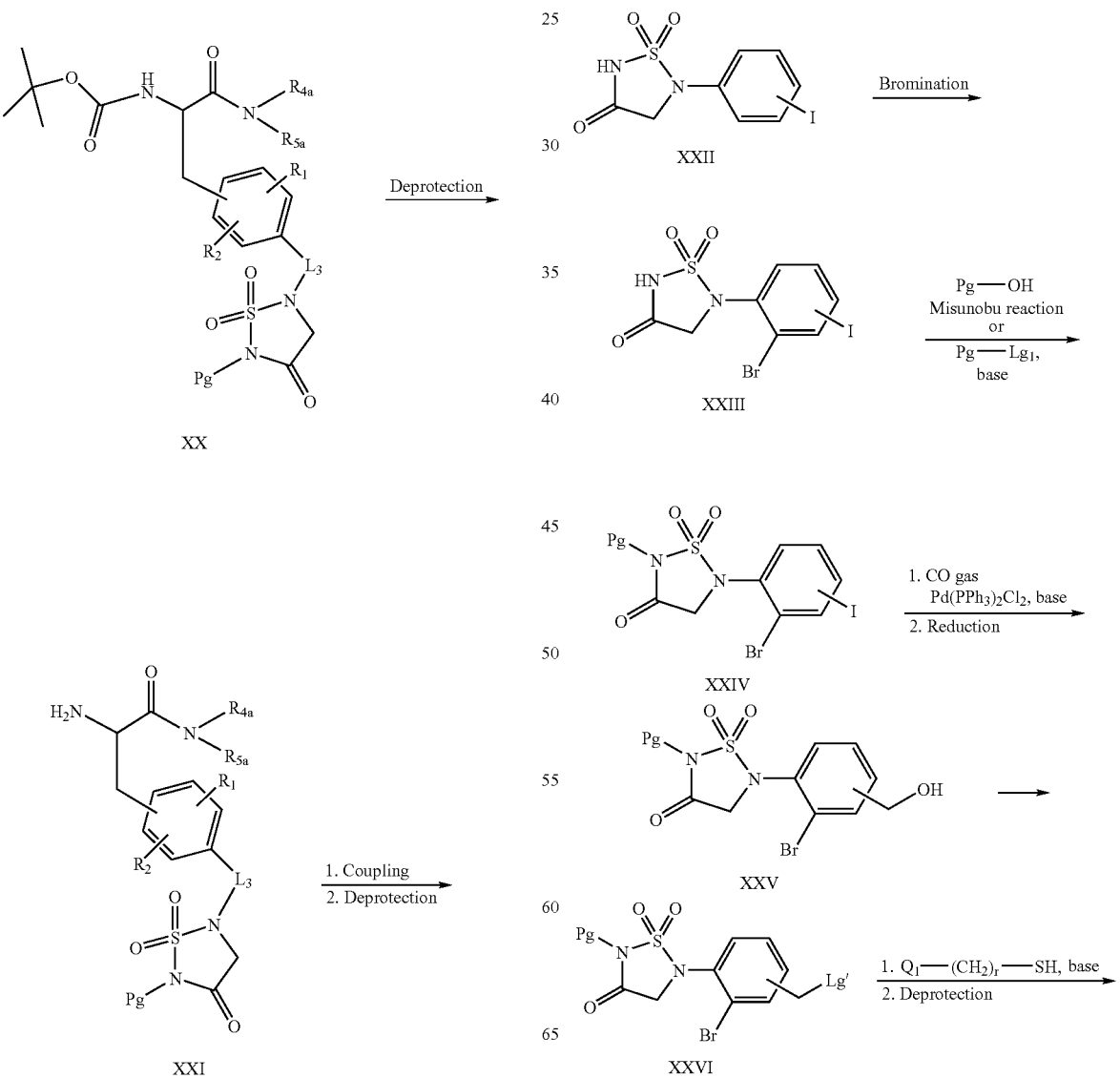

-continued

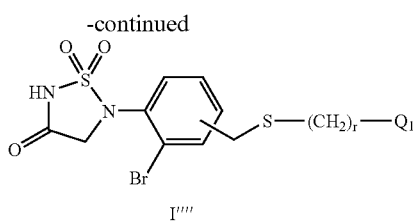

I''''

Compounds of formula XXII may be converted to compounds of formula XXIII by the treatment with a brominating agent, e.g., dibromo isocyanuric acid, in an organic solvent such as THF or 1,4-dioxane. Compounds of formula XXIII may then be reacted with an alcohol of the formula Pg-OH wherein Pg is a suitable N-protecting group as defined herein, under Mitsunobu conditions, e.g., in the presence of triphenylphoshine and diethyl azodicarboxylate in an organic solvent such as THF to afford compounds of formula XXIV. Alternatively, compounds of formula XXIII may be converted to compounds of formula XXIV by treatment with an alkylating agent of the formula Pg-$Lg_1$ in which Pg has meanings as defined herein and $Lg_1$ represents a leaving group such as defined herein, in the presence of a base such as DBU in an inert solvent such as $CH_2Cl_2$, THF or DMF. The subsequent reaction with carbon monoxide gas (CO) in the presence of a palladium catalyst such as bis(triphenylphoshine)palladium(II) chloride and a base such as $NaHCO_3$ in an organic solvent such as DMF, followed by treatment with a reducing agent such as sodium borohydride, or sodium cyanoborohydride in an inert solvent such as THF affords alcohols of formula XXV. Compounds of formula XXV may be converted to compounds of formula XXVI wherein Lg' represents a leaving group as defined herein for $Lg_1$, using methods well known in the art. Compounds of formula XXVI may be reacted with thiols of the formula $Q_1$-$(CH_2)_r$—SH wherein r is, e.g., zero or 1, and $Q_1$ is optionally substituted alkyl, cycloalkyl, aryl or heterocyclyl, in the presence of base such as $Ce_2CO_3$ in an organic solvent such as DMF. The resulting sulfides may then be deprotected by treatment with acid such as TFA to afford compounds of formula I''''.

In starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well known protecting groups that meet these conditions and their introduction and removal are described, for example, in McOmie, "*Protective Groups in Organic Chemistry*", Plenum Press, London, New York (1973); and Greene and Wuts, "*Protective Groups in Organic Synthesis*", John Wiley and Sons, Inc, New York (1999).

The above mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an inter-mediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The carboxylic acid intermediates can thus be resolved into their optical antipodes e.g. by fractional crystallization of d- or l-(alpha-methylbenzylamine, cinchonidine, cinchonine, quinine, quinidine, ephedrine, dehydroabietylamine, brucine or strychnine)-salts. Racemic products can also be resolved by chiral chromatography, e.g. high pressure liquid chromatography using a chiral adsorbent.

Finally, compounds of the invention are either obtained in the free form, as a salt thereof if salt forming groups are present or as prodrug derivatives thereof.

NH group of the 1,1-dioxo-1,2,5-thiadiazolidin-3-one moiety, may be converted into salts with pharmaceutically acceptable bases. Salts may be formed using conventional methods, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit protein tyrosine phosphatases, and for the treatment of conditions associated with PTPase activity, in particular, PTP-1B and TC PTP activity. Such conditions include insulin resistance associated with obesity, glucose intolerance, diabetes mellitus, hypertension and ischemic diseases of the large and small blood vessels. The compounds of the present invention may also be employed in the treatment, prevention or control of a number of conditions that accompany Type 2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat or prevent cancer, osteoporosis, neurodegenerative and infectious diseases, and diseases involving inflammation and the immune system. The said pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The pharmaceutical formulations contain a therapeutically effective amount of a compound of the invention as defined above, either alone or in a combination with another therapeutic agent, e.g., each at an effective therapeutic dose as reported in the art. Such therapeutic agents include insulin, insulin derivatives and mimetics, insulin secretagogues such as the sulfonylureas, e.g., Glipizide and Amaryl, insulinotropic sulfonylurea receptor ligands such as meglitinides, e.g., nateglinide and repaglinide, PPARα and/or PPARγ ligands, biguanides such as metformin, aldose reductase inhibitors, alpha-glucosidase inhibitors such as acarbose, glycogen phosphorylase inhibitors, GLP-1, GLP-1 analogs such as Exendin-4 and GLP-1 mimetics, and DPP-IV inhibitors. Thus, the methods of treatment or prevention described herein may further include administering to mammals a second anti-diabetic compound in an amount effective to treat or prevent diabetes. Similarly, the methods of treatment of diabetes may include the administration of a cholesterol biosynthesis inhibitor, particularly an HMG-CoA reductase inhibitor such as lovastatin, pitavastatin, simvastatin, pravastatin, cerivastatin, mevastatin, velostatin, fluvastatin, dalvastatin, atorvastatin, rosuvastatin and rivastatin, a squalene synthase inhibitor or FX52 and LXR ligands, cholestyramine, fibrates, nicotinic acid, and aspirin in an amount effective to improve the lipid profile. The combination of a cholesterol lowering agent, anti-hypertensive agent or anti-obesity agent with a PTPase inhibitor, in particular a PTP-1B inhibitor, may be beneficial in the treatment or prevention of atherosclerosis, hypertension, obesity and other conditions that often are associated with Type 2 diabetes. A compound of the present invention may be administered either simultaneously, before or after the other active ingredient, either separately by the same or different route of administration or together in the same pharmaceutical formulation.

A unit dosage for a mammal of about 50 to 70 kg may contain between about 1 mg and 1000 mg, advantageously between about 5 mg to 500 mg of the active ingredient. The therapeutically effective dosage of a compound of formula I is dependent on the species of warm-blooded animal (mammal), the body weight, age and individual condition, on the form of administration, and on the compound involved.

The compounds of the present invention are inhibitors of PTPases, in particular PTP-1B and TC PTP, and thus may be employed for the treatment of conditions associated with PTPase activity, in particular with PTP-1B and TC PTP activity, as described herein, e.g. insulin resistance associated with obesity, glucose intolerance, diabetes mellitus, hypertension and ischemic diseases of the large and small blood vessels, and conditions that accompany Type 2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is a component. In addition, the compounds of this invention may be employed to treat or prevent cancer, osteoporosis, neurodegenerative and infectious diseases, and diseases involving inflammation and the immune system.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-3}$ molar and $10^{-9}$ molar concentrations. A therapeutically effective amount in vivo may range depending on the route of administration, between about 1 and 500 mg/kg, preferably between about 5 and 100 mg/kg.

The activity of a compound according to the invention may be assessed by the following methods or by following methods well described in the art (e.g. Peters G. et al. *J. Biol. Chem,* 2000, 275, 18201-09).

For example, the PTP-1B inhibitory activity in vitro may be determined as follows:

Assessment of human PTP-1B (hPTP-1B) activity in the presence of various agents is determined by measuring the amount of inorganic phosphate released from a phosphopeptide substrate using a 96-well microtiter plate format. The assay (100 µL) is performed in an assay buffer comprised of 50 mM TRIS (pH 7.5), 50 mM NaCl, 3 mM DTT at ambient temperature. The assay is typically performed in the presence of 0.4% dimethyl sulfoxide (DMSO). However, concentrations as high as 10% are used with certain poorly soluble compounds. A typical reaction is initiated by the addition of 0.4 pmoles of hPTP-1B (amino acids 1-411) to wells containing assay buffer, 3 nmoles of the synthetic phosphopeptide substrate (GNGDpYMPMSPKS), and the test compound. After 10 min, 180 µL malachite green reagent (0.88 mM malachite green, 8.2 mM ammonium molybdate, aqueous 1 N HCl, and 0.01% Triton X-100) is added to terminate the reaction. Inorganic phosphate, a product of the enzyme reaction, is quantitiated after 15 min as the green color resulting from complexing with the Malichite reagent and is determined as an $A_{620}$ using a Molecular Devices (Sunnyvale, Calif.) SpectraMAX Plus spectrophotometer. Test compounds are solubilized in 100% DMSO (Sigma, D-8779) and diluted in DMSO. Activity is defined as the net change in absorbance resulting from the activity of the uninhibited hPTP-1B$_{[1-411]}$ minus that of a tube with acid-inactivated hPTP-1B$_{[1-411]}$.

The hPTP-1B$_{[1-411]}$ is cloned by PCR from a human hippocampal cDNA library (Clonetech) and inserted into a pET 19-b vector (Novagen) at the Nco1 restriction site. *E. coli* strain BL21 (DE3) is transformed with this clone and stored as a stock culture in 20% glycerol at −80° C. For enzyme production, a stock culture is inoculated into Lb/Amp and grown at 37° C. Expression of PTP-1B is initiated by induction with 1 mM IPTG after the culture had reached an $OD_{600}$=0.6. After 4 h, the bacterial pellet is collected by centrifugation. Cells are resuspended in 70 mL lysis buffer (50 mM Tris, 100 mM NaCl, 5 mM DTT, 0.1% Triton X-100, pH7.6), incubated on ice for 30 min then sonicated (4×10 sec bursts at full power). The lysate is centrifuged at 100,000×g for 60 min and the supernatant is buffer exchanged and purified on a cation exchange POROS 20SP column followed by an anion exchange Source 30Q (Pharmacia) column, using linear NaCl gradient elutions. Enzyme is pooled, adjusted to 1 mg/mL and frozen at −80° C.

Competitive binding to the active site of the enzyme can be determined as follows:

Ligand binding is detected by acquiring $^1$H-$^{15}$N HSQC spectra on 250 µL of 0.15 mM PTP-1B$_{[1-298]}$ in the presence and absence of added compound (1-2 mM). The binding is determined by the observation of $^{15}$N- or $^1$H-amide chemical shift changes in two dimensional HSQC spectra upon the addition of a compound to $^{15}$N-label protein. Because of $^{15}$N spectral editing, no signal from the ligand is observed, only protein signals. Thus, binding can be detected at high compound concentrations. Compounds which caused a pattern of chemical shift changes similar to the changes seen with known active site binders are considered positive.

All proteins are expressed in *E. coli* BL21 (DE3) containing plasmids constructed using pET19b vectors (Novagen). Uniformly $^{15}$N-labeled PTP-1B$_{1-298}$ is produced by growth of bacteria on minimal media containing $^{15}$N-labeled ammonium chloride. All purification steps are performed at 4° C. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 µM PMSF and 100 µg/mL DNase I. The cells are lysed by sonication. The pellet is collected at 35,000×g, resuspended in 25 mL of lysis buffer using a Polytron and collected as before. The two supernatants are combined and centrifuged for 30 min at 100,000×g. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. Protein is eluted from the column using a linear salt gradient (75-500 mM NaCl in 25 CV). Fractions containing PTP-1B's are identified and pooled according to SDS-PAGE analyses. PTP-1B$_{1-298}$ is further purified by anion exchange chromatography using a POROS 20 HQ column (1×10 cm). The pool from cation exchange chromatography is concentrated and buffer exchanged in 50 mM Tris-HCl, pH 7.5 containing 75 mM NaCl and 5 mM DTT. Protein is loaded onto column at 20 mL/min and eluted using a linear NaCl gradient (75-500 mM in 25 CV). Final purification is performed using Sephacryl S-100 HR (Pharmacia)(50 mM HEPES, 100 mM NaCl, 3 mM DTT, pH 7.5). The NMR samples are composed of uniformly $^{15}$N-labeled PTP-1B$_{1-298}$ (0.15 mM) and inhibitor (1-2 mM) in a 10% $D_2O$/90% $H_2O$ Bis-Tris-d$_{19}$ buffer (50 mM, pH=6.5) solution containing NaCl (50 mM), DL-1,4-Dithiothreitol-d$_{10}$ (5 mM) and Sodium azide (0.02%).

The $^1$H-$^{15}$N HSQC NMR spectra are recorded at 20° C., on Bruker DRX500 or DMX600 NMR spectrometers. In all NMR experiments, pulsed field gradients are applied to afford the suppression of solvent signal. Quadrature detection in the indirectly detected dimensions is accomplished by using the States-TPPI method. The data are processed using Bruker software and analyzed using NMRCompass software (MSI) on Silicon Graphics computers.

The glucose and insulin lowering activity in vivo may be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1 tail blood samples are taken at 8:00 am and plasma glucose levels are determined. The animals are randomly assigned to the control and compound groups. The means of plasma glucose values of the groups are matched. Animals are then orally dosed with vehicle (0.5% carboxymethyl-cellulose with 0.2% Tween-80) or compounds (at 30 mg/kg) in vehicle. The mice are dosed daily for a total of 3 days. On day 4 basal blood samples are taken. The plasma samples are analyzed for glucose concentrations using a YS12700 Dual Channel Biochemistry Analyzer (Yellow Springs Instrument Co., Yellow Springs, Ohio) and insulin concentrations using an ELISA assay.

The following Examples are intended to illustrate the invention and are not to be construed as being limitations thereon. Temperatures are given in degrees Centigrade (° C.). If not mentioned otherwise, all evaporations are performed under reduced pressure, preferably between about 15 and 100 mmHg (=20-133 mbar). The structure of final products, intermediates and starting materials is confirmed by standard analytical methods, e.g. microanalysis, melting point (mp) and spectroscopic characteristics (e.g. MS, IR, NMR). In general, abbreviations used are those conventional in the art.

EXAMPLE 1

5-Benzyl-1,1-dioxo-1,2,5-thiadiazolidin-3-one

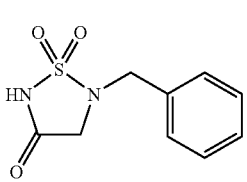

A. N-Benzyl-N-sulfamidoglycine ethyl ester

A solution of N-benzylglycine ethyl ester (6.47 g, 34.5 mmol) and TEA (10.47 g, 103 mmol) in MeCN (10 mL) is treated with a solution of sulfamoyl chloride (3.99 g, 34.5 mmol) in MeCN (20 mL) dropwise over 20 min. The mixture is stirred for 3 h and filtered. The filtrate is concentrated and the residue is partitioned between EtOAc and aqueous 3N hydrochloric acid (HCl). The organic layer is washed with aqueous 3N HCl, saturated aqueous sodium chloride (NaCl) solution and dried over magnesium sulfate ($MgSO_4$). The solvent is evaporated to afford N-benzyl-N-sulfamidoglycine ethyl ester as a yellow oil: $[M-1]^-=272$.

B. 5-Benzyl-1,1-dioxo-1,2,5-thiadiazolidin-3-one

Sodium hydride (9 mg, 0.367 mmol) is added to a solution of the title A compound, N-benzyl-N-sulfamidoglycine ethyl ester (100 mg, 0.367 mmol) in dry THF (5 mL) under $N_2$ atmosphere. The mixture is stirred at RT (RT) for 3 days. The mixture is acidified with 3N HCl in EtOAc. The solvents are evaporated and the residue is purified by C8 preparative reverse phase LC-MS chromatography using 5%→100% MeCN in water over 13 min to afford 5-benzyl-1,1-dioxo-1,2,5-thiadiazolidin-3-one as a white solid: $[M-1]^-=225$.

(1) EXAMPLE 2

5-Naphthalen-1-ylmethyl-1,1-dioxo-1,2,5-thiadiazolidin-3-one

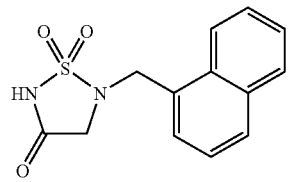

A. N-(1-Naphthylmethyl)glycine ethyl ester

A solution of 1-aminomethylnaphthalene (2.15 g, 13.6 mmol) and TEA (1.65 g, 16.3 mmol) in $CH_2Cl_2$ (50 mL) is treated with ethyl bromoacetate (2.28 g, 13.6 mmol) dropwise over 90 min. The mixture is stirred at RT for 3 h and washed with water. The organic layer is dried over anhydrous $MgSO_4$ and concentrated. The residue is flash chromatographed on silica gel using $CH_2Cl_2$→1% MeOH in $CH_2Cl_2$ as the eluent to afford N-(1-naphthyl-methyl)-glycine ethyl ester as a yellow oil: $[M+1]^+=244$.

B. N-(1-Naphthylmethyl)-N-sulfamidoglycine ethyl ester

A solution of the title A compound, N-(1-naphthylmethyl) glycine ethyl ester (870 mg, 3.58 mmol) and TEA (1.09 g, 10.7 mmol) in MeCN (10 mL) is added dropwise over 10 min to a solution of sulfamoyl chloride (825 mg, 7.15 mmol) in MeCN (10 mL). The mixture is stirred for 16 h and the solvent is evaporated. The residue is partitioned between EtOAc and water. The organic layer is dried over $MgSO_4$ and concentrated. The residue is flash chromatographed on silica gel using 5% MeOH in $CH_2Cl_2$ as the eluent to afford N-(1-naphthyl-methyl)-N-sulfamidoglycine ethyl ester as a clear oil: $[M+1]^+=323$.

C. 5-Naphthalen-1-ylmethyl-1,1-dioxo-1,2,5-thiadiazolidin-3-one

A solution of the title B compound, N-(1-naphthylmethyl)-N-sulfamidoglycine ethyl ester (180 mg, 0.558 mmol) in 5 mL of EtOH is treated with 1N aqueous NaOH (0.67 mL) and the mixture is stirred for 1 h at RT. The resulting precipitate is filtered, washed with EtOH and dried to give 5-naphthalen-1-ylmethyl-1,1-dioxo-1,2,5-thiadiazolidin-3-one as the sodium salt: $[M-1]^-=275$.

EXAMPLE 3

The following examples are prepared analogously to Examples 1 and 2 using appropriately protected starting materials and standard reaction conditions.

| Example | Chemical Name | MS [m/z] |
|---|---|---|
| 3-1 | N-[3-(1,1,4-Trioxo-1,2,5-thiadiazolidin-2-ylmethyl)-benzyl]-acetamide | $[M - 1]^- = 296$ |
| 3-2 | [3-(1,1,4-Trioxo-1,2,5-thiadiazolidin-2-ylmethyl)-benzyl]-carbamic acid t-butyl ester | $[M - 1]^- = 354$ |

| Example | Chemical Name | MS [m/z] |
|---|---|---|
| 3-3 | 5-(4-Aminomethyl-benzyl)-1,1-dioxo-1,2,5-thiadiazolidin-3-one | $[M - 1]^- = 254$ |
| 3-4 | N-[4-(1,1,4-Trioxo-1,2,5-thiadiazolidin-2-ylmethyl)-benzyl]-acetamide | $[M - 1]^- = 296$ |
| 3-5 | [4-(1,1,4-Trioxo-1,2,5-thiadiazolidin-2-ylmethyl)-benzyl]-carbamic acid t-butyl ester | $[M - 1]^- = 354$ |
| 3-6 | 3-Phenyl-N-[4-(1,1,4-trioxo-1,2,5-thiadiazolidin-2-ylmethyl)-benzyl]-propionamide | $[M - 1]^- = 386$ |

Beispiel 1

Beispiel 2

EXAMPLE 4

5-(3-Iodobenzyl)-1,1-dioxo-1,2,5-thiadiazolidin-3-one

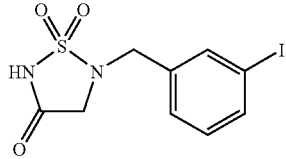

A. N-(3-Iodobenzyl)glycine-N-sulfonic acid amide t-Butanol (0.354 mL, 3.7 mmol) is added dropwise to a stirred solution of chlorosulfonyl isocyanate (0.322 mL, 3.7 mmol) in 46 mL of CH$_2$Cl$_2$ at 0° C. under argon atmosphere. After 1.5 h, a solution of (3-iodo-benzylamino)-acetic acid t-butyl ester (1.07 g, 3.08 mmol) and TEA (1.55 mL, 11.1 mmol) in 46 mL of CH$_2$Cl$_2$ is added. When HPLC of a small aliquot reveals complete disappearance of the amine (less than 2 h) 100 mL of 1N aqueous HCl is added to the reaction. The reaction mixture is extracted with CH$_2$Cl$_2$ (2×100 mL). The combined organic layers are dried by passing through a small column of sodium sulfate (Na$_2$SO$_4$), and evaporated to give a clear oil. This is purified by silica gel chromatography on a 35 g RediSep column with CH$_2$Cl$_2$ as the eluent. The pure fractions are combined and concentrated to give an intermediate product which is dissolved in 6 mL of TFA and stirred for 2 h. The acid is removed by evaporation on a Savant SpeedVac to yield N-(3-iodobenzyl)-glycine-N-sulfonic acid amide as a white solid: $[M-1]^-$ =369.

B. 5-(3-Iodobenzyl)-1,1-dioxo-1,2,5-thiadiazolidin-3-one

A solution of the title A compound, N-(3-iodobenzyl) glycine-N-sulfonic acid amide (459.2 mg, 1.24 mmol) in 12.4 mL of DMF is added dropwise over a period of 10 min to a solution of diisopropyl carbodiimide (0.194 mL, 1.24 mmol) in 12.4 mL of CH$_2$Cl$_2$. After an additional 1.75 h, the reaction mixture is devided into two 40 mL scintillation vials and evaporated down overnight on a Savant SpeedVac system. An attempt at purification using a 35 g RediSep silica gel flash column with 20% EtOAc in hexane to 100% EtOAc gradient over 30 min failed, and the product is recovered from the column by elution with 10% MeOH in CH$_2$Cl$_2$. This material is concentrated and purified via reverse phase HPLC using a gradient from 10% to 90% MeCN in water over 5 min. Fractions containing the clean product are evaporated on a Savant SpeedVac system and 5-(3-iodobenzyl)-1,1-dioxo-1,2,5-thiadiazolidin-3-one is obtained as a white solid: mp=101-103° C.; $[M-1]^-$=351.

Beispiel 1

EXAMPLE 5

5-(3-Nitrobenzyl)-1,1-dioxo-(1,2,5)thiadiazolidin-3-one

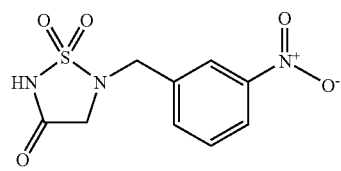

A. 3-Nitrobenzyl sulfamide

A solution of 3-nitrobenzylamine hydrochloride, (1.89 g, 10.0 mmol) in water (10 mL) is treated with NaHCO$_3$ (840 mg, 10.0 mmol) and sulfamide, (960 mg, 10.0 mmol). The mixture is heated at reflux for 5 h. The cooled mixture is acidified to pH 2 with 1N aqueous HCl and the precipitate is filtered, washed with water and dried under vacuum at 50° C. to afford 3-nitrobenzyl sulfamide as a tan solid: $[M-1]^-$= 230.

B. N-(3-Nitrobenzyl)-N-sulfamidoacetic acid methyl ester

Sodium hydride (21 mg, 0.865 mmol) is added to a solution of the title A compound, 3-nitrobenzyl sulfamide in dry DMF (5 mL) under N$_2$ and the mixture is stirred for 20 min. Methyl bromoacetate (132 mg, 0.865 mmol) is added and the mixture is stirred at RT for 4 h. The solvent is evaporated and the residue is partitioned between EtOAc and aqueous saturated aqueous ammonium chloride (NH$_4$Cl) solution. The organic layer is evaporated and the residue is flash chromatographed on silica gel using 3% MeOH in CH$_2$Cl$_2$ as the eluent to afford N-(3-nitrobenzyl)-N-sulfamidoacetic acid methyl ester as a clear oil: $[M-1]^-$= 302.

(a) C. 5-(3-Nitrobenzyl)-1,1-dioxo-1,2,5-thiadiazolidin-3-one

Potassium bis(trimethylsilyl)amide (30 mg, 0.148 mmol) is added to a solution of the title B compound, N-(3-nitrobenzyl)-N-sulfamidoacetic acid methyl ester in dry THF under $N_2$ atmosphere. The mixture is stirred at RT for 16 h, acidified to pH 1 with 1N aqueous HCl and evaporated to dryness. The residue is purified by C8 preparative reverse phase LC-MS chromatography, from 5% to 100% MeCN in water over 13 min, and freeze-dried to afford 5-(3-nitrobenzyl)-1,1-dioxo-1,2,5-thiadiazolidin-3-one as a white solid: $[M-1]^-=270$.

EXAMPLE 6

5-(3-Aminobenzyl)-1,1-dioxo-1,2,5-thiadiazolidin-3-one

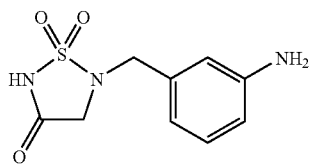

To a solution of the title C compound in Example 5, 5-(3-nitrobenzyl)-1,1-dioxo-1,2,5-thiadiazolidin-3-one (30 mg, 0.11 mmol) in EtOH (5 mL) is added palladium on carbon (10 mg) and the mixture is stirred under 1 atm of hydrogen for 1 h. The catalyst is removed by filtration through a plug of Celite which is washed with MeCN/water (1:1), (20 mL). The solvents are evaporated to afford 5-(3-Aminobenzyl)-1,1-dioxo-1,2,5-thiadiazolidin-3-one as a brown solid: $[M-1]^-=240$.

EXAMPLE 7

N-[3-(1,1,4-Trioxo-1,2,5-thiadiazolidin-2-ylmethyl)phenyl]acetamide

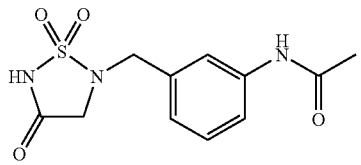

A solution of the title compound of Example 6, 5-(3-aminobenzyl)-1,1-dioxo-1,2,5-thiadiazolidin-3-one (10 mg, 0.041 mmol) in acetic acid (AcOH, 5 mL) is treated with acetic anhydride (85 mg, 0.83 mmol) and stirred at RT for 72 h. The mixture is stirred with water for 2 h, then concentrated to dryness. The crude mixture is purified by LC/MS to afford N-[3-(1,1,4-trioxo-1,2,5-thiadiazolidin-2-ylmethyl)phenyl]acetamide: $[M-1]^-=282$.

(i) EXAMPLE 8

A. Glycine-N-sulfonic acid 4-methoxybenzylamide

Glycine methyl ester-N-sulfonic acid 4-methoxybenzylamide (3.03 g, 10.5 mmol, prepared analogously to literature procedure as described by Ducry, L.; Reinelt, S.; Seiler, P.; Diederich, F. *Helvetica Chimica. Acta.* 1999, 82, 2432-47) is dissolved in 80 mL of 1,4-dioxane, then added 20 mL of water, followed by 21 mL of 1N aqueous NaOH solution. After 40 minutes, the 1,4-dioxane is evaporated, and the remaining aqueous solution is extracted with $Et_2O$. The aqueous solution is acidified with 1N aqueous HCl solution and extracted twice with EtOAc. The organic layer is dried over anhydrous $Na_2SO_4$, filtered and evaporated to dryness giving glycine-N-sulfonic acid 4-methoxybenzylamide: $[M-1]^-=273$.

(ii) B. 2-(4-Methoxybenzyl)-1,1-dioxo-1,2,5-thiadiazolidin-3-one

The title A compound, glycine-N-sulfonic acid 4-methoxybenzylamide (2.51 g, 9.2 mmol) is dissolved in 160 mL of THF, then HOBt (1.41 g, 9.2 mmol) is added and stirred until dissolved. EDCl (1.76 g, 9.2 mmol) is added and stirred for 10 min, followed by the addition of TEA (1.42 mL, 10.2 mmol). The reaction is stirred for 16 h, then concentrated. The residue is partitioned between 1N aqueous HCl and EtOAc. The organic layer is washed with brine and dried over anhydrous $Na_2SO_4$. Filtration followed by evaporation gives an oil which solidifies on standing. This is dissolved in hot EtOAc, concentrated to 20 mL, filtered to remove solids and chromatographed on silica gel with 40% EtOAc in hexanes to afford 2-(4-methoxybenzyl)-1,1-dioxo-1,2,5-thiadiazolidin-3-one as a white solid: mp=111-113° C.; $[M-1]^-=255$.

(iii) C. 2-(4-Methoxybenzyl)-1,1-dioxo-5-pyridin-4-ylmethyl-1,2,5-thiadiazolidin-3-one The title B compound, 2-(4-methoxybenzyl)-1,1-dioxo-1,2,5-thiadiazolidin-3-one (128 mg, 0.5 mmol), 4-hydroxypyridine (109 mg, 1 mmol) and triphenylphosphine (262 mg, 1 mmol) are put into a small reaction vessel under argon and dissolved in 10 mL of THF. This solution is stirred in an ice/water bath and diethyl azodicarboxylate (174 mg, 1 mmol) diluted with an equal volume of THF is added dropwise to the stirred cold solution. The reaction is allowed to stir 16 h while the ice bath slowly warms to RT. The solvent is evaporated on the rotary evaporator, then the residue is taken up in a minimal amount of $CH_2Cl_2$ and chromatographed on a 10 g RediSep silica gel column, using a gradient from 1 to 5% EtOAc in $CH_2Cl_2$ over 15 to 20 min to afford 2-(4-methoxybenzyl)-1,1-dioxo-5-pyridin-4-ylmethyl-1,2,5-thiadiazolidin-3-one: $[M+1]^+=348$.

D. 1,1-Dioxo-5-pyridin-4-ylmethyl-1,2,5-thiadiazolidin-3-one

The title C compound, 2-(4-methoxybenzyl)-1,1-dioxo-5-pyridin-4-ylmethyl-1,2,5-thiadiazolidin-3-one (73 mg, 0.21 mmol) in a mixture of TFA (4.75 mL) and triethylsilane (0.25 mL) in a 20 mL scintillation vial with polyseal cap is heated in an 80° C. oil bath for 16 h. The reaction solvents are removed by overnight evaporation on a Savant SpeedVac system. This gives a white solid which is dissolved in water, filtered through a 0.45 micron PTFE filter disc, and water is removed by lyophilization to give 1,1-dioxo-5-pyridin-4-ylmethyl-1,2,5-thiadiazolidin-3-one TFA salt as an amorphous white solid: $[M+1]^+=228$.

(i) EXAMPLE 9

5-(4-Aminobenzyl)-1,1-dioxo-1,2,5-thiadiazolidin-3-one

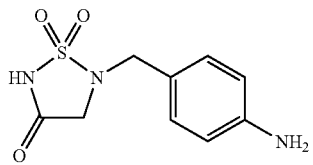

A. Glycine-N-sulfonic acid 2,4-dimethoxybezylamide

Glycine methyl ester-N-sulfonic acid 2,4-dimethoxybenzylamide (14.9 g, 47.0 mmol, prepared analogously to the literature procedure as described by Ducry, L.; Reinelt, S.; Seiler, P.; Diederich, F. *Helvetica Chimica. Acta.* 1999, 82, 2432-47) is dissolved in 100 mL of 1,4-dioxane, then 94 mL of 1N aqueous NaOH solution is added. After 120 min, the 1,4-dioxane is evaporated on the rotary evaporator, and the remaining aqueous solution is extracted with $Et_2O$. The aqueous solution is acidified with 1N aqueous HCl and extracted with EtOAc. The organic layer is dried over anhydrous $MgSO_4$, filtered and evaporated to dryness giving glycine-N-sulfonic acid 2,4-dimethoxybenzylamide: $[M-1]^- =303$.

B. 2-(2,4-Dimethoxybenzyl)-1,1-dioxo-1,2,5-thiadiazolidin-3-one

The title A compound, glycine-N-sulfonic acid 2,4-dimethoxybenzylamide (14.3 g, 47.0 mmol) is dissolved in 300 mL of THF, then HOBt (7.20 g, 47.0 mmol) is added as a solid and stirred until dissolved. EDCl (9.01 g, 47.0 mmol) is added as a solid and stirred for 10 min, followed by the addition of TEA (7.20 mL, 51.7 mmol). The reaction is stirred for 16 h, then concentrated. The residue is partitioned between 1N aqueous HCl and EtOAc, and the organic layer is dried over anhydrous $MgSO_4$. Filtration followed by evaporation gives an oil which solidifies on standing. This is dissolved in hot EtOAc and flash chromatographed on silica gel with 40% EtOAc in hexanes to afford 2-(2,4-dimethoxybenzyl)-1,1-dioxo-1,2,5thiadiazolidin-3-one as a white solid: $[M-1]^- =285$.

C. 4-[5-(2,4-Dimethoxybenzyl)-1,1,4-trioxo-1,2,5-thiadiazolidin-2-ylmethyl]phenyl}-carbamic acid t-butyl ester The title B compound, 2-(2,4-dimethoxybenzyl)-1,1-dioxo-1,2,5-thiadiazolidin-3-one (98 mg, 0.34 mmol) and (4-hydroxymethylphenyl)carbamic acid t-butyl ester (153 mg, 0.68 mmol) and triphenylphosphine (180 mg, 0.68 mmol) are dissolved in THF (10 mL) with stirring under argon atmosphere. The reaction is cooled in an ice/water bath and diethyl azodicarboxylate (0.107 mL, 0.68 mmol) dissolved in THF (0.107 mL) is added dropwise. After 16 h, the solvent is evaporated and the residue is taken up in a minimal amount of $CH_2Cl_2$ and chromatographed on silica gel with a gradient from 1 to 5% EtOAc in $CH_2Cl_2$ over 15 min to give {4-[5-(2,4-dimethoxybenzyl)-1,1,4-trioxo-1,2,5-thiadiazolidin-2-ylmethyl]-phenyl}-carbamic acid t-butyl ester as an oil: $[M+NH_4]^+ =509$.

(iv) D. 5-(4-Aminobenzyl)-1,1-dioxo-1,2,5-thiadiazolidin-3-one

To a solution of the title C compound, {4-[5-(2,4-dimethoxybenzyl)-1,1,4-trioxo-1,2,5-thiadiazolidin-2-ylmethyl]phenyl}carbamic acid t-butyl ester (20 mg, 0.041 mmol) in $CH_2Cl_2$ (1 mL) is added TFA (1 mL). The reaction is stirred at RT overnight. Upon addition the reaction becomes light pink colored, progressing to deep purple after overnight. The solvent is evaporated and the residue is taken up in 2 mL of MeCN/water (50/50). This is filtered through a 0.2 micron PTFE membrane filter and the filtrate is collected. MeCN is removed under reduced pressure and water via lyophilization to give 5-(4-amino-benzyl)-1,1-dioxo-1,2,5-thiadiazolidin-3-one TFA salt as a yellow foam: $[M-1]^- =240$.

EXAMPLE 10

The following examples are prepared analogously to Examples 8 and 9 using appropriately protected starting materials and standard reaction conditions.

| Example | Chemical Name | MS [m/z] |
| --- | --- | --- |
| 10-1 | N-[3-(1,1,4-Trioxo-1,2,5-thiadiazolidin-2-ylmethyl)-phenyl]-butyramide | $[M - 1]^- = 310$ |
| 10-2 | 1-Propyl-3-[3-(1,1,4-trioxo-1,2,5-thiadiazolidin-2-ylmethyl)-phenyl]-urea | $[M - 1]^- = 325$ |
| 10-3 | 4-(1,1,4-Trioxo-1,2,5-thiadiazolidin-2-ylmethyl)-benzoic acid methyl ester | $[M - 1]^- = 283$ |
| 10-4 | 4-(1,1,4-Trioxo-1,2,5-thiadiazolidin-2-ylmethyl)-benzoic acid | $[M - 1]^- = 269$ |
| 10-5 | 2-(1,1,4-Trioxo-1,2,5-thiadiazolidin-2-ylmethyl)-benzoic acid | $[M - 1]^- = 269$ |
| 10-6 | 5-(2-Methyl-benzyl)-1,1-dioxo-1,2,5-thiadiazolidin-3-one | $[M - 1]^- = 239$ |
| 10-7 | 1,1-Dioxo-5-pyridin-3-ylmethyl-1,2,5-thiadiazolidin-3-one | $[M - 1]^- = 226$ |
| 10-8 | 1,1-Dioxo-5-pyridin-2-ylmethyl-1,2,5-thiadiazolidin-3-one | $[M - 1]^- = 226$ |
| 10-9 | 5-(6-Amino-pyridin-3-ylmethyl)-1,1-dioxo-1,2,5-thiadiazolidin-3-one | $[M - 1]^- = 241$ |
| 10-10 | 1,1-Dioxo-5-thiophen-2-ylmethyl-1,2,5-thiadiazolidin-3-one | $[M - 1]^- = 231$ |
| 10-11 | 5-(4-Methoxy-benzyl)-1,1-dioxo-1,2,5-thiadiazolidin-3-one | $[M - 1]^- = 255$ |
| 10-12 | 5-(4-Amino-2-bromo-benzyl)-1,1-dioxo-1,2,5-thiadiazolidin-3-one | $[M - 1]^- = 318$ |
| 10-13 | N-[4-(1,1,4-Trioxo-1,2,5-thiadiazolidin-2-ylmethyl)-phenyl]-acetamide | $[M - 1]^- = 282$ |

-continued

| Example | Chemical Name | MS [m/z] |
|---|---|---|
| 10-14 | N-[4-(1,1,4-Trioxo-1,2,5-thiadiazolidin-2-ylmethyl)-phenyl]-methanesulfonamide | [M − 1]⁻ = 318 |
| 10-15 | N-[4-(1,1,4-Trioxo-1,2,5-thiadiazolidin-2-ylmethyl)-benzyl]-methanesulfonamide | [M − 1]⁻ = 332 |
| 10-16 | 5-(4-Methyl-benzyl)-1,1-dioxo-1,2,5-thiadiazolidin-3-one | [M − 1]⁻ = 239 |
| 10-17 | Amino-[4-(1,1,4-trioxo-1,2,5-thiadiazolidin-2-ylmethyl)-phenyl]-acetic acid | [M − 1]⁻ = 298 |
| 10-18 | 2-Amino-N-propyl-2-[2-(1,1,4-trioxo-1,2,5-thiadiazolidin-2-ylmethyl)-phenyl]-acetamide | [M − 1]⁻ = 339 |
| 10-19 | 2-Amino-N-propyl-2-[4-(1,1,4-trioxo-1,2,5-thiadiazolidin-2-ylmethyl)-phenyl]-acetamide | [M − 1]⁻ = 339 |
| 10-20 | 2,2,2-Trifluoro-N-{propylcarbamoyl-[4-(1,1,4-trioxo-1,2,5-thiadiazolidin-2-ylmethyl)-phenyl]-methyl}-acetamide | [M − 1]⁻ = 435 |
| 10-21 | 2-Methanesulfonylamino-N-propyl-2-[4-(1,1,4-trioxo-1,2,5-thiadiazolidin-2-ylmethyl)-phenyl]-acetamide | [M − 1]⁻ = 417 |
| 10-22 | 2-Acetylamino-N-propyl-3-[4-(1,1,4-trioxo-1,2,5-thiadiazolidin-2-ylmethyl)-phenyl]-propionamide | [M + H]+ = 397 |
| 10-23 | 2-Acetylamino-2-[4-(1,1,4-trioxo-1,2,5-thiadiazolidin-2-ylmethyl)-benzyl]-malonic acid diethyl ester | (mp = 197° C.) |
| 10-24 | 2-Amino-N-propyl-3-[4-(1,1,4-trioxo-1,2,5-thiadiazolidin-2-ylmethyl)-phenyl]-propionamide | [M − 1]⁻ = 353 |
| 10-25 | 2-Acetylamino-3-[4-(1,1,4-trioxo-1,2,5-thiadiazolidin-2-ylmethyl)-phenyl]-propionic acid ethyl ester | [M − 1]⁻ = 382 |
| 10-26 | Phenyl-(1,1,4-trioxo-1,2,5-thiadiazolidin-2-yl)-acetic acid | [M − 1]⁻ = 269 |
| 10-27 | 1,1-Dioxo-5-phenethyl-1,2,5-thiadiazolidin-3-one | [M − 1]⁻ = 239 |
| 10-28 | 5-[2-(4-Methyl-thiazol-5-yl)-ethyl]-1,1-dioxo-1,2,5-thiadiazolidin-3-one | [M − 1]⁻ = 260 |
| 10-29 | 5-[2-(3,4-Dimethoxy-phenyl)-ethyl]-1,1-dioxo-1,2,5-thiadiazolidin-3-one | [M − 1]⁻ = 299 |
| 10-30 | 5-[2-(2-Chloro-phenyl)-ethyl]-1,1-dioxo-1,2,5-thiadiazolidin-3-one | [M − 1]⁻ = 273 |
| 10-31 | 5-[2-(4-Amino-phenyl)-ethyl]-1,1-dioxo-1,2,5-thiadiazolidin-3-one | [M − 1]⁻ = 254 |
| 10-32 | 2,2,2-Trifluoro-N-{4-[2-(1,1,4-trioxo-1,2,5-thiadiazolidin-2-yl)-ethyl]-phenyl}-acetamide | [M − 1]⁻ = 350 |
| 10-33 | N-{4-[2-(1,1,4-Trioxo-1,2,5-thiadiazolidin-2-yl)-ethyl]-phenyl}-butyramide | [M − 1]⁻ = 324 |
| 10-34 | 1,1-Dioxo-5-(2-pyridin-3-yl-ethyl)-1,2,5-thiadiazolidin-3-one | [M − 1]⁻ = 240 |
| 10-35 | 1,1-Dioxo-5-(2-pyridin-4-yl-ethyl)-1,2,5-thiadiazolidin-3-one | [M − 1]⁻ = 240 |
| 10-36 | 3-Phenyl-2-(1,1,4-trioxo-1,2,5-thiadiazolidin-2-yl)-propionic acid | [M − 1]⁻ = 283 |
| 10-37 | 5-[2-(3-Amino-phenyl)-ethyl]-1,1-dioxo-1,2,5-thiadiazolidin-3-one | [M − 1]⁻ = 254 |
| 10-38 | 5-(4-Aminomethyl-naphthalen-1-ylmethyl)-1,1-dioxo-1,2,5-thiadiazolidin-3-one | [M − 1]⁻ = 304 |

EXAMPLE 11

5-(1-Ethyl-2-methyl-1H-benzoimidazol-5-ylmethyl)-1,1-dioxo-1-1,2,5-thiadiazolidin-3-one

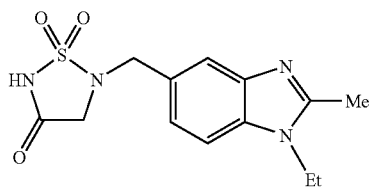

A. 4-Ethylamino-3-nitro-benzoic acid

To a suspension of 1.85 g of 4-fluoro-3-nitrobenzoic acid (10 mmol) in 25 mL of MeOH is added 20 mL of ethylamine (2.0M in THF). The resulting yellow solution is stirred at 75° C. for 5 h then at RT for 48 h. The solvent is removed under reduced pressure, then water is added to the residue. The resulting orange suspension is acidified with 2N aqueous HCl and the yellow precipitate is collected by filtration, washed with water and dried in vacuo to give 4-ethylamino-3-nitro-benzoic acid: mp=233-236° C.; ¹H-NMR (DMSO-d₆) δ 12.83 (s, 1H), 8.61 (d, J=1.84, 1H), 8.49 (m, 1H), 7.97 (dd, 1H), 7.12 (d, J=9.2, 1H), 3.46 (m, 2H), 1.23 (t, 3H); [M−1]⁻=209.

B. 3-Amino-4-ethylamino-benzoic acid

A solution of 1.56 g (7.4 mmol) of the title A compound 4-ethylamino-3-nitro-benzoic acid in 60 mL of THF/water (2:1) is hydrogenated at 20 psi over 300 mg of Raney nickel for 18 h. The catalyst is removed by filtration through Celite and the solvent is removed under reduced pressure to give 3-amino-4-ethylamino-benzoic acid as a dark solid. This material is used as such in the next step.

C. 1-Ethyl-2-methyl-1H-benzoimidazole-5-carboxylic acid

A mixture of 1.4 g (7.7 mmol) of the title B compound, 3-amino-4-ethylamino-benzoic acid and 15 mL (104 mmol)

of triethyl orthoacetate in 20 mL of EtOH is refluxed for 7 h. The reaction mixture is allowed to cool to RT and the precipitated solid is collected by filtration, washed with EtOH (2×), then with methyl-t-butylether (MTBE) and dried in vacuo to give 1-ethyl-2-methyl-1H-benzoimidazole-5-carboxylic acid as a grey solid: mp>250° C.; $^1$H-NMR (DMSO-d$_6$) δ 12.65 (s, 1H), 8.11 (s, 1H), 7.82 (dd, 1H), 7.59 (d, J=8.46, 1H), 4.26 (q, 2H), 2.57 (s, 3H), 1.30 (t, 3H); [M−1]$^−$=203.

D. 1-Ethyl-2-methyl-1H-benzoimidazole-5-carboxylic acid methyl ester

To a suspension of 1.1 g (5.4 mmol) of the title C compound, 1-ethyl-2-methyl-1H-benzoimidazole-5-carboxylic acid in 25 mL of MeOH is added dropwise 0.7 g (5.9 mmol) of thionyl chloride and the resulting solution is stirred at 70° for 6 h, then at RT for 18 h. The solvent is removed under reduced pressure and 8% aqueous NaHCO$_3$ solution is added to the residue. The mixture is extracted with EtOAc and the organic phase is dried over anhydrous Na$_2$SO$_4$. The organic solution is concentrated until the product precipitated. The solid is collected by filtration, washed with EtOH and MTBE to give 1-ethyl-2-methyl-1H-benzoimidazole-5-carboxylic acid methyl ester as a beige solid: mp=118-121° C.; IR (KBr) 3430, 1695 cm$^{-1}$; $^1$H-NMR (CDCl$_3$) δ 8.39 (s, 1H), 7.98 (dd, 1H), 7.32 (d, J=8.45, 1H), 4.19 (q, 2H), 3.94 (s, 3H), 2.64 (s, 3H), 1.43 (t, 3H); [M+1]$^+$=219.

E. (1-Ethyl-2-methyl-1H-benzoimidazol-5-yl)-methanol

To a solution of 450 mg (2.06 mmol) of the title D compound, 1-ethyl-2-methyl-1H-benzoimidazole-5-carboxylic acid methyl ester in 5 mL of THF is added dropwise 2.1 mL (2.1 mmol) of lithium aluminum hydride (LAH, 1.0M in THF). The mixture is stirred at RT for 90 min, then saturated aqueous sodium sulfate solution is carefully added dropwise until a thick precipitate formed. MTBE is added to the mixture and the insoluble aluminum salts are removed by filtration through Celite. The solvent is removed under reduced pressure to give (1-ethyl-2-methyl-1H-benzoimidazol-5-yl)-methanol as an oil: $^1$H-NMR (CDCl$_3$) δ 7.63 (s, 1H), 7.28 (m, 2H), 4.77 (s, 2H), 4.16 (q, 2H), 3.74 (t, broad, 1H), 2.60 (s, 3H), 1.40 (t, 3H); [M+1]$^+$=191.

F. 2-(2,4-Dimethoxy-benzyl)-5-(1-ethyl-2-methyl-1H-benzoimidazol-5-ylmethyl)-1,1-dioxo-1-1,2,5-thiadiazolidin-3-one To a solution of 767 mg (2.7 mmol) of the title B compound in Example 9, 2-(2,4-dimethoxybenzyl)-1,1-dioxo-1,2,5-thiadiazolidin-3-one, 340 mg (1.8 mmol) of the title E compound, (1-ethyl-2-methyl-1H-benzoimidazol-5-yl)-methanol and 545 mg (2.7 mmol) of tri-n-butylphosphine in 20 mL of THF is added 460 mg (2.7 mmol) of N,N,N',N'-tetramethyl-azodicarboxamide (TMAD). The mixture is stirred at RT for 24 h, and the resulting precipitate is filtered and washed with a small volume of THF. The filtrate is evaporated to give an oil which is chromatographed using 5% EtOH in EtOAc to afford 2-(2,4-dimethoxy-benzyl)-5-(1-ethyl-2-methyl-1H-benzoimidazol-5-ylmethyl)-1,1-dioxo-1-1,2,5-thiadiazolidin-3-one as a solid: $^1$H-NMR (CDCl$_3$) δ 7.61 (s, 1H), 7.31-7.20 (m, 3H), 6.46 (m, 2H), 4.79 (s, 2H), 4.44 (s, 2H), 4.17 (q, 2H), 3.84 (s, 3H), 3.80 (s, 3H), 3.73 (s, 2H), 2.61 (s, 3H), 1.41 (t, 3H); [M+1]$^+$=459.

G. 5-(1-Ethyl-2-methyl-1H-benzoimidazol-5-ylmethyl)-1,1-dioxo-1-1,2,5-thiadiazolidin-3-one A solution of 200 mg (0.44 mmol) of the title F compound, 2-(2,4-dimethoxy-benzyl)-5-(1-ethyl-2-methyl-1H-benzoimidazol-5-ylmethyl)-1,1-dioxo-1-1,2,5-thiadiazolidin-3-one in 4 mL of TFA/CH$_2$Cl$_2$ (1:1) is stirred at RT for 90 min. The solvent is removed from the purple solution and 4 mL of MeCN/water (1:1) is added. After stirring the mixture for 30 min, the mixture is centrifuged and the supernatant is decanted. The solvent is removed under reduced pressure and the residue is chromatographed by preparative HPLC (gradient: 10% MeCN/water→100% MeCN, each containing 0.1% TFA). The proper fractions are combined and lyophylized to give 5-(1-ethyl-2-methyl-1H-benzoimidazol-5-ylmethyl)-1,1-dioxo-1-1,2,5-thiadiazolidin-3-one TFA salt as an amorphous solid: mp=255-265° C.; $^1$H-NMR (DMSO-d$_6$) δ 7.91 (d, J=8.29, 1H), 7.77 (s, 1H), 7.56 (d, J=8.67, 1H), 4.44 (q, 2H), 4.27 (s, 2H), 3.47 (s, 2H), 2.82 (s, 3H), 1.39 (t, 3H); [M−1]$^−$=307.

EXAMPLE 12

5-[2-Methyl-1-(3-methyl-butyl)-1H-benzoimidazol-5-ylmethyl]-1,1-dioxo-1-1,2,5-thiadiazolidin-3-one

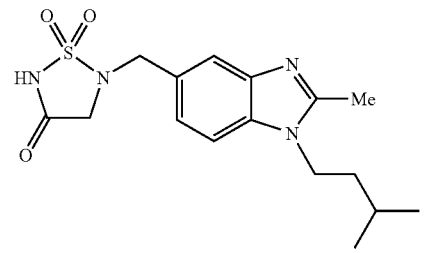

The title compound is prepared analogously to Example 11: mp=70-75° C.; $^1$H-NMR (DMSO-d$_6$) δ 7.91 (d, J=8.46, 1H), 7.78 (s, 1H), 7.57 (dd, 1H), 4.40 (m, 2H), 4.33 (s, 2H), 3.63 (s, 2H), 2.83 (s, 3H), 1.78-1.60 (m, 3H), 0.98 (d, J=5.88, 6H); [M−1]$^−$=349.

EXAMPLE 13

5-(4-Methoxy-quinolin-7-ylmethyl)-1,1-dioxo-1,2,5-thiadiazolidin-3-one

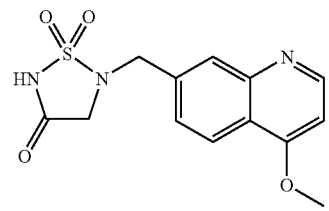

A. 4-Chloro-7-trifluoromethylquinoline 1.0 g (4.32 mmols) of 4-chloro-7-trifluoromethylquinoline in 20 mL of 80% sulfuric acid in a sealed tube is heated to 200° C. for 18 h. The tube is cooled to RT, vented, and poured into 200 mL water, which is made basic with sodium hydroxide to pH 3-4. The resulting solid is filtered and washed with water, then dissolved in 100 mL 1N aqueous NaOH, filtered to remove insolubles, and extracted with EtOAc. The aqueous solution is acidified with 1N aqueous HCl to pH 3-4, filtered, and the collected solid washed with water. The solid is dried to give 4-chloro-7-trifluoromethylquinoline: $^1$H-NMR (DMSO-d$_6$) δ 7.90 (1H, d, J=4.8), 8.22 (1H, dd, J=8.7, 1.5), 8.32 (1H, d, J=8.7), 8.63 (1H, d, J=1.5), 8.96 (1H, d, J=4.8), 13.7 (1H, br s).

B. 7-Carbomethoxy-4-methoxyquinoline 606 mg (2.92 mmol) of the title A compound, 4-chloro-7-quinoline carboxylic acid in 50 mL MeOH is saturated with HCl gas, then heated at 60° C. for 18 h. The solvent is removed on a rotary evaporator, and the residue taken up in water, made basic with NaHCO$_3$, and extracted twice with EtOAc. Combined organic fractions are dried over anhydrous MgSO$_4$, filtered, and the solvent is removed to afford the crude product. This is chromatographed on a Biotage 40M column with 98:2 EtOAc/EtOH to give 7-carbomethoxy-4-methoxyquinoline: mp=147-148° C.; $^1$H-NMR (CDCl$_3$) δ 4.00 (3H, s), 4.08 (3H, s), 6.81 (1H, d, J=5.2), 8.10 (1H, dd, J=8.7, 1.5), 8.26 (1H, d, J=8.7), 8.75 (1H, d, J=1.5), 8.83 (1H, d, J=5.2); [M+1]$^+$=218.

C. (4-Methoxy-quinolin-7-yl)-methanol

A solution of 2 mL of 1 M LAH (2 mmol) in 25 mL THF is cooled in an ice bath. 450 mg (2.07 mmol) of the title B compound, 7-carbomethoxy-4-methoxyquinoline suspended in 15 mL THF is added and allowed to stir at RT for 18 h. The mixture is quenched with saturated aqueous Na$_2$SO$_4$, filtered, and the filtrate dried over anhydrous MgSO$_4$, filtered, and solvent removed to give (4-methoxyquinolin-7-yl)-methanol: $^1$H-NMR (CDCl$_3$) δ 4.04 (3H, s), 4.89 (2H, s), 6.72 (1H, d, J=5.3), 7.51 (1H, d, J=8.5), 8.04 (1H, s), 8.16 (1H, d, J=8.5), 8.72 (1H, d, J=5.3).

D. 2-(2,4-Dimethoxy-benzyl)-5-(4-methoxy-quinolin-7-ylmethyl)-1,1-dioxo-1,2,5-thiadiazolidin-3-one 745 mg (2.60 mmol) of the title B compound in Example 9, 2-(2,4-dimethoxybenzyl)-1,1-dioxo-1,2,5-thiadiazolidin-3-one, 328 mg (1.73 mmol) of the title E compound, (4-methoxyquinoline-7-yl)-methanol and 448 mg (526 mg., 2.60 mmol) of tributylphosphine are stirred in 5 mL of THF. 448 mg (2.60 mmols) of TMAD is added and the mixture is stirred for 18 h. A spatula tip of Raney nickel is added, the mixture is stirred for 10 min, and then filtered through Celite. The filtrate is evaporated to dryness and chromatographed on a Biotage 40M column with 98:2 EtOAc/EtOH to afford 2-(2,4-dimethoxy-benzyl)-5-(4-methoxy-quinolin-7-ylmethyl)-1,1-dioxo-1,2,5-thiadiazolidin-3-one: mp=128-132° C.; $^1$H-NMR (CDCl$_3$) δ 3.79 (2H, s), 3.81 (3H, s), 3.85 (3H, s), 4.06 (3H, s), 4.51 (2H, s), 4.82 (2H, s), 6.46 (2H, m), 6.78 (1H, d, J=5.2) 7.30 (1H, m), 7.53 (1H, dd, J=8.5, 1.5), 7.96 (1H, s), 8.22 (1H, d J=8.5), 8.77 (1H, d, J=5.2); [M+1]$^+$=458.

E. 5-(4-Methoxy-quinolin-7-ylmethyl)-1,1-dioxo-1,2,5-thiadiazolidin-3-one 210 mg (459 μmol) of the title D compound, 2-(2,4-dimethoxy-benzyl)-5-(4-methoxy-quinolin-7-ylmethyl)-1,1-dioxo-1,2,5-thiadiazolidin-3-one are stirred for 30 min in 4 mL of 1:1 TFA/CH$_2$Cl$_2$. The solvent is removed on a rotary evaporator and the residue triturated with 4 mL of 1:1 MeCN/water. This mixture is filtered through a 0.2 micron disk and the solvent is removed. The resulting material is purified by preparative LC/MS, and the collected product fractions are lyophilized to give 5-(4-methoxy-quinolin-7-ylmethyl)-1,1-dioxo-1,2,5-thiadiazolidin-3-one: [M−1]$^-$=306.

EXAMPLE 14

5-(4-Isobutoxy-quinolin-7-ylmethyl)-1,1-dioxo-1,2,5-thiadiazolidin-3-one

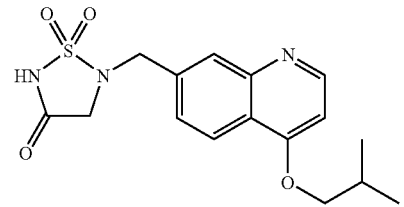

The title compound is prepared analogously to Example 13: $^1$H-NMR (DMSO-d$_6$) δ1.10 (3H, d, J=6.6), 2.27 (1H, m, J=6.6), 3.66 (2H, s), 4.34 (2H, d, J=6.6), 4.46 (2H, s), 7.55 (1H, d, J=6.8), 7.86 (1H, dd, J=8.6, 1.1), 8.14 (1H, s), 8.37 (1H, d, J=8.6), 9.15 (1H, d, J=6.8); [M+1]$^+$=350, [M−1]$^-$=348.

EXAMPLE 15

N-(Butylcarbamoyl-phenyl-methyl)-N-(4-(1,1,4-trioxo-1,2,5-thiazodiazolidin-2-ylmethyl)-benzoyl)-amino-acetic acid

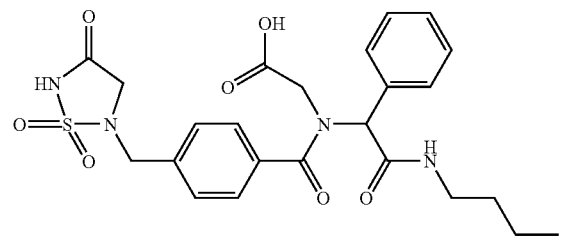

A. 4-[5-(2,4-Dimethoxy-benzyl)-1,1,4-trioxo-1,2,5-thiadiazolidin-2-yl methyl]-benzoic acid To a suspension of the title B compound in Example 9, 2-(2,4-dimethoxy-benzyl)-1,1-dioxo-1,2,5-thiadiazolidin-3-one (13.87 g, 48.4 mmol) and 4-bromomethylbenzoic acid (10.42 g, 48.4 mmol) in CH$_2$Cl$_2$ (150 mL) is added DBU (14.5 mL, 96.9 mmol) at once and the mixture is stirred at RT overnight. The reaction mixture is washed two times with 1N aqueous HCl, one time with brine, then dried over anhydrous MgSO$_4$ and concentrated to a small volume to crystallize the product. The solid is collected by filtration, washed with ethyl ether and dried under high vacuum to afford 4-[5-(2,4-dimethoxy-benzyl)-1,1,4-trioxo-1,2,5-thiadiazolidin-2-ylmethyl]-benzoic acid: mp=175-177° C.; [M−1]⁻=419.

B. N-(Butylcarbamoyl-phenylmethyl)-N-(4-(1,1,4-trioxo-1,2,5-thiazodiazolidin-2-ylmethyl)-benzoyl)-amino-acetic acid Wang resin (100-200 mesh, 1.11 mmol/g substitution, 3.41 g, 3.78 mmol) is suspended in pyridine (25 mL) and the mixture is shaken for 15 min and drained. The resin is resuspended in pyridine (30 mL), Fmoc-glycine (4.5 g, 15.1 mmol), 4-dimethylamino-pyridine (DMAP, 46 mg, 0.378 mmol) and N,N'-dicyclohexylcarbonylcarbodiimide (3.12 g, 15.1 mmol) are added and the mixture is shaken overnight. The resin is drained and washed successively with DMF (20 mL, 3 times), MeOH (20 mL, 2 times), THF (20 mL, 1 time) and alternatively with CH$_2$Cl$_2$ (20 mL, 3 times) and MeOH (20 mL, 2 times). The resin is dried under high vacuum overnight. The dry Wang resin-Fmoc-glycine ester (140 mg, 0.106 mmol) is treated with 20% piperidine in CH$_2$Cl$_2$ (3 mL, 15 min, 2 times) and washed alternatively with CH$_2$Cl$_2$ (3 mL, 2 times) and MeOH (3 mL, 2 times) and again with CH$_2$Cl$_2$ (3 mL, 2 times). The resin is then suspended in CH$_2$Cl$_2$—MeOH (1:1, 4 mL), and the title A compound, 4-[5-(2,4-dimethoxy-benzyl)-1,1,4-trioxo-1,2,5-thiadiazolidin-2-ylmethyl]-benzoic acid (133 mg, 0.317 mmol), benzaldehyde (32 μl, 0.317 mmol) and butylisonitrile (33 μl, 0.317 mmol) are added and the mixture is shaken for 48 h. The resin is drained and is washed alternatively with CH$_2$Cl$_2$ (4 mL, 2 times), MeOH (4 mL, 2 times) and again with CH$_2$Cl$_2$ (4 mL, 2 times). The resin is then shaken with CH$_2$Cl$_2$-TFA (1:1, 4 mL) for 4 h and drained into a receiving flask. The resin is washed with CH$_2$Cl$_2$-TFA (1:1, 4 mL) and drained into the same receiving flask. The solvents are evaporated to dryness under a stream of nitrogen and the residue is further dried under high vacuum. The residue is purified using a Micromass LC/MS system (Phenominex Luna 5μ, 60×21.2 mm C-8 column, 5 to 100 gradient over 8 min, A=water/0.1% TFA, B=MeCN/0.1% TFA, 20 mL/min flow rate). The fractions containing the product are pooled and evaporated to a small volume which is subsequently lyophilized to give N-(butylcarbamoyl-phenyl-methyl)-N-(4-(1,1,4-trioxo-1,2,5-thiazodiazolidin-2-ylmethyl)-benzoyl)-amino-acetic acid as a foam: [M−1]⁻=515.

EXAMPLE 16

The following examples are prepared analogously to Example 15 by replacing benzaldehyde with the appropriate aldehyde as a starting material.

| Example | Chemical Name | MS [m/z] |
|---|---|---|
| 16-1 | {[Butylcarbamoyl-(4-ethyl-phenyl)-methyl]-[4-(1,1,4-trioxo-1,2,5-thiadiazolidin-2-ylmethyl)-benzoyl]-amino}-acetic acid | [M − 1]⁻ = 543 |
| 16-2 | {[Butylcarbamoyl-(3-phenoxy-phenyl)-methyl]-[4-(1,1,4-trioxo-1,2,5-thiadiazolidin-2-ylmethyl)-benzoyl]-amino}-acetic acid | [M − 1]⁻ = 607 |
| 16-3 | {[Butylcarbamoyl-(4-methoxy-phenyl)-methyl]-[4-(1,1,4-trioxo-1,2,5-thiadiazolidin-2-ylmethyl)-benzoyl]-amino}-acetic acid | [M − 1]⁻ = 545 |
| 16-4 | {[(2-Bromo-phenyl)-butylcarbamoyl-methyl]-[4-(1,1,4-trioxo-1,2,5-thiadiazolidin-2-ylmethyl)-benzoyl]-amino}-acetic acid | [M − 1]⁻ = 593, 595 |
| 16-5 | {(Butylcarbamoyl-naphthalen-2-yl-methyl)-[4-(1,1,4-trioxo-1,2,5-thiadiazolidin-2-ylmethyl)-benzoyl]-amino}-acetic acid | [M − 1]⁻ = 565 |
| 16-6 | {[Butylcarbamoyl-(4-chloro-phenyl)-methyl]-[4-(1,1,4-trioxo-1,2,5-thiadiazolidin-2-ylmethyl)-benzoyl]-amino}-acetic acid | [M − 1]⁻ = 549, 551 |
| 16-7 | {[(3-Benzyloxy-phenyl)-butylcarbamoyl-methyl]-[4-(1,1,4-trioxo-1,2,5-thiadiazolidin-2-ylmethyl)-benzoyl]-amino}-acetic acid | [M − 1]⁻ = 621 |
| 16-8 | {((E)-1-Butylcarbamoyl-3-phenyl-allyl)-[4-(1,1,4-trioxo-1,2,5-thiadiazolidin-2-ylmethyl)-benzoyl]-amino}-acetic acid | [M − 1]⁻ = 541 |
| 16-9 | N-(1-Butylcarbamoyl-3-phenyl-propyl)-N-(4-(1,1,4-trioxo-1,2,5-thiazodiazolidin-2-ylmethyl)-benzoyl)-amino-acetic acid | [M − 1]⁻ = 543 |

EXAMPLE 17

4-(1,1,4-Trioxo-1,2,5-thiadiazolidin-2-ylmethyl) benzoic acid 4-methanesulfonyl-benzyl ester

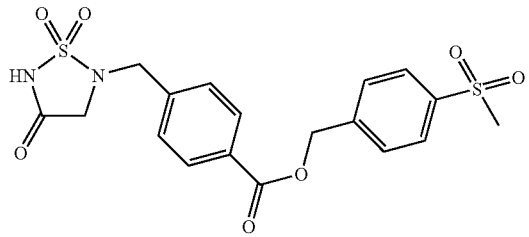

A. 4-[5-(2,4-Dimethoxy-benzyl)-1,1,4-trioxo-1,2,5-thiadiazolidin-2-ylmethyl]-benzoic acid To a suspension of the title B compound in Example 9, 2-(2,4-dimethoxy-benzyl)-1,1-dioxo-1,2,5-thiadiazolidin-3-one, (13.87 g, 48.4 mmol) and 4-bromomethylbenzoic acid (10.42 g, 48.4 mmol) in CH$_2$Cl$_2$ (150 mL), DBU (14.5 mL, 96.9 mmol) is added at once and the mixture is stirred at RT overnight. The reaction mixture is washed with 1N aqueous HCl, and brine, dried over anhydrous MgSO$_4$ and evaporated to a small volume to crystallize the product. The solid is collected by filtration, washed with ethyl ether and dried under high vacuum to afford 4-[5-(2,4-dimethoxy-benzyl)-

1,1,4-trioxo-1,2,5-thiadiazolidin-2-ylmethyl]-benzoic acid: mp=175-177° C.; [M-1]⁻=419.

B. 4-[5-(2,4-Dimethoxy-benzyl)-1,1,4-trioxo-1,2,5-thiadiazolidin-2-ylmethyl]-benzoyl chloride 1.66 g (3.47 mmols) of the title A compound, 4-[5-(2,4-dimethoxy-benzyl)-1,1,4-trioxo-1,2,5-thiadiazolidin-2-ylmethyl]-benzoic acid and 2.5 mL (34 mmol) of $SOCl_2$ in 40 mL toluene are heated at 110° C. until only a small amount of dark solid remained undissolved. The solution is filtered and the solvent is removed on a rotary evaporator and the residual dark purple solid is dried in a vacuum oven overnight to give 4-[5-(2,4-dimethoxy-benzyl)-1,1,4-trioxo-1,2,5-thiadiazolidin-2-ylmethyl]-benzoyl chloride which is used as such without further purification.

C. 4-[5-(2,4-Dimethoxy-benzyl-1,1,4-trioxo-1,2,5-thiadiazolidin-2-ylmethyl]-benzoic acid 4-methylsulfanyl-benzyl ester 400 mg (911 μmol) of the title B compound, 4-[5-(2,4-dimethoxy-benzyl)-1,1,4-trioxo-1,2,5-thiadiazolidin-2-ylmethyl]-benzoyl chloride, 140 μL (1.0 mmol) of TEA and 141 mg (914 μmol) of 4-(methylthio)benzyl alcohol in 10 mL of $CH_2Cl_2$ are stirred at RT for 18 h. The solvent is removed under reduced pressure and the residue is chromatographed on a Biotage 40M column with 98/2 —$CH_2Cl_2$/EtOAc to give 4-[5-(2,4-dimethoxy-benzyl)-1,1,4-trioxo-1,2,5-thiadiazolidin-2-ylmethyl]-benzoic acid 4-methylsulfanyl-benzyl ester: $[M+NH_4]^+$=574.

D. 4-[5-(2,4-Dimethoxy-benzyl-1,1,4-trioxo-1,2,5-thiadiazolidin-2-ylmethyl]-benzoic acid 4-methanesulfonyl-benzyl ester 150 mg (270 μmol) of the title C compound, 4-[5-(2,4-dimethoxy-benzyl)-1,1,4-trioxo-1,2,5-thiadiazolidin-2-ylmethyl]-benzoic acid 4-methylsulfanyl-benzyl ester and 181 mg (810 μmols) of 81% m-chloroperbenzoic acid are stirred overnight in 10 mL of $CH_2Cl_2$. The solution is washed with saturated aqueous $NaHCO_3$, then dried, filtered, and solvent removed to afford 4-[5-(2,4-dimethoxy-benzyl)-1,1,4-trioxo-1,2,5-thiadiazolidin-2-ylmethyl]-benzoic acid 4-methanesulfonyl-benzyl ester: $[M+NH_4]^+$=606.

E. 4-(1,1,4-Trioxo-1,2,5-thiadiazolidin-2-ylmethyl)-benzoic acid 4-methanesulfonyl-benzyl ester 90 mg (150 μmol) of the title D compound, 4-[5-(2,4-dimethoxy-benzyl)-1,1,4-trioxo-1,2,5-thiadiazolidin-2-ylmethyl]-benzoic acid 4-methanesulfonyl-benzyl ester are stirred in 4 mL of 1:1—TFA:$CH_2Cl_2$ for 50 min. The solvent is removed and the residue triturated with 4 mL of 1:1—MeCN:$H_2O$. This mixture is filtered through a 0.2μ disk and the solvent is removed. The resulting material is purified by LC/MS and afforded 4-(1,1,4-trioxo-1,2,5-thiadiazolidin-2-ylmethyl)-benzoic acid 4-methanesulfonyl-benzyl ester: $^1$H-NMR (DMSO-d$_6$) δ 3.22 (3H, s), 3.71 (2H, s), 4.27 (2H, s), 5.48 (2H, s), 7.54 (2H, d, J=8.1), 7.74 (2H, d, J=8.1), 7.96 (2H, d, J=8.5), 8.01 (2H, J=8.5); [M-1]⁻=437.

EXAMPLE 18

The following compounds are prepared analogously to Example 17 by replacing 4-(methylthio)benzyl alcohol with the appropriate alcohol as a starting material.

| Example | Chemical Name | MS [m/z] |
|---|---|---|
| 18-1 | 4-(1,1,4-Trioxo-1,2,5-thiadiazolidin-2-ylmethyl)-benzoic acid 3-chloro-benzyl ester | [M − 1]⁻ = 393 |
| 18-2 | 4-(1,1,4-Trioxo-1,2,5-thiadiazolidin-2-ylmethyl)-benzoic acid 4-butyl-benzyl ester | [M − 1]⁻ = 415 |
| 18-3 | 4-(1,1,4-Trioxo-1,2,5-thiadiazolidin-2-ylmethyl)-benzoic acid 4-hydroxymethyl-benzyl ester | [M − 1]⁻ = 389 |
| 18-4 | 4-(1,1,4-Trioxo-1,2,5-thiadiazolidin-2-ylmethyl)-benzoic acid 2-phenethyl-benzyl ester | [M − 1]⁻ = 463 |
| 18-5 | 4-(1,1,4-Trioxo-1,2,5-thiadiazolidin-2-ylmethyl)-benzoic acid biphenyl-2-ylmethyl ester | [M − 1]⁻ = 435 |
| 18-6 | 4-(1,1,4-Trioxo-1,2,5-thiadiazolidin-2-ylmethyl)-benzoic acid 4-difluoromethoxy-benzyl ester | [M − 1]⁻ = 424 |
| 18-7 | 4-(1,1,4-Trioxo-1,2,5-thiadiazolidin-2-ylmethyl)-benzoic acid 5-(carboxy-difluoro-methyl)-thiophen-2-ylmethyl ester | [M − 1]⁻ = 459 |

EXAMPLE 19

[4-(1,1,4-Trioxo-1,2,5-thiadiazolidin-2-ylmethyl)-phenylmethanesulfonyl]-acetic acid ethyl ester

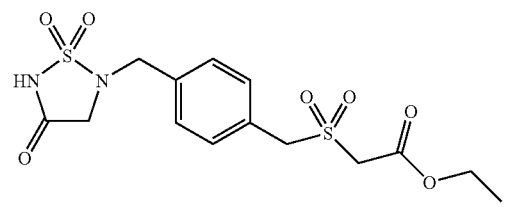

A. 5-(4-Bromomethyl-benzyl)-2-(2,4-dimethoxy-benzyl)-1,1-dioxo-1,2,5-thiadiazolidin-3-one A solution of the title B compound in Example 9, 2,4-dimethoxybenzyl-1,1-dioxo-1,2,5-thiadiazolidin-3-one (2.0 g, 6.98 mmol) in $CH_2Cl_2$ (100 mL) is treated with DBU (1.06 g, 6.98 mmol). α, α'-Dibromo-p-xylene (9.2 g, 34.9 mmol) is added and the mixture is stirred at RT for 16 h. The mixture is filtered and the filtrate is concentrated to 20 mL. The mixture is chromatographed on silica gel using $CH_2Cl_2$ as the eluent. The residual α, α'-dibromo-p-xylene is removed from the product by triturating with $Et_2O$ to afford 5-(4-bromomethyl-benzyl)-2-(2,4-dimethoxy-benzyl)-1,1-dioxo-1,2,5-thiadiazolidin-3-one as a white solid: [M+H]⁺=469.

B. {4-[5-(2,4-Dimethoxybenzyl)-1,1,4-trioxo-1-1,2,5-thiadiazolidin-2-ylmethyl]-benzylsulfanyl}-acetic acid ethyl ester A solution of the title A compound, 5-(4-bromomethyl-benzyl)-2-(2,4-dimethoxy-benzyl)-1,1-dioxo-1,2,5-thiadiazolidin-3-one (200 mg, 0.43 mmol) in DMF (8 mL) is treated with $Cs_2CO_3$ (278 mg, 0.85 mmol) and mercaptoacetic acid ethyl ester (51 mg, 0.43 mmol) at RT. After 16 h, the mixture partitioned between EtOAc and water, and the organic layer is washed with water, dried over anhydrous $MgSO_4$ and concentrated. The residue is chromatographed on silica gel using 10% g→100% EtOAc in hexanes as the eluent to afford {4-[5-(2,4-dimethoxybenzyl)-1,1,4-trioxo-1-1,2,5-thiadiazolidin-2-ylmethyl]-benzylsulfanyl}-acetic acid ethyl ester as a white solid.

C. {4-[5-(2,4-Dimethoxybenzyl)-1,1,4-trioxo-1-1,2,5-thiadiazolidin-2-ylmethyl]-phenylmethanesulfonyl}-acetic acid ethyl ester A solution of the title B compound, {4-[5-(2,4-dimethoxybenzyl)-1,1,4-trioxo-1-1,2,5-thiadiazolidin-2-ylmethyl]-benzylsulfanyl}-acetic acid ethyl ester (55 mg, 0.11 mmol) in $CH_2Cl_2$ (5 mL) is treated with 3-chloroperoxybenzoic acid (47 mg, 0.27 mmol). The mixture is stirred at RT for 4 h and then washed with saturated aqueous $NaHCO_3$ solution. The organic layer is dried over anhydrous $MgSO_4$, and the solvent is evaporated to afford {4-[5-(2,4-dimethoxybenzyl)-1,1,4-trioxo-1-1,2,5-thiadiazolidin-2-ylmethyl]-phenyl-methanesulfonyl}-acetic acid ethyl ester: [M–H]=539.

D. [4-(1,1,4-Trioxo-1,2,5-thiadiazolidin-2-ylmethyl)-phenylmethanesulfonyl]-acetic acid ethyl ester A solution of the title C compound, (4-[5-(2,4-dimethoxy-benzyl)-1,1,4-trioxo-1-1,2,5-thiadiazolidin-2-ylmethyl]-phenylmethanesulfonyl)-acetic acid ethyl ester (60 mg, 0.11 mmol) in $CH_2Cl_2$ (2 mL) is treated with TFA (2 mL). The mixture is stirred at RT for 16 h, and the volatiles are evaporated. The residue is stirred in MeCN/water (1:1, 6 mL) for 30 min. The mixture is passed through a 0.2μ Acrodisc and the solvents are evaporated. The residue is purified via LC/MS to afford [4-(1,1,4-trioxo-1,2,5-thiadiazolidin-2-ylmethyl)-phenylmethane-sulfonyl]-acetic acid ethyl ester as a white solid: [M–H]⁻=389.

EXAMPLE 20

[4-(1,1,4-Trioxo-1,2,5-thiadiazolidin-2-ylmethyl)benzylsulfanyl]-acetic acid ethyl ester

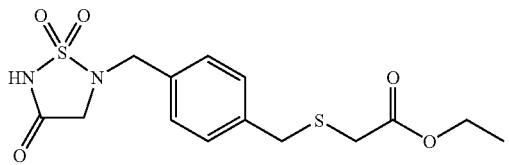

The title compound is prepared by treating the title B compound in Example 19 with TFA using conditions described in Example 19: [M–1]⁻=357.

EXAMPLE 21

5-[4-(3-Methyl-butylsulfanylmethyl)-benzyl]-1,1-dioxo-1,2,5-thiadiazolidin-3-one

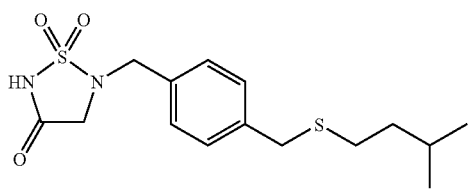

The title compound is prepared analogously to Example 19: [M–1]⁻=341.

EXAMPLE 22

4-(1,1,4-Trioxo-1,2,5-thiadiazolidin-2-ylmethyl)benzoic acid 2-ethyl-butyl ester

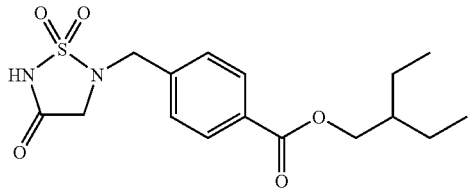

A. 4-Bromomethyl-benzoyl chloride

A solution of 4-bromomethyl-benzoic acid (8.6 g, 0.04 mol) in 7.23 mL $SOCl_2$ (0.1 mol) is heated to reflux for 5 h. $SOCl_2$ is removed, and the residue is recrystalized from hexane to afford 4-bromomethyl-benzoyl chloride as a white crystalline solid.

B. 4-Bromomethyl-benzoic Acid 2-ethyl-butyl ester

A solution of the title A compound, 4-bromomethyl-benzoyl chloride (466 mg, 2 mmol) in 3 mL of $CH_2Cl_2$ is added dropwise to a solution of 2-ethyl-1-butanol (204 mg, 2 mmol) and TEA (202 mg, 2 mmol) in 10 mL of $CH_2Cl_2$ at 0~5° C. over 30 min. The reaction is allowed to warm to RT and stirred overnight. The solvent is evaporated and the residue is partitioned between hexane and water. The organic phase is dried over anhydrous $MgSO_4$ and concentrated. The residue is chromatographic on silica gel using EtOAc/hexane (gradient 90-70) to give 4-bromomethyl-benzoic acid 2-ethyl-butyl ester as a colorless oil.

C. 4-[5-(2,4-Dimethoxy-benzyl)-1,1,4-trioxo1,2,5-thiadiazolidin-2-ylmethyl]-benzoic acid 2-ethyl-butyl ester DBU (127 mg, 0.836 mmol) is added slowly to a suspension of the title B compound, 4-bromomethyl-benzoic acid 2-ethyl-butyl ester (250 mg, 0.836 mmol) and the title B compound in Example 9, 2-(2,4-dimethoxybenzyl)-1,1-dioxo-1,2,5-thiadiazolidin-3-one (240 mg, 0.836 mmol) in 10 mL of $CH_2Cl_2$ at RT. The resulting solution is stirred at RT overnight. The solvent is evaporated under reduced pressure and the residue is chromatographed on silica gel with EtOAc/hexane (gradient 60-40) to afford 4-[5-(2,4-dimethoxy-benzyl)-1,1,4-trioxo1,2,5-thiadiazolidin-2-ylmethyl]-benzoic acid 2-ethyl-butyl ester as a white solid.

D. 4-(1,1,4-Trioxo-1,2,5-thiadiazolidin-2-ylmethyl)-benzoic acid 2-ethyl-butyl ester A solution of the title C compound, 4-[5-(2,4-dimethoxy-benzyl)-1,1,4-trioxo-1,2,5-thiadiazolidin-2-ylmethyl]-benzoic acid 2-ethyl-butyl ester (230 mg, 0.456 mmol) and 2 mL of TFA in 6 mL of $CH_2Cl_2$ is stirred at RT overnight. The solvent is evaporated and the residue is treated with MeCN and filtered. The filtrate is concentrated and the residue is treated with $Et_2O$, filtered and the $Et_2O$ is evaporated to give 4-(1,1,4-trioxo-1,2,5-thiadiazolidin-2-ylmethyl)-benzoic acid 2-ethyl-butyl ester as a light pink colored solid: $[M-H]^- = 353$.

EXAMPLE 23

The following compounds are prepared analogously to Example 22 by replacing 2-ethyl-1-butanol with the appropriate alcohol as a starting material.

| Example | Chemical Name | MS [m/z] |
| --- | --- | --- |
| 23-1 | 4-(1,1,4-Trioxo-1,2,5-thiadiazolidin-2-ylmethyl)-benzoic acid cyclobutylmethyl ester | $[M - 1]^- = 339$ |
| 23-2 | 4-(1,1,4-Trioxo-1,2,5-thiadiazolidin-2-ylmethyl)-benzoic acid cyclopentylmethyl ester | $[M - 1]^- = 352$ |
| 23-3 | 4-(1,1,4-Trioxo-1,2,5-thiadiazolidin-2-ylmethyl)-benzoic acid 2-methyl-pentyl ester | $[M - 1]^- = 353$ |
| 23-4 | 4-(1,1,4-Trioxo-1,2,5-thiadiazolidin-2-ylmethyl)-benzoic acid 2,4,4-trimethyl-pentyl ester | $[M - 1]^- = 381$ |
| 23-5 | 4-(1,1,4-Trioxo-1,2,5-thiadiazolidin-2-ylmethyl)-benzoic acid cyclohexylmethyl ester | $[M - 1]^- = 365$ |
| 23-6 | 4-(1,1,4-Trioxo-1,2,5-thiadiazolidin-2-ylmethyl)-benzoic acid 1,2-dimethyl-propyl ester | $[M - 1]^- = 339$ |
| 23-7 | 4-(1,1,4-Trioxo-1,2,5-thiadiazolidin-2-ylmethyl)-benzoic acid cyclopentyl ester | $[M - 1]^- = 337$ |
| 23-8 | 4-(1,1,4-Trioxo-1,2,5-thiadiazolidin-2-ylmethyl)-benzoic acid 2-methyl-butyl ester | $[M - 1]^- = 339$ |
| 23-9 | 4-(1,1,4-Trioxo-1,2,5-thiadiazolidin-2-ylmethyl)-benzoic acid 2-methylsulfanyl-ethyl ester | $[M - 1]^- = 343$ |
| 23-10 | 4-(1,1,4-Trioxo-1,2,5-thiadiazolidin-2-ylmethyl)-benzoic acid 2-carboxymethylsulfanyl-ethyl ester | $[M - 1]^- = 387$ |
| 23-11 | 4-(1,1,4-Trioxo-1,2,5-thiadiazolidin-2-ylmethyl)-benzoic acid 5-nitro-furan-2-ylmethyl ester | $[M - 1]^- = 394$ |
| 23-12 | 4-(1,1,4-Trioxo-1,2,5-thiadiazolidin-2-ylmethyl)-benzoic acid pyridin-2-ylmethyl ester | $[M - 1]^- = 360$ |
| 23-13 | 4-(1,1,4-Trioxo-1,2,5-thiadiazolidin-2-ylmethyl)-benzoic acid 3-hydroxymethyl-benzyl ester | $[M - 1]^- = 389$ |
| 23-14 | 4-(1,1,4-Trioxo-1,2,5-thiadiazolidin-2-ylmethyl)-benzoic acid 3-methanesulfonyl-benzyl ester | $[M - 1]^- = 437$ |
| 23-15 | (4-{4-[4-(1,1,4-Trioxo-1,2,5-thiadiazolidin-2-ylmethyl)-benzoylamino]-butyl}-phenyl)-acetic acid | $[M + 1]^+ = 460$ |
| 23-16 | (4-{3-[4-(1,1,4-Trioxo-1,2,5-thiadiazolidin-2-ylmethyl)-benzoylamino]-propyl}-phenyl)-acetic acid | $[M + 1]^+ = 446$ |
| 23-17 | 4-(1,1,4-Trioxo-1,2,5-thiadiazolidin-2-ylmethyl)-benzoic acid 5-dimethylaminomethyl-furan-2-ylmethyl ester | $[M - 1]^- = 406$ |

(i)

(ii) EXAMPLE 24

(S)-2-Acetylamino-N-{(S)-1-pentylcarbamoyl-2-[3-(1,1,4-trioxo-1,2,5-thiadiazolidin-2-ylmethyl)phenyl]-ethyl}-3-phenyl-propionamide

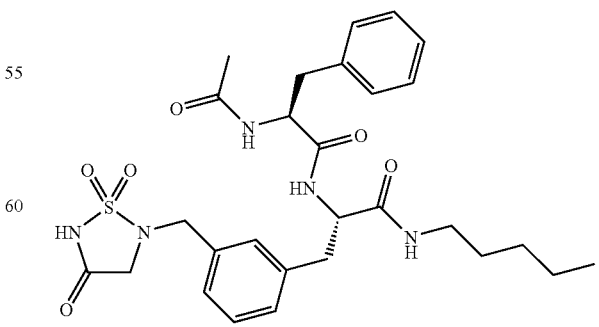

A Glycine-N-sulfonic acid 4-methoxybenzylamide

To a solution of glycine methyl ester-N-sulfonic acid 4-methoxybenzylamide (3.03 g, 10.5 mmol, prepared analogously to literature procedure as described by Ducry, L.; Reinelt, S.; Seiler, P.; Diederich, F. *Helvetica Chimica. Acta.* 1999, 82, 2432-47) in 80 mL of 1,4-dioxane are added 20 mL of water and 21 mL of 1N aqueous NaOH. After 40 min, the solvent is evaporated and the aqueous residue is extracted with $Et_2O$. The aqueous solution is acidified with 1N aqueous HCl and the product is taken up in EtOAc, dried over anhydrous $Na_2SO_4$ and concentrated to give glycine-N-sulfonic acid 4-methoxybenzyl-amide: $[M-1]^-=273$.

(ii) B. 2-(4-Methoxybenzyl)-1,1-dioxo-1,2,5-thiadiazolidin-3-one

To a solution of the title A compound, glycine-N-sulfonic acid 4-methoxybenzyl-amide (2.51 g, 9.2 mmol) in 160 mL of THF is added HOBt (1.41 g, 9.2 mmol). After HOBt is dissolved, EDCl (1.76 g, 9.2 mmol) is added and after 10 min, followed by TEA (1.42 mL, 10.2 mmol). The reaction is stirred for 16 h, then concentrated and the residue is partitioned between 1N aqueous HCl and EtOAc. The organic solution is washed with brine, dried over anhydrous $Na_2SO_4$ and concentrated to give an oil which solidifies on standing. This is dissolved in hot EtOAc, concentrated down to 20 mL, filtered to remove solids and chromatographed on silica gel using 40% EtOAc in hexanes as the eluent to afford 2-(4-methoxy-benzyl)-1,1-dioxo-1,2,5-thiadiazolidin-3-one as a white solid: mp=111-113° C.; $[M-1]^-=255$.

C. 5-(3-Iodo-benzyl)-2-(4-methoxy-benzyl)-1,1-dioxo-1,2,5-thiadiazolidin-3-one

A solution of the title B compound, 2-(4-methoxybenzyl)-1,1-dioxo-1,2,5-thiadiazolidin-3-one (1.02 g, 3.98 mmol), 3-iodo-benzyl alcohol (1.01 mL, 7.95 mmol) and triphenylphosphine (2.10 g, 8.0 mmol) in THF (50 mL) is cooled to 5° C. and treated with a solution of diethyl azodicarboxylate (1.26 mL, 8.0 mmol) in THF (10 mL). The reaction is allowed to warm to RT over 16 h. The reaction mixture is concentrated to yield a yellow oil. This is chromatographed on a 110 g silica gel RediSep column (Isco, Inc.) with a 30 mL/min gradient elution of 0:100 (EtOAc:$CH_2Cl_2$) to 5:95 over 25 min. Fractions containing product are combined and concentrated to yield an oil, which spontaneously crystallizes. Trituration with $Et_2O$ yields 5-(3-iodo-benzyl)-2-(4-methoxy-benzyl)-1,1-dioxo-1,2,5-thiadiazolidin-3-one as a white solid: mp=98-100° C.

D. (S)-2-t-Butoxycarbonylamino-3-{3-[5-(4-methoxy-benzyl)-1,1,4-trioxo-1,2,5-thiadiazolidin-2-ylmethyl]-phenyl}-propionic acid benzyl ester Onto zinc foil (99.9% Aldrich 35,602-6, 145 mg, 2.22 mmol) cut in small pieces is added DMF (freshly distilled from $CaH_2$ under argon, 0.4 mL) and 1,2-dibromoethane (0.007 mL, 0.08 mmol) under argon. The mixture is heated at 50° C. for 10 min, then allowed to cool and trimethylsilyl chloride (0.004 mL, 0.032 mmol) is added. The reaction is stirred for 25 min and a solution of (R)-2-t-butoxycarbonyl-amino-3-iodo-propionic acid benzyl ester (Fluka, 417 mg, 1.03 mmol) in DMF (1 mL) is added. After 1 h, the mixture is decanted into a solution of the title C compound, 5-(3-iodo-benzyl)-2-(4-methoxy-benzyl)-1,1-dioxo-1,2,5-thiadiazolidin-3-one (378 mg, 0.80 mmol), tri-o-tolylphosphine (49 mg, 0.16 mmol) and tris(dibenzylideneacetone)-dipalladium(0) (37 mg, 0.04 mmol) in DMF (2 mL). After stirring for 1.5 h, the resulting reaction mixture is poured onto water (100 mL) and extracted with EtOAc (2×100 mL). The combined EtOAc layers are washed with water (1×200 mL) and brine (1×200 mL), dried over anhydrous $MgSO_4$, filtered and concentrated to give a yellow oil. This is chromatographed on a 35 g silica gel RediSep column (Isco, Inc.) with a 30 mL/min gradient elution of 15:85 (EtOAc:hexane) to 60:40 over 20 min. Fractions containing product are combined and concentrated to yield (S)-2-t-butoxycarbonylamino-3-(3-[5-(4-methoxy-benzyl)-1,1,4-trioxo-1,2,5-thiadiazolidin-2-ylmethyl]-phenyl}-propionic acid benzyl ester as a light brown foam: $[M+1]^+=624$.

E. (S)-2-t-Butoxycarbonylamino-3-{3-[5-(4-methoxy-benzyl)-1,1,4-trioxo-1,2,5-thiadiazolidin-2-ylmethyl]-phenyl}-propionic acid The title D compound, (S)-2-t-butoxycarbonylamino-3-{3-[5-(4-methoxy-benzyl)-1,1,4-trioxo-1,2,5-thiadiazolidin-2-ylmethyl]-phenyl}-propionic acid benzyl ester (127 mg, 0.20 mmol) is dissolved in EtOAc/EtOH (50:50) (56 mL) and 10% palladium on carbon (35 mg) is added and the mixture is treated with 45 psi of hydrogen on a Parr shaker apparatus. After two 90 min runs, starting material is not completely consumed, so another aliquot of 10% palladium on carbon (35 mg) is added and after shaking at 45 psi hydrogen for 30 min, the reaction is complete. The mixture is filtered through celite, the filtrate is concentrated and dried to give (S)-2-t-butoxycarbonylamino-3-{3-[5-(4-methoxy-benzyl)-1,1,4-trioxo-1,2,5-thiadiazolidin-2-ylmethyl]-phenyl}-propionic acid as a white foam: $[M+1]^+=534$.

F. ((S)-2-{3-[5-(4-Methoxy-benzyl)-1,1,4-trioxo-1,2,5-thiadiazolidin-2-ylmethyl]-phenyl}-1-pentylcarbamoyl-ethyl)-carbamic acid t-butyl ester HOBt (28 mg, 0.179 mmol), pentyl amine (0.021 mL, 0.179 mmol) and EDCl (38 mg, 0.198 mmol) are added to a solution of the title E compound, (S)-2-t-butoxycarbonyl-amino-3-{3-[5-(4-methoxy-benzyl)-1,1,4-trioxo-1,2,5-thiadiazolidin-2-ylmethyl]-phenyl}-propionic acid (96 mg, 0.179 mmol) in $CH_2Cl_2$ (4 mL) at RT. After 2H, the reaction is concentrated and the residue is taken up in EtOAc. The organic solution is washed with 1N aqueous HCl, saturated aqueous $NaHCO_3$ and brine, dried over anhydrous $MgSO_4$, filtered and concentrated to yield the product as an oil. This is chromatographed on a 10 g silica gel RediSep column (Isco, Inc.) with a 30 mL/min gradient elution of 30:70 (EtOAc:hexane) to 60:40 over 10 min. Fractions containing product are combined and concentrated to yield ((S)-2-{3-[5-(4-methoxy-benzyl)-1,1,4-trioxo-1,2,5-thiadiazolidin-2-ylmethyl]-phenyl}-1-pentylcarbamoyl-ethyl)-carbamic acid t-butyl ester as a white foam: $[M+1]^+=603$.

G. (S)-2-Amino-3-{3-[5-(4-methoxy-benzyl)-1,1,4-trioxo-1,2,5-thiadiazolidin-2-ylmethyl]-phenyl}-N-pentyl-propionamide To a solution of the title F compound, ((S)-2-{3-[5-(4-methoxy-benzyl)-1,1,4-trioxo-1,2,5-thiadiazolidin-2-ylmethyl]-phenyl}-1-pentylcarbamoyl-ethyl)-carbamic acid t-butyl ester (77 mg, 0.127 mmol) in $CH_2Cl_2$ (1 mL) is added TFA (1 mL). After 30 min, the solvent is removed under stream of nitrogen. The residue is partitioned between EtOAc and saturated aqueous NaHCO$_3$. The organic solution is washed with brine, dried over anhydrous MgSO$_4$ and concentrated to yield (S)-2-amino-3-{3-[5-(4-methoxy-benzyl)-1,1,4-trioxo-1,2,5-thiadiazolidin-2-ylmethyl]-phenyl}-N-pentyl-propionamide as a clear oil: [M+1]$^+$=503.

H. (S)-2-((S)-2-Acetylamino-3-phenyl-propionylamino)-3-{3-[5-(4-methoxy-benzyl)-1,1,4-trioxo-1,2,5-thiadiazolidin-2-ylmethyl]-phenyl}-N-pentyl-propionamide HOBt (19 mg, 0.125 mmol), (S)-2-acetylamino-3-phenyl-propionic acid (26 mg, 0.125 mmol) and EDCl (26 mg, 0.138 mmol) are added to a solution of the title G compound, (S)-2-amino-3-{3-[5-(4-methoxy-benzyl)-1,1,4-trioxo-1,2,5-thiadiazolidin-2-ylmethyl]-phenyl}-N-pentylpropionamide (63 mg, 0.125 mmol) in CH$_2$Cl$_2$ (4 mL) at RT. After 30 min, the reaction is concentrated. The product is taken up in EtOAc, washed with 1N aqueous HCl, saturated aqueous NaHCO$_3$ and brine. The organic solution is dried over anhydrous MgSO$_4$ and concentrated to yield (S)-2-((S)-2-acetylamino-3-phenyl-propionylamino)-3-{3-[5-(4-methoxy-benzyl)-1,1,4-trioxo-1,2,5-thiadiazolidin-2-ylmethyl]-phenyl}-N-pentyl-propionamide as a white foam: [M+1]$^+$=692.

I. (S2-Acetylamino-N-{(S)-1-pentylcarbamoyl-2-[3-(1,1,4-trioxo-1,2,5-thiadlazolidin-2-ylmethyl)-phenyl]-ethyl}-3-phenyl-propionamide The title H compound, (S)-2-((S)-2-acetylamino-3-phenyl-propionylamino)-3-{3-[5-(4-methoxy-benzyl)-1,1,4-trioxo-1,2,5-thiadiazolidin-2-ylmethyl]-phenyl}-N-pentyl-propionamide (77 mg, 0.111 mmol) is dissolved in TFA (2.2 mL) containing t-butyl-dimethylsilane (0.055 mL, 0.33 mmol) and heated at 80° C. for 3.75 h. The reaction is concentrated under nitrogen stream and the resulting tan solid is taken up in 60% MeCN in water. Water (1 mL) is added, and the mixture is filtered through a 0.1 micron Acrodisc filter. The filtrate is loaded onto a preparative reverse phase HPLC column (YMC CombiPrep Pro C18, 50×20 mm I.D., particle size S-5 micron, 12 nM) in 7 aliquots and eluted at 30 mL/min with a gradient of 90:10 (water containing 0.1% TFA: MeCN) to 10:90 over 5 min. Then held at 10:90 until 7 min. Fractions containing product are combined and concentrated on a Savant Speedvac to yield the product still containing an unknown impurity by HPLC. This is chromatographed again, using the same column, but a different elution gradient, 90:10 (0.1% TFA in water: MeCN) to 40:60 over 14 min. Fractions containing product are combined and concentrated to yield (S)-2-acetylamino-N-{(S)-1-pentylcarbamoyl-2-[3-(1,1,4-trioxo-1,2,5-thiadiazolidin-2-ylmethyl)-phenyl]-ethyl}-3-phenyl-propionamide as a white film: [M+1]$^+$=572.

EXAMPLE 25

5-(1H-Indol-5-ylmethyl)-1,1-dioxo-1,2,5-thiadiazolidin-3-one

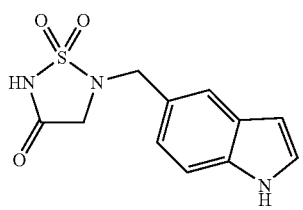

A. N-(2-Trimethylsilanyl-ethoxycarbonyl-aminosulfonyl)-N-(1H-indol-5ylmethyl)-glycine methyl ester Chlorosulfonylisocyanate (0.082 mL, 0.95 mmol) is added to CH$_2$Cl$_2$ (6 mL) in a dry round bottomed flask under argon balloon, and cooled with stirring in an ice/salt/water bath. Trimethylsilylethanol (0.137 mL, 0.96 mmol) in CH$_2$Cl$_2$ (1 mL) is added to this solution and stirred while maintaining the cooling for 1 h. Then a solution [(1H-Indol-5-ylmethyl)-amino]-acetic acid methyl ester (167 mg, 0.77 mmol, obtained by alkylation of C-(1H-Indol-5-yl)-methylamine using the method of Tohru Fukuyama et. al., Tett. Lett. 38 (33) pp. 5831-34, 1997) and TEA (0.41 mL, 2.9 mmol) in CH$_2$Cl$_2$ (6 mL) is added into this above mentioned stirred, cooled solution. After 1 h, the reaction is poured into 40 mL of 1N aqueous HCl and extracted with Et$_2$O. The ether layer is washed with 1N aqueous HCl, separated, dried over anhydrous Na$_2$SO$_4$, filtered and concentrated. The resulting residue is chromatographed on a 10 g silica gel RediSep (Isco Inc.) column with a 30 mL/min gradient elution of 15:85 (EtOAc:hexane) to 40:60 over 15 min. Fractions containing product are combined and evaporated yield N-(2-trimethylsilanyl-ethoxycarbonyl-aminosulfonyl)-N-(1H-indol-5ylmethyl)-glycine methyl ester as a yellow oil: $^1$H-NMR (300 MHz, DMSO-d$_6$) δ 0.0 (s, 9H), 0.9 (t, 2H), 3.55 (s, 3H), 3.9 (s, 2H), 4.05 (t, 2H), 4.5 (s, 2H), 6.4 (s, 1H), 6.95 (d, 1H), 7.3 (m, 2H), 7.4 (s, 1H), 12.0 (s, 1H), 12.4 (s, 1H).

B. 5-(1H-Indol-5-ylmethyl)-1,1-dioxo-1,2,5-thiadiazolidin-3-one

Tetrabutylammonium fluoride trihydrate (252 mg, 0.80 mmol) and AcOH (0.057 mL, 1.0 mmol) are dissolved in tetrahydrofuran (4 mL) and this is used to dissolve the title A compound, N-(2-trimethylsilanyl-ethoxycarbonyl-aminosulfonyl)-N-(1H-indol-5ylmethyl)-glycine methyl ester (90 mg, 0.20 mmol) in a thick-walled round bottomed flask. This is sealed and stirred in an oil bath at 80° C. for 16 h. The reaction is allowed to cool, then diluted with 1N aqueous HCl (5 mL) and Et$_2$O (25 mL). The organic layer is separated and washed with water (2×5 mL) and saturated aqueous NaCl (5 mL), then separated, dried over anhydrous MgSO$_4$, filtered and evaporated, to yield the crude product as a brown oil. This is taken up in water (4.5 mL), MeCN (0.7 mL) and DMSO (1 mL). The resulting mixture is loaded onto a preparative reverse phase HPLC column (YMC CombiPrep Pro Cl 8, 50×20 mm I.D., particle size S-5 micron, 12 nM) in 3 aliquots and eluted at 30 mL/min with a gradient of 90:10 (water containing 0.1% TFA: MeCN) at 0 min to 10:90 at 5 min. Then held at 10:90 until 7 minutes. Fractions containing product are combined and concentrated on a Savant Speedvac to yield 5-(1H-indol-5-ylmethyl)-1,1-dioxo-1,2,5-thiadiazolidin-3-one as a light tan foam: [M−1]$^−$=264.

EXAMPLE 26

1,1-Dioxo-5-(3,4,5-trimethoxy-benzyl)-1,2,5-thiadiazolidin-3-one

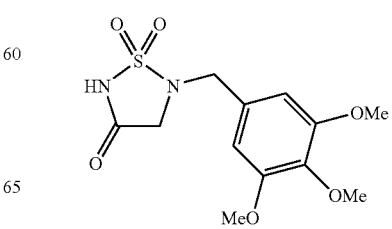

The title compound is prepared analogously to Example 25 using 3,4,5-trimethoxybenzylamine as the starting material: [M−1]⁻=315.

EXAMPLE 27

5-[4-(4-Benzyl-piperazin-1-ylmethyl)-benzyl]-1,1-dioxo-1,2,5-thiadiazolidin-3-one

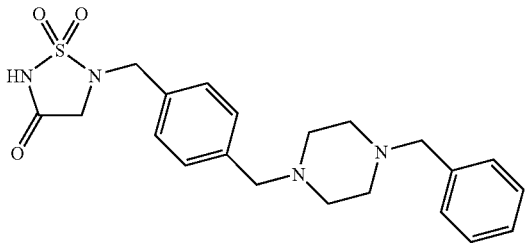

A. 4-[5-(2,4-Dimethoxy-benzyl)-1,1,4-trioxo-1-1,2,5thiadiazolidin-2-ylmethyl]-benzaldehyde DBU (4.36 g, 0.0286 mol) is added to a suspension of 4-bromomethyl-benzaldehyde (5.70 g, 0.0286 mol) and the title B compound in Example 9, 2-(2,4-dimethoxybenzyl)-1,1-dioxo-1,2,5-thiadiazolidin-3-one (8.2 g, 0.0286 mol) in CH₂Cl₂ (100 mL) slowly at RT. After the addition is completed, the resulting solution is stirred overnight. The solvent is evaporated and the residue is chromatographed on silica gel with CH₂Cl₂/EtOAc (gradient 5~25%) to afford 4-[5-(2,4-dimethoxy-benzyl)-1,1,4-trioxo-1-1,2,5-thiadiazolidin-2-ylmethyl]-benzaldehyde as a white solid.

B. 5-[4-(4-Benzyl-piperazin-1-ylmethyl)-benzyl]-2-(2,4-dimethoxy-benzyl)-1,1-dioxo-1,2,5-thiadiazolidin-3-one A mixture of the title A compound, 4-[5-(2,4-dimethoxy-benzyl)-1,1,4-trioxo-1-1,2,5-thiadiazolidin-2-ylmethyl]-benzaldehyde (202 mg, 0.5 mmol), 1-benzylpiperazine (88 mg, 0.5 mmol) and sodium triacetoxyborohydride (672 mg, 1.56 mmol) in 10 mL CH₂Cl₂ is stirred at RT for 24 h. The mixture is washed with water and dried over anhydrous MgSO₄, filtered and the solvent is evaporated to dryness to give 5-[4-(4-benzyl-piperazin-1-ylmethyl)-benzyl]-2-(2,4-dimethoxy-benzyl)-1,1-dioxo-1,2,5-thiadiazolidin-3-one which is used as such in the next step: [M+1]⁺=565.

C. 5-[4-(4-Benzyl-piperazin-1-ylmethyl)-benzyl]-1,1-dioxo-1,2,5-thiadiazolidin-3-one The title B compound, 5-[4-(4-benzyl-piperazin-1-ylmethyl)-benzyl]-2-(2,4-dimethoxy-benzyl)-1,1-dioxo-1,2,5]thiadiazolidin-3-one (250 mg, 0.44 mmol) dissolved in a mixture of TFA (3 mL) and CH₂Cl₂ (3 mL) is stirred at RT overnight. The solvent is evaporated and the residue is treated with a mixture of MeCN/water (50/50). The solid is filtered off and the solvent is evaporated to dryness. The residue is treated with cold MeOH (2 mL) to afford a white solid which is collected by filtration and washed with Et₂O to afford 5-[4-(4-benzyl-piperazin-1-ylmethyl)-benzyl]-1,1-dioxo-1,2,5-thiadiazolidin-3-one as a white solid: [M+1]⁺= 415, [M−1]⁻=413.

EXAMPLE 28

The following compounds are prepared by analogously to Example 27.

| Example | Chemical Name | MS [m/z] |
| --- | --- | --- |
| 28-1 | 1,1-Dioxo-5-{4-[3-oxo-3H-benzofuran-(2Z)-ylidenemethyl]-benzyl}-1,2,5-thiadiazolidin-3-one | [M − 1]⁻ = 369 |
| 28-2 | [4-(1,1,4-Trioxo-1,2,5-thiadiazolidin-2-ylmethyl)-phenyl]-acetic acid | [M − 1]⁻ = 283 |
| 28-3 | 5-(4-Benzoyl-benzyl)-1,1-dioxo-1,2,5-thiadiazolidin-3-one | [M − 1]⁻ = 329 |
| 28-4 | 1-Phenyl-2-[4-(1,1,4-trioxo-1,2,5-thiadiazolidin-2-ylmethyl)-phenyl]-ethane-1,2-dione | [M − 1]⁻ = 357 |
| 28-5 | 5-Naphthalen-2-ylmethyl-1,1-dioxo-1,2,5-thiadiazolidin-3-one | [M − 1]⁻ = 275 |
| 28-6 | 5-[4-(4-Methyl-pentanoyl)-benzyl]-1,1-dioxo-1,2,5-thiadiazolidin-3-one | [M − 1]⁻ = 323 |
| 28-7 | 2-(1,1,4-Trioxo-1,2,5-thiadiazolidin-2-ylmethyl)-anthraquinone | [M − 1]⁻ = 355 |
| 28-8 | 5-[3-(2-Fluoro-phenoxy)-benzyl]-1,1-dioxo-1,2,5-thiadiazolidin-3-one | [M − 1]⁻ = 335 |
| 28-9 | 3-{2-[4-(1,1,4-Trioxo-1,2,5-thiadiazolidin-2-ylmethyl)-phenyl]-ethoxy}-benzoic acid | [M − 1]⁻ = 389 |
| 28-10 | 1-(3-Methyl-butyl)-6-(1,1,4-trioxo-1,2,5-thiadiazolidin-2-ylmethyl)-1H-quinolin-2-one | [M − 1]⁻ = 362 |

EXAMPLE 29

5-(1,1,4-Trioxo-1,2,5-thiadiazolidin-2-ylmethyl)-thiophene-2-carboxylic acid methyl-phenethyl-amide

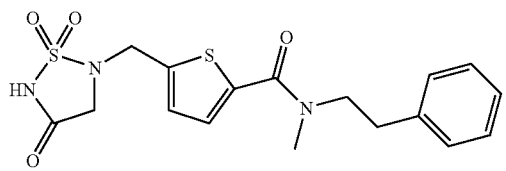

A. 5-Methyl-thiophene-2-carboxylic acid 2-trimethylsilanyl-ethyl ester

A solution of 5-Methyl-thiophene-2-carboxylic acid (23.58 g, 166 mmol) in MeCN (300 mL) is treated with EDCl (33.41 g, 174 mmol) and DMAP (2.03 g, 16 mmol). The mixture is stirred for 5 min and 2-(trimethylsilyl)ethanol (19.61 g, 166 mmol) is added. The mixture is stirred at RT for 16 h and the solvent is evaporated. The residue is partitioned between EtOAc and water. The organic layer is diluted with an equal portion of hexane and dried over anhydrous MgSO$_4$. The solution is passed through a plug of silica gel and the solvents are evaporated to dryness to give 5-methyl-thiophene-2-carboxylic acid 2-trimethylsilanyl-ethyl ester as a clear oil.

B. 5-Bromomethyl-thiophene-2-carboxylic acid 2-trimethylsilanyl-ethyl ester

A solution of the title A compound, 5-methyl-thiophene-2-carboxylic acid 2-trimethylsilanyl-ethyl ester (34.15 g, 141 mmol) in CCl$_4$ (200 mL) is treated with N-bromosuccinimide (NBS, 25.08 g, 141 mmol) and 2,2'-azobisisobutyronitrile (1.0 g, 6 mmol). The mixture is irradiated with a 450 W mercury lamp for 3 h. An additional 2.5 g of NBS is added and the mixture is further irradiated for 2 h. The mixture is filtered through Celite and a plug of silica gel. The solvent is evaporated to give 5-bromomethyl-thiophene-2-carboxylic acid 2-trimethylsilanyl-ethyl ester as a yellow liquid.

C. 5-[5-(2,4-Dimethoxy-benzyl)-1,1,4-trioxo-1,2,5]thiadiazolidin-2-ylmethyl]-thiophene-2-carboxylic Acid 2-trimethylsilanyl-ethyl ester A solution of the title B compound in Example 9, 2-(2,4-dimethoxybenzyl)-1,1-dioxo-1,2,5-thiadiazolidin-3-one (7.00 g, 24.4 mmol) and DBU (3.71 g, 24.4 mmol) in CH$_2$Cl$_2$ (200 mL) is treated with the title B compound, 5-bromomethyl-thiophene-2-carboxylic acid 2-trimethylsilanyl-ethyl ester (8.25 g, 25.7 mmol). The mixture is stirred at RT for 3 h and the solvent is evaporated. The residue is chromatographed over silica gel using 20%-50% EtOAc in hexane as the eluent to afford 5-[5-(2,4-dimethoxy-benzyl)-1,1,4-trioxo-1,2,5]thiadiazolidin-2-ylmethyl]-thiophene-2-carboxylic acid 2-trimethylsilanyl-ethyl ester as a yellow oil.

D. 5-[5-(2,4-Dimethoxy-benzyl)-1,1,4-trioxo-1,2,5-thiadiazolidin-2-ylmethyl)-thiophene-2-carboxylic acid A solution of the title C compound, 5-[5-(2,4-dimethoxy-benzyl)-1,1,4-trioxo-1,2,5]thiadiazolidin-2-ylmethyl]-thiophene-2-carboxylic acid 2-trimethylsilanyl-ethyl ester (1.07 g, 2.03 mmol) in anhydrous THF (20 mL) is treated with a 1 M solution of tetrabutylammonium fluoride (4.4 mL, 4.46 mmol) in THF at RT for 3 h. The solvent is evaporated and the residue is partitioned between EtOAc and water. The organic layer is washed with 1N aqueous HCl and dried over anhydrous MgSO$_4$. The solvent is evaporated to afford 5-[5-(2,4-dimethoxy-benzyl)-1,1,4-trioxo-1,2,5-thiadiazolidin-2-ylmethyl]-thiophene-2-carboxylic acid as a yellow solid: $[M-1]^- = 425$.

E. 5-[5-(2,4-Dimethoxy-benzyl)-1,1,4-trioxo-1,2,5-thiadiazolidin-2-ylmethyl]-thiophene-2-carboxylic acid methyl-phenethyl-amide A solution of the title D compound, 5-[5-(2,4-dimethoxy-benzyl)-1,1,4-trioxo-1,2,5-thiadiazolidin-2-ylmethyl]-thiophene-2-carboxylic acid (220 mg, 0.52 mmol) in toluene (10 mL) is treated with SOCl$_2$ (3 mL) and the mixture is heated at 80° C. for 1 h. The volatiles are evaporated and the residue is dissolved in toluene. The solvent is evaporated again and the residue is dissolved in CH$_2$Cl$_2$ (10 mL). A mixture of N-methylphenethylamine (35 mg, 0.25 mmol) and triethylamine (39 mg, 38.7 mmol) in CH$_2$Cl$_2$ (1 mL) is added and the mixture is stirred for 16 h. The solvent is evaporated and the residue is chromatographed over silica gel using 0-100% EtOAc in hexane as the eluent to afford 5-[5-(2,4-dimethoxy-benzyl)-1,1,4-trioxo-1,2,5-thiadiazolidin-2-ylmethyl]-thiophene-2-carboxylic acid methyl-phenethyl-amide as a clear oil: $[M+1]^+ = 544$.

F. 5-(1,1,4-Trioxo-1,2,5-thiadiazolidin-2-ylmethyl)thiophene-2-carboxylic acid methyl-phenethylamide A solution of the title E compound, 5-[5-(2,4-dimethoxy-benzyl)-1,1,4-trioxo-1,2,5-thiadiazolidin-2-ylmethyl]-thiophene-2-carboxylic acid methyl-phenethyl-amide (70 mg, 0.13 mmol) in CH$_2$Cl$_2$ (2 mL) is stirred with TFA (2 mL) at RT for 4 h. The volatiles are evaporated and the residue is stirred in equal volumes of MeCN/water (4 mL). The mixture is filtered through a 0.2µ Acrodisc and the solvents are evaporated to dryness. The residue is triturated from Et$_2$O to afford 5-(1,1,4-trioxo-1,2,5-thiadiazolidin-2-ylmethyl)-thiophene-2-carboxylic acid methyl-phenethylamide as an off white solid: $[M-1]^- = 392$.

EXAMPLE 30

The following compounds are prepared analogously to Example 29.

| Example | Chemical Name | MS [m/z] |
| --- | --- | --- |
| 30-1 | 5-(1,1,4-Trioxo-1,2,5-thiadiazolidin-2-ylmethyl)-thiophene-2-carboxylic acid (2-thiophen-2-yl-ethyl)-amide | $[M - 1]^- = 384$ |
| 30-2 | 5-(1,1,4-Trioxo-1,2,5-thiadiazolidin-2-ylmethyl)-thiophene-2-carboxylic acid phenethyl-amide | $[M - 1]^- = 378$ |
| 30-3 | [4-(2-{[5-(1,1,4-Trioxo-1,2,5-thiadiazolidin-2-ylmethyl)-thiophene-2-carbonyl]-amino}-ethyl)-phenyl]-acetic acid | $[M - 1]^- = 436$ |
| 30-4 | 5-(1,1,4-Trioxo-1,2,5-thiadiazolidin-2-ylmethyl)-thiophene-2-carboxylic acid 4-carboxy-benzyl ester | $[M - 1]^- = 409$ |
| 30-5 | 5-(1,1,4-Trioxo-1,2,5-thiadiazolidin-2-ylmethyl)-thiophene-2-carboxylic acid isobutyl ester | $[M - 1]^- = 331$ |
| 30-6 | 5-(1,1,4-Trioxo-1,2,5-thiadiazolidin-2-ylmethyl)-thiophene-2-carboxylic acid isobutyl-amide | $[M - 1]^- = 330$ |

EXAMPLE 31

2-Amino-N-[4-(1,1,4-trioxo-1,2,5-thiadiazolidin-2-ylmethyl)-benzyl]-acetamide

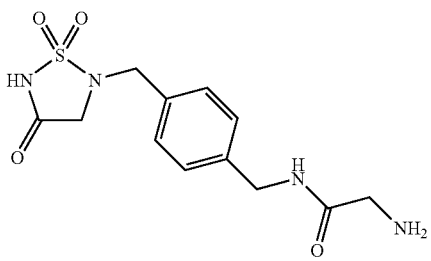

A. {4-[5-(2,4-Dimethoxy-benzyl)-1,1,4-trioxo-1,2,5-thiadiazolidin-2-ylmethyl]-benzyl}-carbamic acid t-butyl ester A solution of the title B compound in Example 9, 2-(2,4-dimethoxybenzyl)-1,1-dioxo-1,2,5-thiadiazolidin-3-one (742 mg, 2.59 mmol) and (4-hydroxymethyl-benzyl)-carbamic acid t-butyl ester (738 mg, 3.11 mmol) in THF (15 mL) is treated with triphenylphosphine (1.36 g, 5.18 mmol). The mixture is stirred for 10 min and diethyl azodicarboxylate (902 mg, 5.18 mmol) is added dropwise over 1 min. The mixture is stirred for 72 h. The solvent is evaporated and the residue is chromatographed on silica gel using 1% MeOH/$CH_2Cl_2$ as the eluent to afford {4-[5-(2,4-dimethoxy-benzyl)-1,1,4-trioxo-1,2,5-thiadiazolidin-2-ylmethyl]-benzyl}-carbamic acid t-butyl ester as a white solid: $[M+NH_4]^+=523$.

B. 5-(4-Aminomethyl-benzyl)-2-(2,4-dimethoxy-benzyl)-1,1-dioxo-1,2,5-thiadiazolidin-3-one hydrochloride The title A compound, {4-[5-(2,4-dimethoxy-benzyl)-1,1,4-trioxo-1,2,5-thiadiazolidin-2-ylmethyl]-benzyl}-carbamic acid t-butyl ester (400 mg, 0.79 mmol) is dissolved in EtOAc (20 mL) with gentle warming. The cooled solution is saturated with HCl gas and stirred for 30 min. The resulting precipitate is collected by filtration, washed with EtOAc and dried to give 5-(4-aminomethyl-benzyl)-2-(2,4-dimethoxy-benzyl)-1,1-dioxo-1,2,5-thiadiazolidin-3-one hydrochloride: $[M+1]^+=406$.

C. ({4-[5-(2,4-Dimethoxy-benzyl)-1,1,4-trioxo-1,2,5-thiadiazolidin-2-ylmethyl]-benzylcarbamoyl}-methyl)-carbamic acid t-butyl ester The title B compound, 5-(4-aminomethyl-benzyl)-2-(2,4-dimethoxy-benzyl)-1,1-dioxo-1,2,5-thiadiazolidin-3-one hydrochloride (89 mg, 0.20 mmol) is suspended in dry THF (10 mL) and N-Boc glycine (42 mg, 0.24 mmol) is added. EDCl (58 mg, 0.30 mmol) is added, followed by TEA (61 mg, 0.60 mmol). The mixture is stirred at RT for 16 h. The solvent is evaporated and the residue is chromatographed on silica gel using $CH_2Cl_2 \rightarrow$ 3% MeOH in $CH_2Cl_2$ as the eluent to afford ({4-[5-(2,4-dimethoxy-benzyl)-1,1,4-trioxo-1,2,5-thiadiazolidin-2-ylmethyl]-benzylcarbamoyl}-methyl)-carbamic acid t-butyl ester as a white solid: $[M+NH_4]^+= 580$.

D. 2-Amino-N-[4-(1,1,4-trioxo-1,2,5-thiadiazolidin-2-ylmethyl)-benzyl]-acetamide The title C compound, ({4-[5-(2,4-dimethoxy-benzyl)-1,1,4-trioxo-1,2,5-thiadiazolidin-2-ylmethyl]-benzylcarbamoyl}-methyl)-carbamic acid t-butyl ester (80 mg, 0.14 mmol) is stirred in equal volumes of $CH_2Cl_2$ and TFA (4 mL) for 16 h. The volatiles are evaporated and the residue is stirred in equal volumes of MeCN/water (5 mL) for 30 min. The mixture is filtered through a 0.2μ Acrodisc and the solvents are evaporated. The solid is washed with $Et_2O$ and dried to afford 2-amino-N-[4-(1,1,4-trioxo-1,2,5-thiadiazolidin-2-ylmethyl)-benzyl]-acetamide as a white solid: $[M-1]^-=311$.

EXAMPLE 32

5-(5-{1-[(E)-Hydroxyimino]-4-methyl-pentyl}-thiophen-2-ylmethyl)-1,1-dioxo-1,2,5-thiadiazolidin-3-one

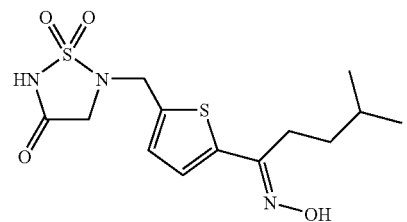

A. 5-(5-Diethoxymethyl-thiophen-2-ylmethyl)-2-(2,4-dimethoxy-benzyl)-1,1-dioxo-1,2,5-thiadiazolidin-3-one The title B compound in Example 9, 2-(2,4-dimethoxy-benzyl)-1,1-dioxo-1,2,5-thiadiazolidin-3-one (13.9 g, 48.5 mmol), (5-diethoxymethyl-thiophen-2-yl)-methanol (10.5 g, 48.5 mmol) and triphenylphosphine (19.1 g, 72.2 mmol) are dissolved in dry THF (300 mL) and the mixture is cooled to 0° C. Diethyl azodicarboxylate (12. g, 72.7 mmol) is added dropwise over 3 min and the mixture is stirred at RT for 16 h. The solvent is evaporated and the residue is taken up in $Et_2O$ (100 mL). The solution is cooled to 0° C. and the precipitate is filtered and discarded. The filtrate is concentrated to dryness and the residue is chromatographed on silica gel using 0→100% EtOAc in hexane as the eluent to afford 5-(5-diethoxymethyl-thiophen-2-ylmethyl)-2-(2,4-dimethoxy-benzyl)-1,1-dioxo-1,2,5-thiadiazolidin-3-one as an orange oil.

B. 5-[5-(2,4-Dimethoxy-benzyl)-1,1,4-trioxo-1,2,5-thiadiazolidin-2-ylmethyl]-thiophene-2-carbaldehyde The title A compound, 5-(5-diethoxymethyl-thiophen-2-ylmethyl)-2-(2,4-dimethoxy-benzyl)-1,1-dioxo-1,2,5-thiadiazolidin-3-one (3.91 g, 8.1 mmol) is dissolved in THF (100 mL) and 6N aqueous HCl (2.7 mL) is added. The mixture is stirred for 2 h and the solvent is evaporated. The residue is partitioned between EtOAc and saturated aqueous $NaHCO_3$ solution. The organic layer is dried over anhydrous $MgSO_4$ and concentrated to dryness. The residue is triturated from $Et_2O$ to afford 5-[5-(2,4-dimethoxy-benzyl)-1,1,4-trioxo-1,2,5-thiadiazolidin-2-ylmethyl]-thiophene-2-carbaldehyde as a yellow solid.

C. 2-(2,4-Dimethoxy-benzyl)-5-[5-(1-hydroxy-4-methyl-pentyl)-thiophen-2-ylmethyl]1,1-dioxo-1,2,5-thiadiazolidin-3-one A solution of the title B compound, 5-[5-(2,4-dimethoxy-benzyl)-1,1,4-trioxo-1,2,5-thiadiazolidin-2-ylmethyl]-thiophene-2-carbaldehyde (545 mg, 1.33 mmol) in dry THF (8 mL) is added dropwise to a cold (−70° C.) solution of isopentylmagnesium bromide (2.22 mmol) in dry THF (10 mL) keeping the temperature below −65° C. The mixture is stirred at −70° C. for 45 min and the reaction is quenched with saturated aqueous NH$_4$Cl solution. The mixture is diluted with EtOAc and the layers are separated. The organic layer is dried over anhydrous MgSO$_4$ and the solvent is evaporated. The residue is chromatographed on silica gel using 0→100% EtOAc in hexane as the eluent to afford 2-(2,4-dimethoxy-benzyl)-5-(5-(1-hydroxy-4-methyl-pentyl)-thiophen-2-ylmethyl]-1,1-dioxo-1,2,5-thiadiazolidin-3-one a yellow oil: [M+NH$_4$]$^+$=500.

D. 2-(2,4-Dimethoxy-benzyl)-5-[5-(4-methyl-pentanoyl)-thiophen-2-ylmethyl]-1,1-dioxo-1,2,5-thiadiazolidin-3-one The title C compound, 2-(2,4-dimethoxy-benzyl)-5-[5-(1-hydroxy-4-methyl-pentyl)-thiophen-2-ylmethyl]-1,1-dioxo-1,2,5-thiadiazolidin-3-one (125 mg, 0.26 mmol) is dissolved in THF (10 mL) and 4-methylmorpholine N-oxide (152 mg, 1.3 mmol) is added. Tetrapropylammonium perruthenate (TPAP, 9 mg, 0.026 mmol) is added and the mixture is stirred at RT for 1 h. The mixture is filtered through Celite and diluted with EtOAc. The solution is washed with 1N aqueous HCl and the organic layer is dried over anhydrous MgSO$_4$. The solvent is evaporated to afford 2-(2,4-dimethoxy-benzyl)-5-[5-(4-methyl-pentanoyl)-thiophen-2-ylmethyl]-1,1-dioxo-1,2,5-thiadiazolidin-3-one as a clear oil.

E. 2-(2,4-Dimethoxy-benzyl)-5-(5-{1-[-hydroxy-imino]-4-methyl-pentyl}-thiophen-2-ylmethyl)-1,1-dioxo-1,2,5-thiadiazolidin-3-one The title D compound, 2-(2,4-dimethoxy-benzyl)-5-[5-(4-methyl-pentanoyl)-thiophen-2-ylmethyl]-1,1-dioxo-1,2,5-thiadiazolidin-3-one (50 mg, 0.10 mmol) is dissolved in EtOH (5 mL) and water (1 mL) is added. Hydroxylamine hydrochloride (72 mg, 1.0 mmol) is added and the mixture is heated at reflux for 4 h. The solvent is evaporated and the residue is partitioned between EtOAc and water. The organic layer is dried over anhydrous MgSO$_4$ and concentrated to dryness to afford 2-(2,4-dimethoxy-benzyl)-5-(5-(1-[-hydroxyimino]-4-methyl-pentyl)-thiophen-2-ylmethyl)-1,1-dioxo-1,2,5-thiadiazolidin-3-one as a clear oil: [M+1]$^+$=496.

F. 5-(5-{1-[(E)-Hydroxyimino]-4-methyl-pentyl}-thiophen-2-ylmethyl)-1,1-dioxo-1,2,5-thiadiazolidin-3-one The title E compound, 2-(2,4-dimethoxy-benzyl)-5-(5-{1-[-hydroxyimino]-4-methyl-pentyl}-thiophen-2-ylmethyl)-1,1-dioxo-1,2,5-thiadiazolidin-3-one (40 mg, 0.08 mmol) is stirred in equal volumes of CH$_2$Cl$_2$ and TFA (4 mL) at RT for 3 h. The volatiles are evaporated and the residue is stirred in equal volumes of MeCN/water (5 mL) for 15 min. The mixture is filtered through a 0.2, Acrodisc and the solvents are evaporated to dryness. The residue is triturated from hexane/Et$_2$O (4:1) to afford 5-(5-{1-[(E)-hydroxyimino]-4-methyl-pentyl}-thiophen-2-ylmethyl)-1,1-dioxo-1,2,5-thiadiazolidin-3-one as a light pink solid: [M+1]$^+$=346.

EXAMPLE 33

4-(1,1,4-Trioxo-1,2,5-thiadiazolidin-2-ylmethyl) benzoic acid 4-carboxy-benzyl ester

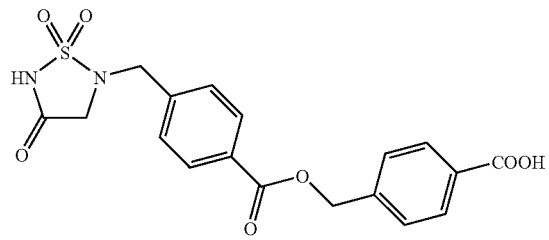

A. 4-[5-(2,4-Dimethoxy-benzyl)-1,1,4-trioxo-1,2,5-thiadiazolidin-2-ylmethyl]-benzoic acid benzyl ester To a solution of the title B compound in Example 9, 2-(2,4-dimethoxybenzyl)-1,1-dioxo-1,2,5-thiadiazolidin-3-one (2.0 g, 7.0 mmol) and 4-hydroxymethyl-benzoic acid benzyl ester (2.54 g, 10.5 mmol) in THF (50 mL) is added triphenylphosphine (3.67 g, 14 mmol) and the mixture is stirred until dissolved. The reaction is cooled to 0° C. and diethyl azodicarboxylate (2.20 mL, 14 mmol) dissolved in THF (20 mL) is added dropwise. The reaction is stirred for 16 h, while allowing to warm to RT, then concentrated. The residue is taken up in CH$_2$Cl$_2$, and chromatographed in two portions on a 110 g silica gel RediSep column (Isco, Inc.) with a 30 mL/min gradient elution of 0:100 (EtOAc:hexane) to 5:95 over 10 min. Fractions containing product are combined and concentrated to yield 4-[5-(2,4-dimethoxy-benzyl)-1,1,4-trioxo-1,2,5-thiadiazolidin-2-ylmethyl]-benzoic acid benzyl ester as a white solid.

B. 4-[5-(2,4-Dimethoxy-benzyl)-1,1,4-trioxo-1,2,5-thiadiazolidin-2-ylmethyl]-benzoic acid The title A compound, 4-[5-(2,4-dimethoxy-benzyl)-1,1,4-trioxo-1,2,5-thiadiazolidin-2-ylmethyl]-benzoic acid benzyl ester (2.04 g, 4.0 mmol) is suspended in EtOAc/EtOH (1:1, 100 mL) along with 10% palladium on carbon (300 mg) and treated with hydrogen (48 psi) for 4 h on a Parr Shaker. The reaction mixture is filtered through celite and concentrated to give a white solid which is recrystallized from MeOH to yield 4-[5-(2,4-dimethoxy-benzyl)-1,1,4-trioxo-1,2,5-thiadiazolidin-2-ylmethyl]-benzoic acid: [M-1]-=419.

C. 4-(1,1,4-Trioxo-1,2,5-thiadiazolidin-2-ylmethyl)-benzoic acid 4-t-butoxycarbonyl-benzyl ester A solution of the title B compound, 4-[5-(2,4-dimethoxy-benzyl)-1,1,4-trioxo-1,2,5-thiadiazolidin-2-ylmethyl]-benzoic acid (84 mg, 0.2 mmol) and 4-hydroxymethyl-benzoic acid t-butyl ester (42 mg, 0.2 mmol) in CH$_2$Cl$_2$ (3 mL) is treated with DMAP (12 mg, 0.1 mmol) and the reaction is cooled to 5° C. EDCl (39 mg, 0.2 mmol) is then added and the reaction is stirred for 16 h. The mixture is concentrated and partioned between EtOAc and 1N aqueous HCl. The organic solution is washed with saturated aqueous NaHCO$_3$ and brine, dried over anhydrous MgSO$_4$ and concentrated to give 4-(1,1,4-trioxo-1,2,5-thiadiazolidin-2-ylmethyl)-benzoic acid 4-t-butoxycarbonyl-benzyl ester as a white solid.

D. 4-(1,1,4-Trioxo-1,2,5-thiadiazolidin-2-ylmethyl)-benzoic acid 4-carboxy-benzyl ester The title C compound, 4-(1,1,4-trioxo-1,2,5-thiadiazolidin-2-ylmethyl)-benzoic acid 4-t-butoxycarbonyl-benzyl ester (119 mg, 0.19 mmol) is dissolved in CH$_2$Cl$_2$ (5 mL) and then added TFA (5 mL, 64.9 mmol). This is stirred for 2 h and then concentrated under reduced pressure. The residue is suspended in MeCN:water (6:4) (12 mL), centrifuged, decanted and filtered through a 0.1 micron Acrodisc filter. The resulting mixture is loaded onto a preparative reverse phase HPLC column (YMC CombiPrep Pro C18, 50×20 mm I.D., particle size S-5 micron, 12 nM) in 6 aliquots and eluted at 30 mL/min with a gradient of 90:10 (water containing 0.1% TFA: MeCN) at 0 min to 10:90 at 5 min. Then held at 10:90 until 7 min. Fractions containing product are combined and concentrated by lyophilization to yield 4-(1,1,4-trioxo-1,2,5-thiadiazolidin-2-ylmethyl)-benzoic acid 4-carboxy-benzyl ester as a white amorphous solid: [M−1]$^-$=403.

EXAMPLE 34

The following compounds are prepared using appropriate starting materials and general methods described in Examples 31, 32 and 33.

| Example | Chemical Name | MS [m/z] |
| --- | --- | --- |
| 34-1 | 1,1-Dioxo-5-(3-phenoxy-benzyl)-1,2,5-thiadiazolidin-3-one | [M − 1]$^-$ = 317 |
| 34-2 | 3-Nitro-4-(1,1,4-trioxo-1,2,5-thiadiazolidin-2-ylmethyl)-benzoic acid | [M − 1]$^-$ = 314 |
| 34-3 | 5-(4-Hydroxymethyl-benzyl)-1,1-dioxo-1,2,5-thiadiazolidin-3-one | [M − 1]$^-$ = 255 |
| 34-4 | 2-Amino-4-(1,1,4-trioxo-1,2,5-thiadiazolidin-2-ylmethyl)-benzoic acid methyl ester | (mp = 181–183° C.) |
| 34-5 | 5-(4-Hydroxy-benzyl)-1,1-dioxo-1,2,5-thiadiazolidin-3-one | [M − 1]$^-$ = 241 |
| 34-6 | 5-Nitro-2-(1,1,4-trioxo-1,2,5-thiadiazolidin-2-ylmethyl)-benzoic acid | [M − 1]$^-$ = 314 |
| 34-7 | 5-Amino-2-(1,1,4-trioxo-1,2,5-thiadiazolidin-2-ylmethyl)-benzoic acid | [M − 1]$^-$ = 284 |
| 34-8 | 5-(4-Chloro-3-methoxy-5-nitro-benzyl)-1,1-dioxo-1,2,5-thiadiazolidin-3-one | [M − 1]$^-$ = 334 |
| 34-9 | 5-(2-Nitro-benzyl)-1,1-dioxo-1,2,5-thiadiazolidin-3-one | [M − 1]$^-$ = 270 |
| 34-10 | 5-(3-Methyl-2-nitro-benzyl)-1,1-dioxo-1,2,5-thiadiazolidin-3-one | [M − 1]$^-$ = 284 |
| 34-11 | 5-(3-Methyl-benzyl)-1,1-dioxo-1,2,5-thiadiazolidin-3-one | [M − 1]$^-$ = 239 |
| 34-12 | 1,1-Dioxo-5-(3-phenyl-propyl)-1,2,5-thiadiazolidin-3-one | [M − 1]$^-$ = 253 |
| 34-13 | 5-(4-Butoxy-benzyl)-1,1-dioxo-1,2,5-thiadiazolidin-3-one | [M − 1]$^-$ = 297 |
| 34-14 | 1,1-Dioxo-5-(2-trifluoromethyl-benzyl)-1,2,5-thiadiazolidin-3-one | [M − 1]$^-$ = 293 |
| 34-15 | 3-Amino-4-(1,1,4-trioxo-1,2,5-thiadiazolidin-2-ylmethyl)-benzoic acid | [M − 1]$^-$ = 284 |
| 34-16 | 4-[5-Amino-2-(1,1,4-trioxo-1,2,5-thiadiazolidin-2-ylmethyl)-phenyl]-butyric acid | [M − 1]$^-$ = 326 |
| 34-17 | 5-(2-Methyl-3-nitro-benzyl)-1,1-dioxo-1,2,5-thiadiazolidin-3-one | [M − 1]$^-$ = 284 |
| 34-18 | 5-(4-Methyl-3-nitro-benzyl)-1,1-dioxo-1,2,5-thiadiazolidin-3-one | [M − 1]$^-$ = 284 |
| 34-19 | 5-(5-Methyl-2-nitro-benzyl)-1,1-dioxo-1,2,5-thiadiazolidin-3-one | [M − 1]$^-$ = 284 |
| 34-20 | 5-(2-Amino-benzyl)-1,1-dioxo-1,2,5-thiadiazolidin-3-one | [M − 1]$^-$ = 240 |
| 34-21 | 2-[4-(1,1,4-Trioxo-1,2,5-thiadiazolidin-2-ylmethyl)-benzyl]-isoindole-1,3-dione | [M − 1]$^-$ = 384 |
| 34-22 | 2-[3-(1,1,4-Trioxo-1,2,5-thiadiazolidin-2-ylmethyl)-benzyl]-isoindole-1,3-dione | [M − 1]$^-$ = 384 |
| 34-23 | 5,5'-[1,4-Phenylenebis(methylene)bis[1,2,5-thiadiazolidine-3-one], 1,1-dioxide | [M − 1]$^-$ = 373 |
| 34-24 | N-[2-(1,1,4-Trioxo-1,2,5-thiadiazolidin-2-ylmethyl)-phenyl]-oxalamic acid | [M − 1 ]$^-$ = 312 |
| 34-25 | 5-(3-Hydroxy-benzyl)-1,1-dioxo-1,2,5-thiadiazolidin-3-one | [M − 1]$^-$ = 241 |
| 34-26 | 2-Amino-4-(1,1,4-trioxo-1,2,5-thiadiazolidin-2-ylmethyl)-benzoic acid | [M − 1]$^-$ = 284 |
| 34-27 | 5-[5-(4-Nitro-phenyl)-furan-2-ylmethyl]-1,1-dioxo-1,2,5-thiadiazolidin-3-one | [M − 1]$^-$ = 336 |
| 34-28 | 5-(4-Fluoro-2-trifluoromethyl-benzyl)-1,1-dioxo-1,2,5-thiadiazolidin-3-one | [M − 1]$^-$ = 311 |
| 34-29 | 5-(3-Hydroxymethyl-benzyl)-1,1-dioxo-1,2,5-thiadiazolidin-3-one | [M − 1]$^-$ = 255 |
| 34-30 | 5-(3-Amino-5-hydroxymethyl-benzyl)-1,1-dioxo-1,2,5-thiadiazolidin-3-one | [M − 1]$^-$ = 270 |
| 34-31 | 5-(3-Amino-4-methyl-benzyl)-1,1-dioxo-1,2,5-thiadiazolidin-3-one | [M + H]$^+$ = 256 |
| 34-32 | 5-(2-Amino-3-methyl-benzyl)-1,1-dioxo-1,2,5-thiadiazolidin-3-one | [M + H]$^+$ = 256 |
| 34-33 | 5-(3-Amino-2-methyl-benzyl)-1,1-dioxo-1,2,5-thiadiazolidin-3-one | [M − 1]$^-$ = 254 |
| 34-34 | 5-(2-Amino-5-methyl-benzyl)-1,1-dioxo-1,2,5-thiadiazolidin-3-one | [M + H]$^+$ = 256 |
| 34-35 | 2,2,2-Trifluoro-N-[4-(1,1,4-trioxo-1,2,5-thiadiazolidin-2-ylmethyl)-benzyl]-acetamide | [M − 1]$^-$ = 350 |
| 34-36 | 4-(1,1,4-Trioxo-1,2,5-thiadiazolidin-2-ylmethyl)-pyridine-2-carbonitrile | [M − 1]$^-$ = 251 |
| 34-37 | 4-(1,1,4-Trioxo-1,2,5-thiadiazolidin-2-ylmethyl)-pyridine-2-carboxylic acid ethyl ester | [M − 1]$^-$ = 298 |

-continued

| Example | Chemical Name | MS [m/z] |
|---|---|---|
| 34-38 | 5-(3,4-Dimethoxy-benzyl)-1,1-dioxo-1,2,5-thiadiazolidin-3-one | [M − 1]⁻ = 285 |
| 34-39 | 5-(3-Amino-5-hydroxy-benzyl)-1,1-dioxo-1,2,5-thiadiazolidin-3-one | [M − 1]⁻ = 256 |
| 34-40 | 5-(3,5-Dimethyl-benzyl)-1,1-dioxo-1,2,5-thiadiazolidin-3-one | [M − 1]⁻ = 253 |
| 34-41 | (S)-3-Phenyl-2-[3-(1,1,4-trioxo-1,2,5-thiadiazolidin-2-ylmethyl)-benzylamino]-propionic acid ethyl ester | [M + H]⁺ = 432 |
| 34-42 | (S)-3-Phenyl-2-[4-(1,1,4-trioxo-1,2,5-thiadiazolidin-2-ylmethyl)-benzylamino]-propionic acid ethyl ester | [M − 1]⁻ = 430 |
| 34-43 | 2-Amino-5-(1,1,4-trioxo-1,2,5-thiadiazolidin-2-ylmethyl)-benzoic acid methyl ester | [M − 1]⁻ = 298 |
| 34-44 | 2-Acetylamino-4-(1,1,4-trioxo-1,2,5-thiadiazolidin-2-ylmethyl)-benzoic acid methyl ester | [M − 1]⁻ = 340 |
| 34-45 | 5-(2-Benzyl-benzyl)-1,1-dioxo-1,2,5-thiadiazolidin-3-one | [M − 1]⁻ = 315 |
| 34-46 | 5-(2,4-Bis-trifluoromethyl-benzyl)-1,1-dioxo-1,2,5-thiadiazolidin-3-one | [M − 1]⁻ = 361 |
| 34-47 | 1,1-Dioxo-5-(2,4,6-trifluoro-benzyl)-1,2,5-thiadiazolidin-3-one | [M − 1]⁻ = 279 |
| 34-48 | 5-(2-Bromo-benzyl)-1,1-dioxo-1,2,5-thiadiazolidin-3-one | [M − 1]⁻ = 303 |
| 34-49 | 5,5',-[[1,1'-biphenyl]-2,2'-diyl]bis(methylene)bis[1,2,5-Thiadiazolidine-3-one], 1,1-dioxide | [M − 1]⁻ = 449 |
| 34-50 | 5-(4-Ethylaminomethyl-benzyl)-1,1-dioxo-1,2,5-thiadiazolidin-3-one | [M + H]⁺ = 284 |
| 34-51 | 2-Acetylamino-4-(1,1,4-trioxo-1,2,5-thiadiazolidin-2-ylmethyl)-benzoic acid | [M − 1]⁻ = 326 |
| 34-52 | 2-Amino-4-(1,1,4-trioxo-1,2,5-thiadiazolidin-2-ylmethyl)-benzoic acid ethyl ester | [M − 1]⁻ = 312 |
| 34-53 | 1,1-Dioxo-5-[4-(phenethylamino-methyl)-benzyl]-1,2,5-thiadiazolidin-3-one | [M + H]⁺ = 360 |
| 34-54 | 5-(4-Diethylaminomethyl-benzyl)-1,1-dioxo-1,2,5-thiadiazolidin-3-one | [M + H]⁺ = 312 |
| 34-55 | 2-Amino-4-(1,1,4-trioxo-1,2,5-thiadiazolidin-2-ylmethyl)-benzoic acid benzyl ester | [M − 1]⁻ = 374 |
| 34-56 | N-Benzyl-4-(1,1,4-trioxo-1,2,5-thiadiazolidin-2-ylmethyl)-benzamide | [M − 1]⁻ = 358 |
| 34-57 | 5-(5-Dimethylaminomethyl-furan-2-ylmethyl)-1,1-dioxo-1,2,5-thiadiazolidin-3-one | [M + H]⁺ = 274 |
| 34-58 | N-[2-(3-Trifluoromethyl-phenyl)-ethyl]-4-(1,1,4-trioxo-1,2,5-thiadiazolidin-2-ylmethyl)-benzamide | [M − 1]⁻ = 440 |
| 34-59 | N-(3-Methyl-butyl)-4-(1,1,4-trioxo-1,2,5-thiadiazolidin-2-ylmethyl)-benzamide | [M + CH₄CN⁺]⁺ = 381 |
| 34-60 | (S)-3-Phenyl-2-(1,1,4-trioxo-1,2,5-thiadiazolidin-2-yl)-propionic acid | [M − 1]⁻ = 283 |
| 34-61 | (R)-3-Phenyl-2-(1,1,4-trioxo-1,2,5-thiadiazolidin-2-yl)-propionic acid | [M − 1]⁻ = 283 |
| 34-62 | 4-(1,1,4-Trioxo-1,2,5-thiadiazolidin-2-ylmethyl)-benzoic acid benzyl ester | [M − 1]⁻ = 359 |
| 34-63 | [4-(1,1,4-Trioxo-1,2,5-thiadiazolidin-2-ylmethyl)-phenoxy]-acetic acid | [M − 1]⁻ = 299 |
| 34-64 | 4-(1,1,4-Trioxo-1,2,5-thiadiazolidin-2-ylmethyl)-benzoic acid isobutyl ester | [M − 1]⁻ = 325 |
| 34-65 | 2-Amino-4-(1,1,4-trioxo-1,2,5-thiadiazolidin-2-ylmethyl)-benzoic acid isobutyl ester | [M − 1]⁻ = 340 |
| 34-66 | [4-(1,1,4-Trioxo-1,2,5-thiadiazolidin-2-ylmethyl)-phenoxy]-acetic acid methyl ester | [M − 1]⁻ = 313 |
| 34-67 | 4-(1,1,4-Trioxo-1,2,5-thiadiazolidin-2-ylmethyl)-benzoic acid 4-carboxymethoxy-benzyl ester | [M − 1]⁻ = 433 |
| 34-68 | 5-(5-Aminomethyl-thiophen-2-ylmethyl)-1,1-dioxo-1,2,5-thiadiazolidin-3-one | [M − 1]⁻ = 260 |
| 34-69 | 4-{2-[4-(1,1,4-Trioxo-1,2,5-thiadiazolidin-2-ylmethyl)-benzylamino]-ethyl}-benzoic acid | [M + H]⁺ = 404 |
| 34-70 | [4-(1,1,4-Trioxo-1,2,5-thiadiazolidin-2-ylmethyl)-phenoxy]-acetic acid isobutyl ester | [M − 1]⁻ = 355 |
| 34-71 | [4-(1,1,4-Trioxo-1,2,5-thiadiazolidin-2-ylmethyl)-phenoxy]-acetic acid benzyl ester | [M − 1]⁻ = 389 |
| 34-72 | N-Isobutyl-4-(1,1,4-trioxo-1,2,5-thiadiazolidin-2-ylmethyl)-benzamide | [M − 1]⁻ = 324 |
| 34-73 | 5-(5-Diethylaminomethyl-thiophen-2-ylmethyl)-1,1-dioxo-1,2,5-thiadiazolidin-3-one | [M + H]⁺ = 318 |
| 34-74 | 4-(2-{[5-(1,1,4-Trioxo-1,2,5-thiadiazolidin-2-ylmethyl)-thiophen-2-ylmethyl]-amino}-ethyl)-benzoic acid | [M + H]⁺ = 410 |
| 34-75 | 3-Nitro-4-(1,1,4-trioxo-1,2,5-thiadiazolidin-2-ylmethyl)-benzoic acid methyl ester | [M − 1]⁻ = 328 |
| 34-76 | 3-Nitro-4-(1,1,4-trioxo-1,2,5-thiadiazolidin-2-ylmethyl)-benzoic acid ethyl ester | [M − 1]⁻ = 342 |
| 34-77 | 3-Nitro-4-(1,1,4-trioxo-1,2,5-thiadiazolidin-2-ylmethyl)-benzoic acid isobutyl ester | [M − 1]⁻ = 370 |
| 34-78 | 5-(4-Ethoxy-benzyl)-1,1-dioxo-1,2,5-thiadiazolidin-3-one | [M − 1]⁻ = 269 |
| 34-79 | 1,1-Dioxo-5-(3-trifluoromethyl-benzyl)-1,2,5-thiadiazolidin-3-one | [M − 1]⁻ = 293 |

-continued

| Example | Chemical Name | MS [m/z] |
|---|---|---|
| 34-80 | 4-(1,1,4-Trioxo-1,2,5-thiadiazolidin-2-ylmethyl)-benzoic acid 4-carboxymethyl-benzyl ester | [M − 1]⁻ = 417 |
| 34-81 | 4-(1,1,4-Trioxo-1,2,5-thiadiazolidin-2-ylmethyl)-benzoic acid phenethyl ester | [M − 1]⁻ = 373 |
| 34-82 | 4-(1,1,4-Trioxo-1,2,5-thiadiazolidin-2-ylmethyl)-benzoic acid 2-phenylamino-ethyl ester | [M − 1]⁻ = 388 |
| 34-83 | 4-(1,1,4-Trioxo-1,2,5-thiadiazolidin-2-ylmethyl)-benzoic acid 2-(3-methoxy-phenyl)-ethyl ester | [M − 1]⁻ = 403 |
| 34-84 | 4-(1,1,4-Trioxo-1,2,5-thiadiazolidin-2-ylmethyl)-benzoic acid 4-(1,1,4-trioxo-1,2,5-thiadiazolidin-2-ylmethyl)-benzyl ester | [M − 1]⁻ = 507 |
| 34-85 | 4-(1,1,4-Trioxo-1,2,5-thiadiazolidin-2-ylmethyl)-benzoic acid 2,2-dimethyl-propyl ester | [M − 1]⁻ = 339 |
| 34-86 | 4-(1,1,4-Trioxo-1,2,5-thiadiazolidin-2-ylmethyl)-benzoic acid 2-methoxycarbonyl-2-methyl-propyl ester | [M − 1]⁻ = 383 |
| 34-87 | 4-(1,1,4-Trioxo-1,2,5-thiadiazolidin-2-ylmethyl)-benzoic acid 2,2,4-trimethyl-pentyl ester | [M − 1]⁻ = 381 |
| 34-88 | 4-(1,1,4-Trioxo-1,2,5-thiadiazolidin-2-ylmethyl)-benzoic acid 3-dimethylamino-2,2-dimethyl-propyl ester | [M − 1]⁻ = 382 |
| 34-89 | 4-(1,1,4-Trioxo-1,2,5-thiadiazolidin-2-ylmethyl)-benzoic acid (3aR,4S,5R,6aS)-5-benzoyloxy-2-oxo-hexahydro-cyclopenta[b]furan-4-ylmethyl ester | [M − 1]⁻ = 527 |
| 34-90 | 6-{[5-(1,1,4-Trioxo-1,2,5-thiadiazolidin-2-ylmethyl)-thiophen-2-ylmethyl]-amino}-hexanoic acid | [M + H]⁺ = 376 |
| 34-91 | 5-{5-[(3-Methyl-butylamino)-methyl]-thiophen-2-ylmethyl}-1,1-dioxo-1,2,5-thiadiazolidin-3-one | [M + H]⁺ = 332 |
| 34-92 | 4-(1,1,4-Trioxo-1,2,5-thiadiazolidin-2-ylmethyl)-benzoic acid 3-methyl-4-nitro-benzyl ester | [M − 1]⁻ = 418 |
| 34-93 | 4-(1,1,4-Trioxo-1,2,5-thiadiazolidin-2-ylmethyl)-benzoic acid 3-chloro-4-methyl-benzyl ester | [M − 1]⁻ = 407 |
| 34-94 | 5-[5-(Isobutylamino-methyl)-thiophen-2-ylmethyl]-1,1-dioxo-1,2,5-thiadiazolidin-3-one | [M + H]⁺ = 318 |
| 34-95 | 4-(1,1,4-Trioxo-1,2,5-thiadiazolidin-2-ylmethyl)-benzoic acid 5-ethoxycarbonyl-pentyl ester | [M − 1]⁻ = 411 |
| 34-96 | 4-(1,1,4-Trioxo-1,2,5-thiadiazolidin-2-ylmethyl)-benzoic acid 2-(3-chloro-phenyl)-ethyl ester | [M − 1]⁻ = 407 |
| 34-97 | 4-(1,1,4-Trioxo-1,2,5-thiadiazolidin-2-ylmethyl)-benzoic acid 2-m-tolyl-ethyl ester | [M − 1]⁻ = 387 |
| 34-98 | 4-(1,1,4-Trioxo-1,2,5-thiadiazolidin-2-ylmethyl)-benzoic acid 2-(3-trifluoromethyl-phenyl)-ethyl ester | [M − 1]⁻ = 441 |
| 34-99 | (R)-3-Phenyl-2-[4-(1,1,4-trioxo-1,2,5-thiadiazolidin-2-ylmethyl)-benzylamino]-propionic acid ethyl ester | [M − 1]⁻ = 430 |
| 34-100 | 5-[4-(Benzylamino-methyl)-benzyl]-1,1-dioxo-1,2,5-thiadiazolidin-3-one | [M − 1]⁻ = 344 |
| 34-101 | 4-(1,1,4-Trioxo-1,2,5-thiadiazolidin-2-ylmethyl)-benzoic acid 4-methyl-benzyl ester | [M − 1]⁻ = 373 |
| 34-102 | 4-Methyl-6-{[5-(1,1,4-trioxo-1,2,5-thiadiazolidin-2-ylmethyl)-thiophen-2-ylmethyl]-amino}-hexanoic acid | [M − 1]⁻ = 388 |
| 34-103 | 4-[(1,1,4-trioxido-1,2,5-thiadiazolidin-2-yl)methyl]-benzoic acid [4-(methoxycarbonyl)phenyl]methyl ester | [M − 1]⁻ = 417 |
| 34-104 | 4-(1,1,4-Trioxo-1,2,5-thiadiazolidin-2-ylmethyl)-benzoic acid 2-cyclohexyl-2-methyl-propyl ester | [M − 1]⁻ = 407 |
| 34-105 | 4-(1,1,4-Trioxo-1,2,5-thiadiazolidin-2-ylmethyl)-benzoic acid 2-phenoxy-propyl ester | [M − 1]⁻ = 403 |
| 34-106 | 4-(1,1,4-Trioxo-1,2,5-thiadiazolidin-2-ylmethyl)-benzoic acid 4-trifluoromethyl-benzyl ester | [M − 1]⁻ = 427 |
| 34-107 | 4-(1,1,4-Trioxo-1,2,5-thiadiazolidin-2-ylmethyl)-benzoic acid 3-trifluoromethyl-benzyl ester | [M − 1]⁻ = 427 |
| 34-108 | 4-[(1,1,4-trioxido-1,2,5-thiadiazolidin-2-yl)methyl]-benzoic acid 2-(4-carboxyphenyl)ethyl ester | [M − 1]⁻ = 417 |
| 34-109 | 5-[5-(3-Methyl-butyryl)-thiophen-2-ylmethyl]-1,1-dioxo-1,2,5-thiadiazolidin-3-one | [M − 1]⁻ = 315 |
| 34-110 | 3-[[[4-[(1,1,4-Trioxido-1,2,5-thiadiazolidin-2-yl)methyl]benzoyl]-oxy]methyl]benzoic acid | [M − 1]⁻ = 403 |
| 34-111 | 5-[4-(Isobutylamino-methyl)-benzyl]-1,1-dioxo-1,2,5-thiadiazolidin-3-one | [M − 1]⁻ = 310 |
| 34-112 | 5-{4-[(2,2-Dimethyl-propylamino)-methyl]-benzyl}-1,1-dioxo-1,2,5-thiadiazolidin-3-one | [M − 1]⁻ = 324 |
| 34-113 | 4-(1,1,4-Trioxo-1,2,5-thiadiazolidin-2-ylmethyl)-benzoic acid naphthalen-1-ylmethyl ester | [M − 1]⁻ = 409 |
| 34-114 | 4-(1,1,4-Trioxo-1,2,5-thiadiazolidin-2-ylmethyl)-benzoic acid 4-nitro-benzyl ester | [M − 1]⁻ = 404 |

-continued

| Example | Chemical Name | MS [m/z] |
|---|---|---|
| 34-115 | (4-{2-[4-(1,1,4-Trioxo-1,2,5-thiadiazolidin-2-ylmethyl)-benzoylamino]-ethyl}-phenyl)-acetic acid | $[M + H]^+ = 432$ |
| 34-116 | 5-[5-(4-Methyl-pentanoyl)-thiophen-2-ylmethyl]-1,1-dioxo-1,2,5-thiadiazolidin-3-one | $[M - 1]^- = 329$ |
| 34-117 | 5-(1,1,4-Trioxo-1,2,5-thiadiazolidin-2-ylmethyl)-thiophene-2-carboxylic acid | $[M - 1]^- = 275$ |
| 34-118 | 4-(1,1,4-Trioxo-1,2,5-thiadiazolidin-2-ylmethyl)-benzoic acid 3-nitro-benzyl ester | $[M - 1]^- = 404$ |
| 34-119 | 4-(1,1,4-Trioxo-1,2,5-thiadiazolidin-2-ylmethyl)-benzoic acid 3-(carboxymethyl-amino)-2,2-dimethyl-propyl ester | $[M - 1]^- = 412$ |
| 34-120 | 5-[4-(1,1,4-Trioxo-1,2,5-thiadiazolidin-2-ylmethyl)-benzoyloxymethyl]-thiophene-2-carboxylic acid | $[M - 1]^- = 409$ |
| 34-121 | 5-[4-(4-Benzyl-piperazin-1-ylmethyl)-benzyl]-1,1-dioxo-1,2,5-thiadiazolidin-3-one | $[M - 1]^- = 413$ |
| 34-122 | 4-(1,1,4-Trioxo-1,2,5-thiadiazolidin-2-ylmethyl)-benzoic acid biphenyl-4-ylmethyl ester | $[M - 1]^- = 435$ |
| 34-123 | 4-(1,1,4-Trioxo-1,2,5-thiadiazolidin-2-ylmethyl)-benzoic acid 4-acetylamino-benzyl ester | $[M - 1]^- = 416$ |
| 34-124 | 4-(1,1,4-Trioxo-1,2,5-thiadiazolidin-2-ylmethyl)-benzoic acid 2-benzyl-benzyl ester | $[M - 1]^- = 449$ |
| 34-125 | 4-(1,1,4-Trioxo-1,2,5-thiadiazolidin-2-ylmethyl)-benzoic acid 2-methyl-benzyl ester | $[M - 1]^- = 373$ |
| 34-126 | 4-(1,1,4-Trioxo-1,2,5-thiadiazolidin-2-ylmethyl)-benzoic acid 2-methyl-3-nitro-benzyl ester | $[M - 1]^- = 418$ |
| 34-127 | Glycine, N-(aminosulfonyl)-N-[[4-[[(2-phenylethyl)thio]methyl]-phenyl]methyl]-, methyl ester | $[M - 1]^- = 407$ |
| 34-128 | 4-(1,1,4-Trioxo-1,2,5-thiadiazolidin-2-ylmethyl)-benzoic acid 3-carboxymethyl-benzyl ester | $[M - 1]^- = 417$ |
| 34-129 | 4-(1,1,4-Trioxo-1,2,5-thiadiazolidin-2-ylmethyl)-benzoic acid 4-methyl-3-nitro-benzyl ester | $[M - 1]^- = 418$ |
| 34-130 | 4-(1,1,4-Trioxo-1,2,5-thiadiazolidin-2-ylmethyl)-benzoic acid 4-fluoro-2-trifluoromethyl-benzyl ester | $[M - 1]^- = 445$ |
| 34-131 | 4-[5-(2,4-Dimethoxy-benzyl)-1,1,4-trioxo-1,2,5-thiadiazolidin-2-ylmethyl]-benzoic acid 4-(1,1,4-trioxo-1,2,5-thiadiazolidin-2-yl)-benzyl ester | $[M - 1]^- = 643$ |
| 34-132 | 4-(1,1,4-Trioxo-1,2,5-thiadiazolidin-2-ylmethyl)-benzoic acid 4-(1,1,4-trioxo-1,2,5-thiadiazolidin-2-yl)-benzyl ester | $[M - 1]^- = 493$ |
| 34-133 | 4-(1,1,4-Trioxo-1,2,5-thiadiazolidin-2-ylmethyl)-benzoic acid 5-methyl-2-nitro-benzyl ester | $[M - 1]^- = 418$ |
| 34-134 | 4-(1,1,4-Trioxo-1,2,5-thiadiazolidin-2-ylmethyl)-benzoic acid o-tolyl ester | $[M - 1]^- = 359$ |
| 34-135 | 4-(1,1,4-Trioxo-1,2,5-thiadiazolidin-2-ylmethyl)-benzoic acid 3-(carboxymethyl-methyl-amino)-2,2-dimethyl-propyl ester | $[M - 1]^- = 426$ |
| 34-136 | 4-(1,1,4-Trioxo-1,2,5-thiadiazolidin-2-ylmethyl)-benzoic acid phenyl ester | $[M - 1]^- = 345$ |
| 34-137 | 4-(1,1,4-Trioxo-1,2,5-thiadiazolidin-2-ylmethyl)-benzoic acid 5-isobutylcarbamoyl-thiophen-2-ylmethyl ester | $[M - 1]^- = 464$ |
| 34-138 | 4-(1,1,4-Trioxo-1,2,5-thiadiazolidin-2-ylmethyl)-benzoic acid naphthalen-2-ylmethyl ester | $[M - 1]^- = 409$ |
| 34-139 | N,N-Diisobutyl-4-(1,1,4-trioxo-1,2,5-thiadiazolidin-2-ylmethyl)-benzamide | $[M + H]^+ = 382$ |
| 34-140 | {4-[4-(1,1,4-Trioxo-1,2,5-thiadiazolidin-2-ylmethyl)-benzoyl]-piperazin-1-yl}-acetic acid | $[M + H]^+ = 397$ |
| 34-141 | 4-(1,1,4-Trioxo-1,2,5-thiadiazolidin-2-ylmethyl)-benzoic acid naphthalen-2-yl ester | $[M - 1]^- = 395$ |
| 34-142 | 5-[4-(1,1,4-Trioxo-1,2,5-thiadiazolidin-2-ylmethyl)-benzoyloxymethyl]-thiophene-2-carboxylic acid isobutyl ester | $[M - 1]^- = 465$ |
| 34-143 | 4-(1,1,4-Trioxo-1,2,5-thiadiazolidin-2-ylmethyl)-benzoic acid 5-carbamoyl-thiophen-2-ylmethyl ester | $[M - 1]^- = 408$ |
| 34-144 | 5-[4-(4-Benzyl-piperazine-1-carbonyl)-benzyl]-1,1-dioxo-1,2,5-thiadiazolidin-3-one | $[M - 1]^- = 427$ |
| 34-145 | 4-(1,1,4-Trioxo-1,2,5-thiadiazolidin-2-ylmethyl)-benzoic acid 5-(3-phenyl-propionyl)-thiophen-2-ylmethyl ester | $[M - 1]^- = 497$ |
| 34-146 | 4-(1,1,4-Trioxo-1,2,5-thiadiazolidin-2-ylmethyl)-benzoic acid 5-benzylcarbamoyl-thiophen-2-ylmethyl ester | $[M - 1]^- = 498$ |

EXAMPLE 35

1,1-Dioxo-5-phenyl-1,2,5-thiadiazolidin-3-one sodium salt

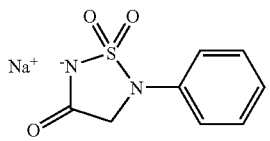

A. N-sulfamoylated-N-phenylglycine ethyl ester

A solution N-phenylglycine ethyl ester (1.0 g, 5.58 mmol) and TEA (1.69 g, 16.7 mmol) in MeCN, 3 mL is added dropwise to a freshly prepared solution of sulfamoyl chloride (5.58 mmol) in MeCN (5 mL) over 20 min. The mixture is stirred at room temperature (RT) for 16 h. The solvent is evaporated and the residue is partitioned between EtOAc and water. The organic layer is dried over anhydrous sodium sulfate ($Na_2SO_4$) and evaporated. The residue is flash chromatographed on silica gel using 30%→50% EtOAc in hexanes as eluent to afford the N-sulfamoylated-N-phenylglycine ethyl ester as a yellow solid: $[M+1]^+=259$.

B. 1,1-Dioxo-5-phenyl-1,2,5-thiadiazolidin-3-one sodium salt

A solution of the title A compound, N-sulfamoyl-N-phenylglycine ethyl ester (23 mg, 0.089 mmol) in EtOH is treated with 1N aqueous sodium hydroxide (NaOH, 0.089 mL, 0.089 mmol) and the mixture is stirred at RT for 3 h. The mixture is evaporated to dryness to afford 1,1-dioxo-5-phenyl-1,2,5-thiadiazolidin-3-one sodium salt as a white solid: $[M-1]^-=211$.

EXAMPLE 36

5-(2,4-Diaminophenyl)-1,1-dioxo-1,2,5-thiadiazolidin-3-one

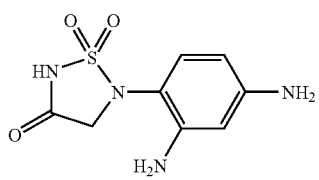

A. Glycine-N-sulfonic acid 2,4-dimethoxybenzylamide

Glycine methyl ester-N-sulfonic acid 2,4-dimethoxybenzylamide (14.9 g, 47.0 mmol), is prepared analogously to the literature procedure as described by Ducry, L.; Reinelt, S.; Seiler, P.; Diederich, F. *Helvetica Chimica. Acta.* 1999, 82, 2432-47, and is dissolved in 100 mL of 1,4-dioxane, then 94 mL of 1N aqueous NaOH solution is added. After 120 minutes, the 1,4-dioxane is evaporated in vacuo, and the remaining aqueous solution is extracted with diethyl ether. The aqueous solution is acidified with 1N aqueous HCl solution and extracted with EtOAc two times. The organic layer is dried over anhydrous magnesium sulfate ($MgSO_4$), filtered and evaporated to dryness giving glycine-N-sulfonic acid 2,4-dimethoxybenzylamide: $[M-1]^-=303$.

B. 2-(2,4-Dimethoxybenzyl)-1,1-dioxo-1,2,5-thiadiazolidin-3-one

The title A compound, glycine-N-sulfonic acid 2,4-dimethoxybenzylamide (14.3 g, 47.0 mmol) is dissolved in 300 mL of THF, then hydroxybenzotriazole (HOBt, 7.20 g, 47.0 mmol) is added as a solid and stirred until dissolved. EDCl (9.01 g, 47.0 mmol) is added as a solid and stirred for 10 min, followed by the addition of TEA (7.20 mL, 51.7 mmol). The reaction is stirred for 16 h, then evaporated under vacuo. The residue is partitioned between 1N aqueous HCl solution and EtOAc. The organic layer is dried over anhydrous $MgSO_4$ and concentrated to give an oil which solidified on standing. This is dissolved in hot EtOAc and flash chromatographed on silica gel with 40% EtOAc in hexanes to afford 2-(2,4-dimethoxybenzyl)-1,1-dioxo-1,2,5-thiadiazolidin-3-one as a white solid: $[M-1]^-=285$.

C. 2-(2,4-Dimethoxybenzyl)-5-(2,4-dinitrophenyl)-1,1-dioxo-1,2,5-thiadiazolidin-3-one A solution of the title B compound, 2-(2,4-dimethoxybenzyl)-1,1-dioxo-1,2,5-thiadiazolidin-3-one (303 mg, 1.05 mmol) in dry 1,4-dioxane (5 mL) is treated with $Cs_2CO_3$ (342 mg, 1.05 mmol). 1-Fluoro-2,4-dinitrobenzene (197 mg, 1.05 mmol) is added and the mixture is stirred at RT for 16 h. The solvent is evaporated and the residue is partitioned between EtOAc and 1N aqueous HCl. The organic layer is dried over anhydrous $Na_2SO_4$ and concentrated. The residue is chromatographed on silica gel using 10%→100% EtOAc in hexanes as the eluent to afford 2-(2,4-dimethoxybenzyl)-5-(2,4-dinitrophenyl)-1,1-dioxo-1,2,5-thiadiazolidin-3-one as a yellow solid: $[M-1]^-=451$.

D. 2-(2,4-Dimethoxybenzyl)-5-(2,4-diaminophenyl)-1,1-dioxo-1,2,5-thiadiazolidin-3-one A mixture of the title C compound, 2-(2,4-dimethoxybenzyl)-5-(2,4-dinitrophenyl)-1,1-dioxo-1,2,5-thiadiazolidin-3-one (200 mg, 4.42 mmol) in 20 mL of MeOH/EtOAc (3:1) and 10% palladium on carbon (100 mg) is shaken under hydrogen atmosphere at 40 psi for 1 h. The catalyst is removed by filtration and the solvents are evaporated to afford 2-(2,4-dimethoxy-benzyl)-5-(2,4-diaminophenyl)-1,1-dioxo-1,2,5-thiadiazolidin-3-one as a brown solid: $[M+1]^+=393$.

E. 5-(2,4-Diaminophenyl)-1,1-dioxo-1,2,5-thiadiazolidin-3-one

A solution of the title D compound, 2-(2,4-dimethoxybenzyl)-5-(2,4-diaminophenyl)-1,1-dioxo-1,2,5-thiadiazolidin-3-one (40 mg, 0.10 mmol) is stirred in 4 mL of TFA/$CH_2Cl_2$ (1:1) at RT for 16 h. The volatiles are evaporated and the residue is stirred in 4 mL of MeCN/water (1:1) for 20 min. The mixture is filtered through a 0.2 μM Acrodisc and the solvents are evaporated. The residue is triturated from diethylether ($Et_2O$) to give 5-(2,4-diaminophenyl)-1,1-dioxo-1,2,5-thiadiazolidin-3-one TFA salt as a brown solid: $[M+1]^+=243$.

Beispiel 2

EXAMPLE 37

3-(1,1,4-Trioxo-1,2,5-thiadiazolidin-2-yl)benzoic acid methyl ester

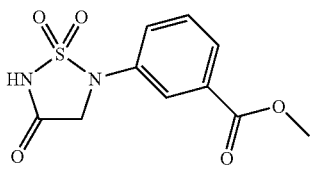

A. 3-[5-(2,4-Dimethoxybenzyl)-1,1,4-trioxo-1,2,5-thiadiazolldin-2-yl]benzoic acid methyl ester A solution of the title B compound in Example 36, 2-(2,4-dimethoxybenzyl)-1,1-dioxo-1,2,5-thiadiazolidin-3-one (115 mg, 4.02 mmol) and 3-methoxycarbonyl phenylboronic acid (145 mg, 8.04 mmol) in 1,4-dioxane (5 mL) is treated with copper(II) acetate (110 mg, 6.03 mmol) and $CS_2CO_3$ (262 mg, 8.04 mmol). The mixture is stirred at RT for 16 h and the solvent is evaporated. The residue is partitioned between EtOAc and 1N aqueous HCl. The organic layer is dried over anhydrous $Na_2SO_4$ and concentrated. The residue is flash chromatographed on silica gel using 30% EtOAc in hexanes as the eluent to give 3-[5-(2,4-dimethoxybenzyl)-1,1,4-trioxo-1,2,5-thiadiazolidin-2-yl]benzoic acid methyl ester as a clear oil: $[M+NH_4]^+=438$.

B. 3-(1,1,4-Trioxo-1,2,5-thiadiazolidin-2-yl)benzoic acid methyl ester

A solution of the title A compound, 3-[5-(2,4-dimethoxybenzyl)-1,1,4-trioxo-1,2,5-thiadiazolidin-2-yl]benzoic acid methyl ester is stirred in 2 mL of $TFA/CH_2Cl_2$ (1:1) at RT for 16 h. The volatiles are evaporated and the residue is stirred in 4 mL of MeCN/water (1:1) for 20 min. The mixture is filtered through a 0.2 µM Acrodisc and evaporated. The residue is triturated from $Et_2O$ at −50° C. to give 3-(1,1,4-trioxo-1,2,5-thiadiazolidin-2-yl)benzoic acid methyl ester as a pink solid: $[M-1]^-=269$.

EXAMPLE 38

3-(1,1,4-Trioxo-1,2,5-thiadiazolidin-2-yl)-benzoic acid

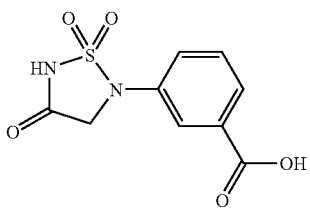

A solution of sodium hydroxide (105.4 mg, 2.64 mmol) in water (2.54 g) is added to a solution of the Example 37 title compound, 3-(1,1,4-Trioxo-1,2,5-thiadiazolidin-2-yl)-benzoic acid methyl ester (37.1 mg, 0.137 mmol) in MeOH (5.48 mL). This is allowed to stir 13 h and then neutralized by addition of 1N aqueous HCl (2.64 mL). The reaction mixture is loaded onto a preparative reverse phase HPLC column (YMC CombiPrep Pro C18, 50×20 mm I.D., particle size S-5 micron, 12 nM) in two equal aliquots and eluted at 30 mL/min with a gradient of 100:0 (water containing 0.1% TFA: MeCN) for 0 min to 2.5 min, then to 10:90 at 5.5 min. Then held at 10:90 until 7 min. Fractions containing the product are combined and concentrated on a Savant Speed-vac to yield 3-(1,1,4-trioxo-1,2,5-thiadiazolidin-2-yl)-benzoic acid as a white powder: API-Ms $[M-H]=255.09$.

EXAMPLE 39

5-(4-Aminomethyl phenyl)-1,1-dioxo-1,2,5-thiadiazolidin-3-one

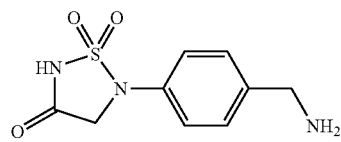

The title compound is prepared analogously to Example 3: $[M-1]^-=240$.

EXAMPLE 40

[2-(1,1,4-Trioxo-1,2,5-thiadiazolidin-2-yl)-phenyl]-acetic acid methyl ester

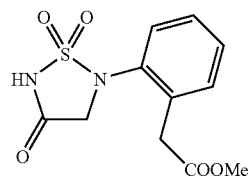

A. (2-Nitro-phenyl)-acetic acid methyl ester (2-Nitro-phenyl)-acetic acid (10.93 g, 60.3 mmol) is dissolved in MeOH (200 mL) and HCl gas is bubbled through the solution for 10 min. The reaction is stirred capped for 18 h, then concentrated under reduced pressure to yield (2-nitro-phenyl)-acetic acid methyl ester as a yellow oil.

B. (2-Amino-phenyl) acetic acid methyl ester

The title A compound, (2-nitro-phenyl)-acetic acid methyl ester (5.0 g, 25.6 mmol) is dissolved in MeOH (125 mL) in a Parr Bottle. It is purged with nitrogen, then added $PtO_2$ (185 mg), then placed on a Parr Shaker under 50 to 55 psi of hydrogen with shaking for 25.5 h. The reaction is opened and filtered through celite, and concentrated to yield (2-amino-phenyl) acetic acid methyl ester as an amber oil: $[M+1]^+=166$.

C. [2-(t-Butoxycarbonylmethyl-amino)-phenyl]-acetic acid methyl ester

The title B compound, (2-amino-phenyl) acetic acid methyl ester (4.2 g, 25.4 mmol) is dissolved in DMF (30 mL). Powdered potassium carbonate (8.78 g, 63.5 mmol) and t-butyl bromoacetate (4.12 mL, 27.9 mmol) are added and the reaction is stirred at room temperature for 18 h and then at 50° C. for 1 h. The reaction is diluted with water (300 mL) and extracted with EtOAc (2×200 mL). Combined EtOAc layers are washed with water (2×100 mL) then brine (100 mL), dried over anhydrous MgSO$_4$, filtered and concentrated to give a viscous brown oil. This residue is chromatographed on a 110 g silica gel RediSep (Isco Inc.) column with a 30 mL/min gradient elution of 10:90 (EtOAc: hexane) to 25:75 over 30 min. Fractions containing product are combined and evaporated to yield [2-(t-butoxy-carbonylmethyl-amino)-phenyl]-acetic acid methyl ester as a clear amber oil: [M+1]$^+$=280.

D. N-(t-Butoxycarbonyl-sulfamoyl)-N-[2-(methoxycarbonylmethyl)-phenyl]-glycine t-butyl ester Chlorosulfonylisocyanate (1.42 mL, 16.4 mmol) is added to CH$_2$Cl$_2$ (20 mL) in a dry flask under argon balloon, and cooled with stirring in an ice/salt/water bath. t-Butanol (1.57 mL, 16.4 mmol) is added to this solution and stirred while maintaining the cooling for 1 h. Then a solution of the title C compound, [2-(t-butoxycarbonylmethyl-amino)-phenyl]-acetic acid methyl ester (3.84 g, 13.7 mmol) and TEA (5.7 mL, 41.1 mmol) in CH$_2$Cl$_2$ (90 mL) is rapidly cannulated into this above mentioned stirred, cooled solution. During 18 h the reaction slowly warms to RT, then concentrated and partitioned between EtOAc and 0.5N aqueous HCl (2×50 mL). The organic solution is washed with brine (25 mL), dried over anhydrous MgSO$_4$, filtered and concentrated. The resulting residue is chromatographed on a 110 g silica gel RediSep (Isco Inc.) column with a 30 mL/min gradient elution of 10:90 (EtOAc:hexane) to 30:70 over 30 min, maintained at 30:70 for 15 min then to 50:50 over 6 min. Fractions containing product are combined and evaporated to give an oil which on standing in a high vacuum foamed to yield N-(t-butoxycarbonyl-sulfamoyl)-N-[2-(methoxycarbonylmethyl)-phenyl]-glycine t-butyl ester as a white foam: [M−1]$^-$=457.

E. N-Sulfamoyl-N-[2-(methoxycarbonylmethyl)-phenyl]glycine

The title D compound, N-(t-butoxycarbonyl-sulfamoyl)-N-[2-(methoxycarbonyl-methyl)-phenyl]-glycine t-butyl ester (1.87 g, 4.07 mmol) is dissolved in a mixture of TFA (35 mL) and CH$_2$Cl$_2$ (35 mL) and stirred for 30 min. The reaction is concentrated in vacuo, then triturated with diethyl ether to yield N-sulfamoyl-N-[2-(methoxycarbonylmethyl)-phenyl]glycine as a clear glass.

F. [2-(1,1,4-Trioxo-1,2,5-thiadiazolidin-2-yl)-phenyl]-acetic acid methyl ester Carbonyl diimidazole (60 mg, 0.37 mmol) is added as solid to a solution of the title E compound, N-sulfamoyl-N-[2-(methoxycarbonylmethyl)-phenyl] glycine (112 mg, 0.37 mmol) in THF (5 mL). After 65 h, the solvent is removed by evaporation. The residue is taken up in EtOAc and washed with 1N aqueous HCl followed by brine. The organic solution is dried over anhydrous MgSO$_4$, filtered and concentrated. This residue is then evaporated from diethyl ether to yield [2-(1,1,4-trioxo-1,2,5-thiadiazolidin-2-yl)-phenyl]-acetic acid methyl ester as a white foam: [M−1]$^-$=283.

EXAMPLE 41

[2-(1,1,4-Trioxo-1,2,5-thiadiazolidin-2-yl)-phenyl]-acetic acid

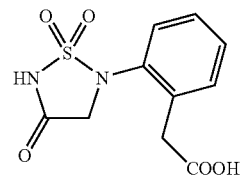

A solution of 2N aqueous NaOH (2.0 mL, 4.0 mmol) is added to a solution of the title compound of Example 40, [2-(1,1,4-trioxo-1,2,5-thiadiazolidin-2-yl)-phenyl]-acetic acid methyl ester (57 mg, 0.20 mmol) in MeOH (2.0 mL). The reaction is stirred for 3 h, then neutralized by addition of 2N aqueous HCl (2.0 mL). The mixture is concentrated on a Savant Speedvac to give a yellow solid. The solid is triturated with EtOAc, filtered and the filtrate is evaporated to give a yellow solid. This is dissolved in 2 mL water loaded onto a preparative reverse phase HPLC column (YMC CombiPrep Pro C18, 50×20 mm I.D., particle size S-5 micron, 12 nM) and eluted at 30 mL/min with a gradient of 90:10 (0.1% TFA in water:MeCN) to 10:90 over 5 min. Then held at 10:90 until 7 min. Fractions containing product are combined and concentrated on a Savant Speedvac to yield [2-(1,1,4-trioxo-1,2,5-thiadiazolidin-2-yl)-phenyl]-acetic acid as a white solid: [M−1]$^-$=269.

EXAMPLE 42

5-(2,4-Dimethoxyphenyl)-1,1-dioxo-[1,2,5]thiadiazolidin-3-one potassium salt

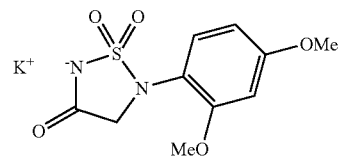

A. (2,4-Dimethoxyphenylamino)-acetic acid methyl ester

To a mixture of 1.53 g (10 mmol) of 2,4-dimethoxyaniline and 2.76 g (20 mmol) of potassium carbonate in 10 mL of DMF are added 1.53 g (10 mmol) of methyl bromoacetate. The mixture is stirred at 60° C. for 3 h, then allowed to cool to RT. The mixture is poured into water and extracted with EtOAc. The organic phase is washed with water, brine and dried over anhydrous Na$_2$SO$_4$. The solvent is removed under reduced pressure and the residue is chromatographed using CH$_2$Cl$_2$ as the eluant to give (2,4-dimethoxyphenylamino)-acetic acid methyl ester as an oil: $^1$H-NMR (CDCl$_3$) δ 6.46 (d, J=2.20, 1H), 6.41-6.38 (m, 2H), 3.91 (s, 2H), 3.84 (s, 3H), 3.77 (s, 3H), 3.75 (s, 3H).

B. N-(t-Butoxycarbonylsulfamoyl)-N-(2,4-dimethoxyphenyl)glycine methyl ester To a solution of 1.15 g (8.08 mmol) of chlorosulfonyl isocyanate in 10 mL of CH$_2$Cl$_2$ is added dropwise a solution of 598 mg (8.08 mmol) of t-butanol in 2 mL of CH$_2$Cl$_2$. The solution is stirred at RT for 45 min, then a solution of 1.3 g (5.8 mmol) of the title A compound, (2,4-dimethoxyphenylamino)-acetic acid methyl ester and 1.2 g (11.9 mmol) of TEA in 4 mL of CH$_2$Cl$_2$ is added dropwise. The mixture is stirred at RT for 90 min, then washed with water. The organic phase is dried over anhydrous Na$_2$SO$_4$ and the solvent is removed under reduced pressure. The residual oil is purified by chromatography using 10% EtOAc in CH$_2$Cl$_2$ as the eluant to give N-(t-butoxycarbonylsulfamoyl)-N-(2,4-dimethoxy-phenyl)glycine methyl ester as a thick yellow oil: $^1$H-NMR (CDCl$_3$) δ 7.57 (d, J=9.19, 1H), 7.19 (s, 1H), 6.51-6.46 (m, 2H), 4.55 (br s, 2H), 3.82 (s, 3H), 3.80 (s, 3H), 3.71 (s, 3H), 1.53 (s, 9H); [M–1]$^-$=403.

C. N-Sulfamoyl-N-(2,4-dimethoxyphenyl)glycine methyl ester

A solution of 1.7 g (4.2 mmol) of the title B compound, N-(t-butoxycarbonyl-sulfamoyl)-N-(2,4-dimethoxyphenyl) glycine methyl ester in 9 mL of TFA/CH$_2$Cl$_2$ (1:1) is stirred at RT for 30 min. The solvent is removed under reduced pressure. CH$_2$Cl$_2$ is added to the residue and the solvent is removed under reduced pressure. The resulting oil is purified by chromatography using 10% EtOAc in CH$_2$Cl$_2$ as the eluant to afford N-sulfamoyl-N-(2,4-dimethoxyphenyl)glycine methyl ester as an oil which crystallizes on standing: mp=100-103° C.; $^1$H-NMR (CDCl$_3$) δ 7.50 (d, J=8.09, 1H), 6.51-6.44 (m, 2H), 4.98 (br s, 2H), 3.84 (s, 3H), 3.81 (s, 3H), 3.75 (s, 3H).

D. 5-(2,4-Dimethoxyphenyl)-1,1-dioxo-[1,2,5]thiadiazolidin-3-one potassium salt To a solution of 980 mg (3.22 mmol) of the title C compound, N-sulfamoyl-N-(2,4-dimethoxyphenyl)glycine methyl ester in 15 mL of THF are added dropwise 3.0 mL of a 1.0M solution of potassium t-butoxide in THF. The mixture is stirred at RT for 4 h. The resulting precipitate is filtered and washed with THF. The soild is dried in vacuo to give 5-(2,4-dimethoxyphenyl)-1,1-dioxo-[1,2,5]thiadiazolidin-3-one potassium salt as a white solid: mp>260° C.; $^1$H-NMR (DMSO-d$_6$) δ 7.34 (d, J=8.66, 1H), 6.57 (d, J=2.64, 1H), 6.47 (dd, J=8.66, 3.01, 1H), 3.91 (s, 2H), 3.75 (s, 3H), 3.74 (s, 3H); [M–1]$^-$=271; Anal. Calcd for C$_{10}$H$_{11}$N$_2$O$_5$SK+0.3H$_2$O C, 38.04; H, 3.70; N, 8.87; Found C, 37.93; H, 3.42; N. 8.49.

EXAMPLE 43

N-Benzyl-2-[3-methyl-4(1,1,4-trioxo-[1,2,5]thiadiazolidin-2-yl)-phenoxy]-acetamide

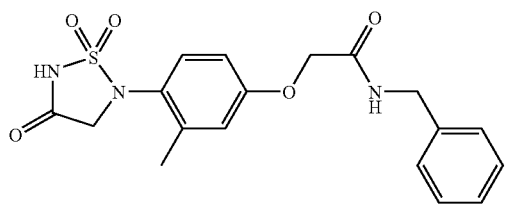

A. (3-Methyl-4-nitrophenoxy)-acetic acid t-butyl ester

A mixture of 1.53 g (10 mmol) of 3-methyl-4-nitrophenol, 1.95 g (10 mmol) of t-butyl bromoacetate and 2.76 g (20 mmol) of potassium carbonate in 10 mL of DMF are stirred at RT for 2 h. Water is added and the mixture is extracted with EtOAc and the organic phase is washed with water and brine, and dried over anhydrous Na$_2$SO$_4$. The solvent is removed under reduced pressure and the residual oil is filtered through a pad of silica gel using CH$_2$Cl$_2$ as the eluant to give (3-methyl-4-nitrophenoxy)-acetic acid t-butyl ester as an oil: $^1$H-NMR (CDCl$_3$) δ 8.08 (d, J=9.56, 1H), 6.82-6.75 (m, 2H), 4.58 (s, 2H), 2.63 (s, 3H), 1.49 (s, 9H); Anal. Calcd for C$_{13}$H$_{17}$NO$_5$ C, 58.42; H, 6.41; N, 5.24; Found C, 58.04; H, 6.51; N, 5.09.

B. (4-Amino-3-methylphenoxy)-acetic acid t-butyl ester

A solution of 2.35 g (8.8 mmol) of the title A compound, (3-methyl-4-nitrophenoxy)-acetic acid t-butyl ester in 40 mL of EtOH is hydrogenated at 45 psi for 18 h in the presence of 10% Pd/C. The catalyst is removed by filtration through Celite and the filtrate is concentrated to give (4-amino-3-methylphenoxy)-acetic acid t-butyl ester as an oil: $^1$H-NMR (CDCl$_3$) δ 6.68 (br s, 1H), 6.61 (s, 2H), 4.43 (s, 2H), 2.15 (s, 3H), 1.48 (s, 9H); [M+1]$^+$=238.

C. (4-t-Butoxycarbonylmethoxy-2-methylphenylamino)-acetic acid methyl ester

To a mixture of 2.1 g (8.9 mmol) of the title B compound, (4-amino-3-methylphenoxy)-acetic acid t-butyl ester and 2.44 g (17.7 mmol) of potassium carbonate in 8 mL of DMF are added 1.76 g (11.5 mmol) of methyl bromoacetate. The mixture is stirred at 60° C. for 1 h, then allowed to cool to RT. The mixture is poured into water and extracted with EtOAc. The organic phase is washed with water and brine, and dried over anhydrous Na$_2$SO$_4$. The solvent is removed under reduced pressure and the residue is chromatographed using CH$_2$Cl$_2$ as the eluant to afford (4-t-butoxycarbonylmethoxy-2-methylphenylamino)-acetic acid methyl ester as an oil (contaminated with approx 25% of dialkylated product): $^1$H-NMR (CDCl$_3$) δ 6.76-6.64 (m, 2H), 6.40 (d, J=8.46, 1H), 4.43 (s, 2H), 3.91 (s, 2H), 3.78 (s, 3H), 2.19 (s, 3H), 1.48 (s, 9H).-

D. N-(t-Butoxycarbonylsulfamoyl)-N-(4-t-butoxy-carbonylmethoxy-2-methylphenylamino)glycine methyl ester To a solution of 1.17 g (8.2 mmol) of chlorosulfonyl isocyanate in 10 mL of CH$_2$Cl$_2$ is added dropwise a solution of 610 mg (8.2 mmol) of t-butanol in 5 mL of CH$_2$Cl$_2$. The solution is stirred at RT for 45 min, then a solution of 1.96 g (6.3 mmol) of the title C compound, (4-t-butoxycarbonylmethoxy-2-methylphenylamino)-acetic acid methyl ester and 1.1 g (10.9 mmol) of TEA in 8 mL of CH$_2$Cl$_2$ is added dropwise. The mixture is stirred at RT for 5 h, then washed with water. The organic phase is dried over anhydrous Na$_2$SO$_4$, and the solvent is removed under reduced pressure. The residual oil is purified by chromatography using 10% EtOAc in CH$_2$Cl$_2$ as the eluant to give N-(t-butoxycarbonylsulfamoyl)-N-(4-t-butoxycarbonyl-methoxy-2-methylphenylamino)glycine methyl ester as an oil: $^1$H-NMR (CDCl$_3$) δ 7.42 (d, J=8.67, 1H), 6.79-6.68 (m, 2H), 4.52 (q, 2H), 4.49 (s, 2H), 3.73 (s, 3H), 2.39 (s, 3H), 1.49 (s, 9H); [M−1]$^-$=487.

E. N-Sulfamoyl-N-(4-(methoxycarbonylmethylamino)-3-methylphenoxy-acetic acid A solution of 630 mg (1.29 mmol) of the title D compound, N-(t-butoxycarbonyl-sulfamoyl)-N-(4-t-butoxycarbonylmethoxy-2-methylphenylamino)glycine methyl ester in 6 mL of TFA/CH$_2$Cl$_2$ (1:1) is stirred at RT for 30 min. The solvent is removed under reduced pressure. CH$_2$Cl$_2$ is added to the residue and the solvent is removed under reduced pressure to give N-sulfamoyl-N-(4-(methoxycarbonyl-methylamino)-3-methylphenoxy-acetic acid as a sticky white solid: $^1$H-NMR (DMSO-d$_6$) δ 7.32 (d, J=8.83, 1H), 7.01 (br s, 2H), 6.80-6.68 (m, 2H), 4.66 (s, 2H), 4.24 (broad d, J=22.80, 2H), 3.59 (s, 3H), 2.34 (s, 3H).

F. {1-[4-(Benzylcarbamoylmethoxy)-2-methylphenyl]-sulfamoyl}-acetic acid methyl ester To a solution of 406 mg (1.22 mmol) of the title E compound, N-sulfamoyl-N-(4-(methoxycarbonylmethylamino)-3-methylphenoxy-acetic acid, 234 mg (1.22 mmol) of EDCI and 167 mg (1.22 mmol) of HOAt in 4 mL of DMF are added 131 mg (1.22 mmol) of benzylamine. The mixture is stirred at RT for 18 h, then EtOAc is added. The organic mixture is washed with aqueous 10% NaHCO$_3$, 1 N aqueous HCl, water and brine. The organic solution is dried over anhydrous Na$_2$SO$_4$, and the solvent is removed under reduced pressure. The residual oil is chromatographed using 15% EtOAc in CH$_2$Cl$_2$ then 50% EtOAc in CH$_2$Cl$_2$ as the eluant to give (1-[4-(benzylcarbamoylmethoxy)-2-methylphenyl]-sulfamoyl}-acetic acid methyl ester as a foam: $^1$H-NMR (CDCl$_3$) δ 7.53 (d, J=8.46, 1H), 7.39-7.25 (m, 5H), 6.82 (d, J=2.94, 1H), 6.72 (dd, J=11.39, 2.94, 1H), 5.15 (s, 2H), 4.55 (d, J=5.88, 2H), 4.51 (s, 2H), 3.78 (s, 3H), 2.37 (s, 3H); [M−1]=420.

G. N-Benzyl-2-[3-methyl-4-(1,1,4-trioxo-[1,2,5]thiadiazolidin-2-yl)-phenoxy]-acetamide To a solution of 180 mg (0.427 mmol) of the title F compound {1-[4-(benzyl-carbamoylmethoxy)-2-methylphenyl]-sulfamoyl}-acetic acid methyl ester in 2 mL of THF is added dropwise 1.0M solution of potassium t-butoxide in THF (0.42 mL). The mixture is stirred at RT for 5 h and the solvent is removed under reduced pressure. To the resulting gum are added 3 mL of water and the resulting solution is washed with MTBE. The aqueous layer is acidified with 2N aqueous HCl and the mixture is extracted with EtOAc. The organic solution is dried over anhydrous Na$_2$SO$_4$, and the solvent is removed under reduced pressure to give N-benzyl-2-[3-methyl-4-(1,1,4-trioxo-[1,2,5]thiadiazolidin-2-yl)-phenoxy]-acetamide as a beige foam: mp=70-90° C.; $^1$H-NMR (CDCl$_3$) δ 7.43-7.25 (m, 7H), 6.94 (t, 1H), 6.87-6.78 (m, 2H), 4.59 (s, 2H), 4.56 (d, J=5.88, 2H), 4.30 (s, 2H), 2.39 (s, 3H); [M−1]$^-$=388; Anal. Calcd for C$_{18}$H$_{19}$N$_3$O$_5$S C, 55.52; H, 4.92; N, 10.79; Found: C, 55.45; H, 4.92; N, 10.50.

EXAMPLE 44

3-[3-Hydroxy-4-(1,1,4-trioxo-[1,2,5]thiadiazolidin-2-yl)-benzyl]-3,4-dihydro-1H-benzo[1,4]diazepine-2,5-dione

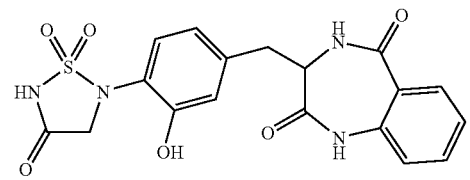

A. 3-Benzyloxy-4-nitrobenzaldehyde

3-Hydroxy-4-nitro-benzaldehyde (4.68 g, 28 mmol) is dissolved in DMF (27 mL) and to the solution is added with stirring powdered potassium carbonate (4.27 g, 30.1 mmol) and benzyl bromide (3.34 mL, 28.1 mmol). The mixture is stirred at RT overnight, diluted with water (200 mL) and extracted three times with EtOAc. The organic extracts are washed with 10% potassium carbonate and brine, dried over anhydrous MgSO$_4$, decolorized with charcoal, filtered and evaporated to give 3-benzyloxy-4-nitro-benzaldehyde as an oil which is used in the next step without purification.

B. 3-Benzyloxy-4-nitro-benzyl alcohol

To a cold (ice-water) solution of the title A compound, 3-benzyloxy-4-nitro-benzaldehyde (6.13 g, 23.8 mmol) in methanol (60 mL) is added in portions with stirring sodium borohydride (906 mg, 24 mmol) and the mixture is allowed to warm up to RT overnight. The mixture is evaporated to dryness at aspirator pressure and the residue is triturated with 2N aqueous HCl and extracted 3 times with EtOAc. The organic extracts are washed with brine, dried over anhydrous MgSO$_4$, filtered and evaporated to give 3-benzyloxy-4-nitro-benzyl alcohol which solidifies on standing at RT under vacuum.

C. 3-Benzyloxy-4-nitro-benzyl alcohol p-tolune sulfonic acid ester

A solution of the title B compound, 3-benzyloxy-4-nitrobenzyl alcohol (0.519 g, 2 mmol) in THF (8 mL) is cooled to 0° C. with stirring under nitrogen and lithium bis(trimethylsilyl)-amide (1 M in hexane, 2 mL, 2 mmol) is added dropwise over a period of 5 min. The mixture is stirred at 0°

C. for 15 min and p-toluene sulfonyl chloride (382 mg, 2 mmol) is added all at once. The mixture is stirred at 0° C. for 15 min and quenched with saturated aqueous NH$_4$Cl (5 mL). The mixture is extracted twice with EtOAc and the extracts are washed with water and brine, then dried over anhydrous MgSO$_4$, filtered and evaporated to give 3-benzoyloxy-4-nitro-benzyl alcohol p-toluene sulfonic acid ester as a viscous oil: $^1$H-NMR δ 7.78 (m, 3H), 7.5-7.3 (m, 7H), 7.05 (s, 1H), 6.88 (d, 2H), 5.2 (s, 2H), 5.08, (s, 2H) 2.42 (s, 3H).

D. 3-Benzyloxy-4-nitro-benzyl iodide

To a solution of the title C compound, 3-benzyloxy-4-nitro-benzyl alcohol p-toluene sulfonic acid ester (8.57 g, 20.7 mmol) in acetone (126 mL) is added with stirring a solution sodium iodide (7.77 g, 51.8 mmol) in acetone (63 mL) all at once. The mixture is stirred at RT overnight and evaporated. The residue is triturated with water, extracted twice with EtOAc and the extracts are washed with water and brine, then dried over anhydrous MgSO$_4$ and evaporated. The residue is purified by chromatography on silica gel column (2×10 cm, on EtOAc-hexane, 1:1) to give of 3-benzyloxy-4-nitro-benzyl iodide which solidifies on standing at RT: $^1$H-NMR δ 7.81 (d, 1H), 7.1 (s, 1H), 7.0 (d, 1H), 7.5-7.3 (m, 5H), 5.23 (s, 2H), 4.39 (s, 2H).

E. 2-(3-Benzyloxy-4-nitro-benzyl)-2-t-butoxycarbonylamino-malonic acid dimethyl ester Sodium hydride (60% in mineral oil, 729 mg, 18.22 mmol) is washed twice with dry hexane and suspended in DMF (15 mL). To the suspension is added dropwise a solution of t-butoxycarbonylamino-malonic acid dimethyl ester (4.92 g, 19.9 mmol) in DMF (15 mL) over a period of 10 min. The mixture is stirred at RT for 40 min and a solution of the title D compound, 3-benzyloxy-4-nitrobenzyl iodide (6.23 g, 16.9 mmol) in DMF (15 mL) is added dropwise over a period of 10 min and the mixture is stirred at RT overnight. The mixture is diluted with water (200 mL) and extracted 3 times with EtOAc. The organic extracts are washed with water and brine, dried over anhydrous MgSO$_4$, filtered and evaporated. The residue is crystallized from ether-hexane to give 2-(3-benzyloxy-4-nitro-benzyl)-2-t-butoxycarbonylamino-malonic acid dimethyl ester: mp=114-116° C.

F. 3-(3-Benzyloxy-4-nitro-phenyl)-2-t-butyloxycarbonylamino-propionic acid methyl ester To a solution of the title E compound, 2-(3-benzyloxy-4-nitro-benzyl)-2-t-butoxycarbonylamino-malonic acid dimethyl ester (6.98 g, 14.3 mmol) in DMSO (68 mL) and water (1.46 mL) sodium chloride (0.85 g, 14.6 mmol) is added and the mixture is gradually heated to 150° C. for 1 h. The mixture is cooled to RT, diluted with water (300 mL) and extracted 3 times with EtOAc. The organic extracts are washed with water and brine, dried over anhydrous MgSO$_4$, decolorized with charcoal, filtered and evaporated. The residue is purified by chromatography (silica gel column, 6×30 cm, on EtOAc-hexane 1:1) to give 3-(3-Benzyloxy-4-nitro-phenyl)-2-tert-butyloxycarbonylamino-propionic acid methyl ester as a crystalline solid: mp=104-105° C.

G. 3-(3-Benzyloxy-4-nitro-phenyl)-2-amino-propionic acid methyl ester

A solution of the title F compound, 3-(3-benzyloxy-4-nitro-phenyl)-2-t-butyloxycarbonylamino-propionic acid methyl ester (733 mg, 1.7 mmol) in a mixture of CH$_2$Cl$_2$-trifluoroacetic acid (1:1, 7 mL) is stirred at RT for 30 min, then evaporated. The residue is partitioned between EtOAc and saturated aqueous NaHCO$_3$. The layers are separated and the aqueous layer is extracted once more with EtOAc. The combined organic extracts are washed with brine, dried over anhydrous MgSO$_4$, filtered and evaporated to give 3-(3-benzyloxy-4-nitro-phenyl)-2-amino-propionic acid methyl ester as a viscous yellow oil.

H. 2-(2-Amino-benzoylamino)-3-(3-benzyloxy-4-nitro-phenyl)propionic acid methyl ester A mixture of the title G compound, 3-(3-benzyloxy-4-nitro-phenyl)-2-amino-propionic acid methyl ester (597 mg, 1.7 mmol), isatoic anhydride (278 mg, 1.7 mmol) and pyridine (5 mL) is heated with stirring at 80° C. for 7 h and allowed to cool to RT overnight. The mixture is evaporated to dryness, the residue is dissolved in EtOAc and the solution is washed with water and brine, dried over anhydrous MgSO$_4$, filtered and evaporated. The residue is purified by chromatography (silica gel column, 3×20 cm, on EtOAc-hexane-methanol, 8:12:2) to give 2-(2-amino-benzoylamino)-3-(3-benzyloxy-4-nitro-phenyl)-propionic acid methyl ester: $^1$H-NMR δ 7.815 (d, 1H), 6.294 (s, 1H), 6.825 (d, 1H), 7.384-7.206 (m, 7H), 6.699-6.577 (m, 3H), 5.532 (br s, 2H), 5.093-5.039 (m, 3H), 3.749 s, 3H), 3.403-3.175 (m, 2H).

I. 2-(2-Amino-benzoylamino)-3-(3-benzyloxy-4-nitro-phenyl)-propionic acid

To a solution of the title H compound, 2-(2-amino-benzoylamino)-3-(3-benzyloxy-4-nitro-phenyl)-propionic acid methyl ester (388 mg, 0.863 mmol) in methanol (8 mL) is added 1N aqueous NaOH (1.73 mL, 1.73 mmol) and the mixture is stirred at RT for 2 h and evaporated. The residue is dissolved in water (20 mL) and the solution is washed twice with EtOAc. The aqueous layer is neutralized with 1N aqueous HCl (1.73 mL) and extracted three times with EtOAc. The organic extracts are washed with brine, dried over anhydrous MgSO$_4$, decolorized with charcoal, filtered and evaporated to give 2-(2-amino-benzoylamino)-3-(3-benzyloxy-4-nitro-phenyl)-propionic acid as a viscous yellow oil: [M+1]$^+$=436, [M−1]$^−$=434.

J. 3-(3-Benzyloxy-4-nitro-benzyl)-3,4-dihydro-1H-benzo[1,4]diazepine-2,5-dione To a solution of the title I compound, 2-(2-amino-benzoylamino)-3-(3-benzyloxy-4-nitro-phenyl)-propionic acid (317 mg, 0.728 mmol) in CH$_2$Cl$_2$ (10 mL) is added HOBt (111.5 mg, 0.728 mmol) and 1-ethyl-(3-dimethylaminopropyl)carbodiimide hydrochloride (EDAC.HCl, 140 mg, 0,72 mmol) and the mixture is stirred at RT for 4 h and evaporated. The residue is partitioned between EtOAc and water and the organic solution is washed with 1N aqueous HCl, water, saturated aqueous NaHCO$_3$ and brine, dried over anhydrous MgSO$_4$, decolorized and evaporated to a small volume. The precipitated product is collected by filtration and dried to give 3-(3-benzyloxy-4-nitro-benzyl)-3,4-dihydro-1H-benzo[1,4]diazepine-2,5-dione: mp=243-245° C.

K. 3-(4-Amino-3-benzyloxy-benzyl)-3,4-dihydro-1H-benzo[-1,4]diazepine-2,5-dione A solution of the title J compound, 3-(3-benzyloxy-4-nitro-benzyl)-3,4-dihydro-1H-benzo[1,4]diazepine-2,5-dione (196 mg, 0.47 mmol) in EtOAc-methanol (1:1, 44 mL) is hydrogenated over platinum oxide (22 mg) at atmospheric pressure for 1 h. The catalyst is filtered off and the filtrate is evaporated to dryness to give 3-(4-amino-3-benzyloxy-benzyl)-3,4-dihydro-1H-benzo[1,4]diazepine-2,5-dione as a foam: $[M+1]^+=388$.

L. 2-Benzyloxy-4-(2,5-dioxo-2,3,4,5-tetrahydro-1H-benzo[1,4]diazepin-3-ylmethyl)-phenylamino]-acetic acid ethyl ester To a solution of the title K compound, 3-(4-amino-3-benzyloxy-benzyl)-3,4-dihydro-1H-benzo[1,4]diazepine-2,5-dione (190 mg, 0.47 mmol) in THF (1 mL) is added ethyl glyoxalate (50% in toluene, 0.120 mL, 0.61 mmol) and the mixture is stirred at RT for 30 min. The mixture is diluted with methanol-acetic acid (9:1, 4 mL) and solid sodium cyanoborohydride (32 mg, 0.52 mmol) is added at once and the mixture is stirred at RT overnight. The mixture is evaporated to dryness the residue is extracted with EtOAc, washed with saturated aqueous NaHCO$_3$, and brine, dried and evaporated. The residue is purified by chromatography (silica gel column, 2×20 cm, on EtOAc-hexane-methanol 6:4:1) to give 2-benzyloxy-4-(2,5-dioxo-2,3,4,5-tetrahydro-1H-benzo[1,4]diazepin-3-ylmethyl)-phenylamino]-acetic acid ethyl ester as a white crystalline solid: mp=156-158° C.

M. N-[2-Benzyloxy-4-(2,5-dioxo-2,3,4,5-tetrahydro-1H-benzo[1,4]diazepin-3-ylmethyl)-phenyl]-N-[t-butyloxycarbonylaminosulfonyl]-amino-acetic acid ethyl ester A solution of t-butyloxycarbonylaminosulfonyl chloride in CH$_2$Cl$_2$ (1 M solution) is prepared by dissolving t-butyl alcohol (0.35 mL, 3.66 mmol) in CH$_2$Cl$_2$ (2.6 mL), cooling the solution to 0° C., adding dropwise with stirring chlorosulfonyl isocyanate (0.32 mL, 3.68 mmol) and stirring the mixture at 0° C. for 1 h. The above reagent (0.314 mL, 0.314 mmol) is added dropwise to a solution of the title L compound, 2-benzyloxy-4-(2,5-dioxo-2,3,4,5-tetrahydro-1H-benzo[1,4]diazepin-3-ylmethyl)-phenylamino]-acetic acid ethyl ester (92 mg, 0.194 mmol in CH$_2$Cl$_2$ (2 mL) at 0° C. with stirring. The resulting solution is allowed to reach RT and stirred overnight. The mixture is diluted with CH$_2$Cl$_2$, washed with water, 1N aqueous HCl, saturated aqueous NaHCO$_3$, and brine, dried over anhydrous MgSO$_4$, filtered and evaporated to give N-[2-benzyloxy-4-(2,5-dioxo-2,3,4,5-tetrahydro-1H-benzo[1,4]diazepin-3-ylmethyl)-phenyl]-N-[t-butyloxycarbonylamino-sulfonyl]-amino-acetic acid ethyl ester: $[M+1]^+=653$.

N. N-[2-Benzyloxy-4-(2,5-dioxo-2,3,4,5-tetrahydro-1H-benzo[1,4]diazepin-3-ylmethyl)-phenyl]-N-[aminosulfonyl]-amino-acetic acid ethyl ester The title M compound, N-[2-benzyloxy-4-(2,5-dioxo-2,3,4,5-tetrahydro-1H-benzo[1,4]diazepin-3-ylmethyl)-phenyl]-N-[t-butyloxycarbonylaminosulfonyl]-amino-acetic acid ethyl ester (124 mg, 0.19 mmol) is dissolved in CH$_2$Cl$_2$-TFA-triethylsilane (2.5:7:0.5, 1.5 mL) and the solution is stirred at RT for 1 h and evaporated. The residue is dissolved in EtOAc and the solution is washed twice with saturated aqueous NaHCO$_3$ and brine, dried over anhydrous MgSO$_4$, filtered and evaporated to give N-[2-benzyloxy-4-(2,5-dioxo-2,3,4,5-tetrahydro-1H-benzo[1,4]diazepin-3-ylmethyl)-phenyl]-N-[aminosulfonyl]-amino-acetic acid ethyl ester as a foam: $[M+1]^+=553$.

O. 3-[3-Benzyloxy-4-(1,1,4-trioxo-[1,2,5]thiadiazolidin-2-yl)-benzyl]-3,4-dihydro-1H-benzo[1,4]diazepine-2,5-dione To a solution of the title N compound, N-[2-benzyloxy-4-(2,5-dioxo-2,3,4,5-tetrahydro-1H-benzo[1,4]diazepin-3-ylmethyl)-phenyl]-N-[aminosulfonyl]-amino-acetic acid ethyl ester (93 mg, 0.168 mmol) in THF is cooled to 0° C. and treated dropwise with a solution of potassium t-butoxide in THF (1M, 0.244 mL, 0.244 mmol). After stirring at 0° C. for 30 min, additional potassium t-butoxide solution is added and stirring continued for another 1 h. The resulting suspension of fine solids is centrifuged, the supernatant is decanted and the cake of solids is suspended in EtOAc and centrifuged. The supernatant is decanted and the cake of solids is triturated with EtOAc and 2N aqueous HCl. The EtOAc layer is washed with brine, dried over anhydrous MgSO$_4$, decolorized with charcoal, filtered and evaporated to give 3-[3-benzyloxy-4-(1,1,4-trioxo-[1,2,5]thiadiazolidin-2-yl)-benzyl]-3,4-dihydro-1H-benzo[1,4]diazepine-2,5-dione as a foam: $[M+1]^+=507$.

P. 3-[3-Hydroxy-4-(1,1,4-trioxo-[1,2,5]thiadiazolidin-2-yl)-benzyl]-3,4-dihydro-1H-benzo[1,4]diazepine-2,5-dione A solution of 3-[3-benzyloxy-4-(1,1,4-trioxo-[1,2,5]thiadiazolidin-2-yl)-benzyl]-3,4-dihydro-1H-benzo[1,4]diazepine-2,5-dione (452 mg, 0.89 mmol) in ethanol-acetic acid (2:1, 12 mL) is hydrogenated over 10% palladium on charcoal catalyst (106 mg) at 50 psi for 24 h. The catalyst is filtered and the filtrate is evaporated to dryness. The residue is purified by LC-MS, on a Gilson-Micromass instrument using a Phenominex Luna, 5μ, 60×21.2 mm, C-8 column, a gradient of 5% to 100% over 8 min with solvent A (water, 0.1% trifluoroacetic acid) and B (MeCN, 0.1% trifluoroacetic acid) with flow rate 20 mL/min, UV detector at 215 nm and cone voltage setting at 30 V. The purification is conducted with several runs with 50 mg of crude material being used in each run (approximately 16 runs). Pure fractions are pooled and evaporated to dryness, the residue is dissolved in water-MeCN and the solution is filtered and the filtrate is concentrated to give 3-[3-hydroxy-4-(1,1,4-trioxo-[1,2,5]thiadiazolidin-2-yl)-benzyl]-3,4-dihydro-1H-benzo[1,4]diazepine-2,5-dione as an amorphous solid: mp=180° C.; $[M+1]^+=417$.

EXAMPLE 45

5-(4-Iodo-phenyl)-1,1-dioxo-1,2,5-thiadiazolidin-3-one

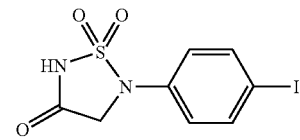

A. N-(2-Trimethylsilylethoxycarbonyl-sulfamoyl)-N-(4-iodo-phenyl)glycine methyl ester Chlorosulfonylisocyanate (3.97 mL, 45.6 mmol) is added to $CH_2Cl_2$ (50 mL) in a dry 300 mL Schlenk flask under-argon balloon, and cooled with stirring in an ice/salt/water bath. Trimethylsilylethanol (6.53 mL, 45.6 mmol) is added to this solution and stirred while maintaining the cooling for 1 h. Then a solution (4-Iodophenylamino)acetic acid methyl ester (4.43 g, 15.2 mmol, obtained by alkylation of 4-iodoaniline using the method of Tohru Fukuyama et. al., *Tet. Lett.* 1997, 38 (33), 5831-34) and TEA (8.69 mL, 62.32 mmol) in $CH_2Cl_2$ (50 mL) is rapidly cannulated into this above mentioned stirred, cooled solution. After 30 min, the reaction is poured into 400 mL of 1N aqueous HCl and extracted with EtOAc. The organic layer is washed with 1N aqueous HCl, dried over anhydrous $Na_2SO_4$, filtered and concentrated. The residue is chromatographed on a 110 g silica gel RediSep (Isco Inc.) column with a 30 mL/min gradient elution of 5:95 (EtOAc:$CH_2Cl_2$) to 10:90 over 15 min. Fractions containing product are combined and evaporated to give an oil which on standing in a high vacuum solidified to yield N-(2-trimethylsilylethoxycarbonyl-sulfamoyl)-N-(4-iodo-phenyl)glycine methyl ester as a yellow solid.

B. 5-(4-Iodo-phenyl)-1,1-dioxo-1,2,5-thiadiazolidin-3-one

Tetrabutylammonium fluoride (6.39 g, 24.48 mmol) is added to a solution of the title A compound, N-(2-trimethylsilylethoxycarbonyl-sulfamoyl)-N-(4-iodo-phenyl)glycine methyl ester (3.15 g, 6.12 mmol) in freshly distilled tetrahydrofuran (60 mL). The reaction is stirred under argon and heated at 90° C. The reaction is monitored by reverse phase HPLC (YMC CombiScreen Pro C18, 50×4.6 mm I.D., particle size S-5 micron, 12 nM) eluting at 3 mL/min with a gradient of 90:10 (0.1% TFA in water: MeCN) to 10:90 at 7.0 min. Starting material has a retention time of 4.88 min and the product has a retention time of 2.83 min. After 24 h, the reaction is poured into 500 mL of 1N aqueous HCl and extracted with EtOAc. The organic solution is treated with $Na_2SO_4$ and charcoal, filtered through celite and concentrated to give an oil. Crystallization from EtOAc/hexane (and some additional charcoal) yields 5-(4-iodo-phenyl)-1,1-dioxo-1,2,5-thiadiazolidin-3-one as a light yellow powder: mp=191-193° C., $[M-H]^-=336.8$.

EXAMPLE 46

(S)-2-Amino-3-[4-(1,1,4-trioxo-1,2,5-thiadiazolidin-2-yl)-phenyl]-propionic acid benzyl ester

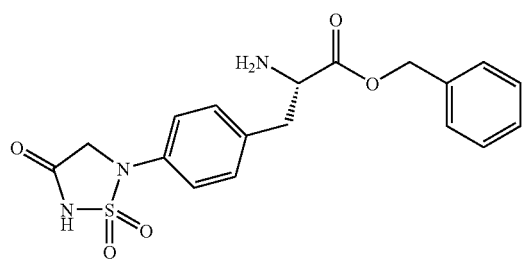

A. 5-(4-Iodo-phenyl)-2-(4-methoxy-benzyl)-1,1-dioxo-1,2,5-thiadiazolidin-3-one

The title compound of Example 45, 5-(4-iodo-phenyl)-1,1-dioxo-1,2,5-thiadiazolidin-3-one (355.9 mg, 1.05 mmol) is dissolved in THF (20 mL) in a 40 mL capacity septum capped vial, and stirred under argon balloon. Triphenylphosphine (552 mg, 2.11 mmol) is added as a solid and stirred until dissolved, then 4-methyoxybenzyl alcohol (0.156 mL, 1.26 mmol) is added by syringe. The stirred reaction is cooled in an ice bath, and disopropyl azodicarboxylate (0.415 mL, 2.11 mmol) is added slow dropwise by syringe. After two h, the reaction is concentrated in vacuo and the residue is taken up in $CH_2Cl_2$. Chromatography on a 35 g silica gel RediSep column (Isco, Inc.) with a 30 mL/min gradient elution of 10:90 (EtOAc:hexane) to 30:70 over 15 min gives 5-(4-iodo-phenyl)-2-(4-methoxy-benzyl)-1,1-dioxo-1,2,5-thiadiazolidin-3-one as a white solid. $^1$H-NMR (300 MHz, CDCl3) 3.80 (s, 3H), 4.37 (s, 2H), 4.79 (s, 2H), 6.89 (d, J=7.5, 2H, aryl), 7.03 (d, J=7.5, 2H), 7.41 (d, J=7.5, 2H), 7.73 (d, J=7.5, 2H).

B. (S)-2-t-Butoxycarbonylamino-3-{4-[5-(4-methoxy-benzyl)-1,1,4-trioxo-1,2,5-thiadiazolidin-2-yl]-phenyl}-propionic acid benzyl ester Onto zinc foil (99.9% Aldrich 35, 602-6, 775 mg, 11.85 mmol) cut in small pieces is added DMF (freshly distilled from $CaH_2$ under argon, 4.5 mL) and 1,2-dibromoethane (0.033 mL, 0.38 mmol) under argon. The mixture is heated at 50° C. for 10 min, then allowed to cool and trimethylsilyl chloride (0.19 mL, 0.153 mmol) is added. The reaction is stirred for 25 min and a solution of (R)-2-t-butoxycarbonylamino-3-iodo-propionic acid benzyl ester (Fluka, 2.18 g, 5.37 mmol) in DMF (10 mL) is added. After 15 min, the mixture is decanted into a solution of the title A compound, 5-(4-iodo-phenyl)-2-(4-methoxy-benzyl)-1,1-dioxo-1,2,5-thiadiazolidin-3-one (1.75 g, 3.82 mmol), tri-o-tolylphosphine (232.5 mg, 0.764 mmol) and tris(dibenzylideneacetone)-dipalladium(0) (175 mg, 0.191 mmol) in DMF (13 mL). After stirring for 1.5 h, the resulting reaction mixture is poured onto a mixture of saturated aqueous ammonium chloride (200 mL) and water (200 mL) and extracted with EtOAc (2×250 mL). The organic solution is washed with water (1×200 mL) and brine (1×200 mL), then filtered through celite to removed a strong gray precipitate. The filtrate is dried over anhydrous $Na_2SO_4$, filtered and concentrated to give a dark red brown oil. This is chromatographed on a 110 g silica gel RediSep column (Isco, Inc.) with a 30 mL/min gradient elution of 0:100 (EtOAc:$CH_2Cl_2$) to 10:90 over 25 min. Fractions containing product are combined and concentrated to yield (S)-2-t-butoxycarbonylamino-3-(4-[5-(4-methoxy-benzyl)-1,1,4-trioxo-1,2,5-thiadiazolidin-2-yl]-phenyl}-propionic acid benzyl ester as a white solid after trituration with $Et_2O$: $[M+NH_4]^+=627.0$, $[M-HCO_2]^-=654.1$.

C. (S)-2-Amino-3-[4-(1,1,4-trioxo-1,2,5-thiadiazolidin-2-yl)-phenyl]-propionic acid benzyl ester The title B compound, (S)-2-t-butoxycarbonylamino-3-{4-[5-(4-methoxy-benzyl)-1,1,4-trioxo-1,2,5-thiadiazolidin-2-yl]-phenyl}-propionic acid benzyl ester (40 mg, 0.066 mmol) is dissolved in TFA (1.32 mL) containing t-butyidimethylsilane (0.033 mL, 0.198 mmol) in a 1 dram vial. The reaction is monitored by reverse phase HPLC (YMC CombiScreen Pro C18, 50×4.6 mm I.D., particle size S-5 micron, 12 nM) eluting at 3 mL/min with a gradient of 90:10 (0.1% TFA in water:MeCN) to 10:90 at 7.0 min. Starting material has a retention time of 4.97 min and a new peak has a retention time of 3.09 min, the starting material without the t-butoxylcarbonyl group as an "intermediate", [M+H]⁺=510. After 25 min at RT, the reaction is heated at 80° C. for an additional 25 min. A new peak by HPLC has a retention time of 2.02 min, corresponding to the desired product. The reaction is cooled, filtered through florisil to remove a black precipitate and concentrated on a Savant Speedvac. The resulting residue is triturated with Et₂O to give a white solid. This material is purified on a preparative reverse phase HPLC column (YMC CombiPrep Pro C18, 50×20 mm I.D., particle size S-5 micron, 12 nM) in two equal aliquots and eluted at 30 mL/min with a gradient of 90:10 (0.1% TFA in water:MeCN) 10:90 over 5.0 min, then held at 10:90 until 7 min. Fractions containing product are combined and concentrated on a Savant Speedvac to yield (S)-2-amino-3-[4-(1,1,4-trioxo-1,2,5-thiadiazolidin-2-yl)-phenyl]-propionic acid benzyl ester as a white foam: [M−1]⁻=388.0.

EXAMPLE 47

(S)-2-Amino-3-[4-(1,1,4-trioxo-1,2,5-thiadiazolidin-2-yl)-phenyl]-propionic acid

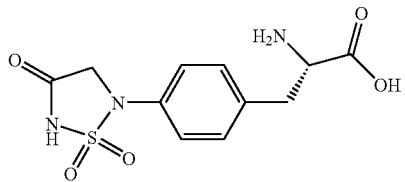

A. (S)-2-t-Butoxycarbonylamino-3-{4-[5-(4-methoxy-benzyl)-1,1,4-trioxo-1,2,5-thiadiazolidin-2-yl]-phenyl}-propionic acid The title B compound in Example 46, (S)-2-t-butoxycarbonylamino-3-{4-[5-(4-methoxy-benzyl)-1,1,4-trioxo-1,2,5-thiadiazolidin-2-yl]-phenyl}-propionic acid benzyl ester (107 mg, 0.176 mmol) is dissolved in a 1:1 mixture of EtOAc:EtOH (50 mL) in a 200 mL Parr bottle. 10% Palladium on carbon (30 mg) is added as a solid and the reaction mixture is hydrogenated on a Parr Shaker Apparatus at 41 psi of hydrogen for 2.5 h. The reaction mixture is filtered through celite and concentrated in vacuo to give (S)-2-t-butoxycarbonyl-amino-3-{4-[5-(4-methoxy-benzyl)-1,1,4-trioxo-1,2,5-thiadiazolidin-2-yl]-phenyl}-propionic acid as a white foam: [M−H]⁻=518.1.

B. (S)-2-Amino-3-[4-(1,1,4-trioxo-1,2,5-thiadiazolidin-2-yl)phenyl]-propionic acid The title A compound, (S)-2-t-butoxycarbonylamino-3-(4-[5-(4-methoxy-benzyl)-1,1,4-trioxo-1,2,5-thiadiazolidin-2-yl]-phenyl)-propionic acid (84.5 mg, 0.163 mmol) is dissolved in TFA (3.26 mL) containing t-butyidimethylsilane (0.081 mL, 0.498 mmol) at RT. The reaction is monitored by reverse phase HPLC (YMC CombiScreen Pro C18, 50×4.6 mm I.D., particle size S-5 micron, 12 nM) eluting at 3 mL/min with a gradient of 90:10 (0.1% TFA in water:MeCN) to 10:90 over 7.0 min. The starting material has a retention time of 3.85 min. After 20 min at RT, the reaction is heated at 80° C. for an additional 45 min. A new peak by HPLC has a retention time of 0.52 min, corresponding to the desired product. The reaction is cooled, filtered through florisil to remove a black precipitate and concentrated on a Savant Speedvac. The resulting residue is triturated with Et₂O to give a white solid. This material is purified on a preparative reverse phase HPLC column (YMC CombiPrep Pro C18, 50×20 mm I.D., particle size S-5 micron, 12 nM) in two equal aliquots and eluted at 30 ml/min with a gradient of 100:0 (0.1% TFA in water:MeCN) to 70:30 over 5.0 min, then to 10:90 by 7 min. Fractions containing product are combined and concentrated on a Savant Speedvac, then triturated with 10% dimethylsulfoxide (DMSO) in MeCN to yield (S)-2-amino-3-[4-(1,1,4-trioxo-1,2,5-thiadiazolidin-2-yl)-phenyl]-propionic acid as a white solid: [M−1]⁻=298.0.

EXAMPLE 48

(S)-2-Acetylamino-N-{(S)-1-pentylcarbamoyl-2-[4-(1,1,4-trioxo-1,2,5-thiadiazolidin-2-yl)-phenyl]-ethyl}-3-phenyl-propionamide

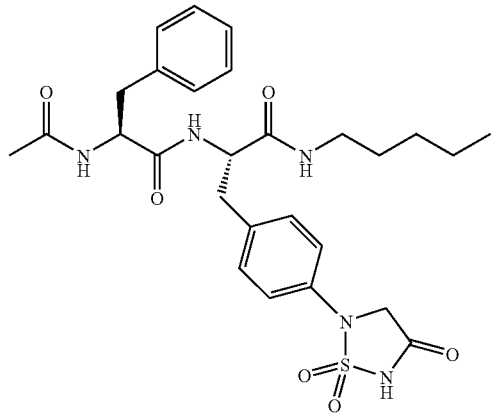

A. ((S)-2-{4-[5-(4-Methoxy-benzyl)-1,1,4-trioxo-1,2,5-thiadiazolidin-2-yl]-phenyl}-1-pentylcarbamoyl-ethyl)-carbamic acid t-butyl ester HOBt (27 mg, 0.175 mmol), pentyl amine (0.020 mL, 0.175 mmol) and 1-ethyl-3-(3-dimethyl-aminopropyl)carbodiimide hydrochloride (37 mg, 0.192 mmol) are added to a solution of the title A compound in Example 47, (S)-2-t-butoxycarbonylamino-3-{4-[5-(4-methoxy-benzyl)-1,1,4-trioxo-1,2,5-thiadiazolidin-2-yl]-phenyl}-propionic acid (91 mg, 0.175 mmol) in CH₂Cl₂ (4 mL) and the reaction is stirred at RT for 2 h. The mixture is concentrated and the product is taken up in EtOAc, washed with 1N aqueous HCl, saturated aqueous NaHCO₃ and brine. The organic solution is dried over anhydrous MgSO₄, filtered and concentrated to give a white solid. Chromatography on a 10 g silica gel RediSep (Isco Inc.) column with a 30 mL/min gradient elution of 30:70 (EtOAc:hexane) to 60:40 over 10 min yields ((S)-2-{4-[5-(4-methoxy-benzyl)-1,1,4-trioxo-1,2,5-thiadiazolidin-2-yl]-phenyl}-1-pentylcarbamoyl-ethyl)-carbamic acid t-butyl ester as a white solid: [M+1]⁺=589.

B. (S)-2-Amino-3-{4-[5-(4-methoxy-benzyl)-1,1,4-trioxo-1,2,5-thiadiazolidin-2-yl]-phenyl}-N-pentyl-propionamide A solution of the title A compond, ((S)-2-(4-[5-{4-methoxy-benzyl)-1,1,4-trioxo-1,2,5-thiadiazolidin-2-yl]-phenyl}-1-pentylcarbamoyl-ethyl)-carbamic acid t-butyl ester (64 mg, 0.108 mmol) in CH₂Cl₂ (1 mL) is treated with TFA (1 mL). After 20 min, the solvent is evaporated under stream of nitrogen. The residue is partitioned between EtOAc and saturated aqueous NaHCO₃, and the organic solution is washed with brine, dried over anhydrous MgSO₄, filtered and concentrated to yield (S)-2-amino-3-{4-[5-(4-methoxybenzyl)-1,1,4-trioxo-1,2,5-thiadiazolidin-2-yl]-phenyl}-N-pentyl-propionamide as a white solid: [M+1]$^+$=489.

C. (S)-2-Acetylamino-N-((S)-2-{4-[5-(4-methoxy-benzyl)-1,1,4-trioxo-1,2,5-thiadiazolidin-2-yl]-phenyl}-1-pentylcarbamoyl-ethyl)-3-phenyl-propionamide HOBt (16 mg, 0.102 mmol), (S)-2-acetylamino-3-phenyl-propionic acid (21 mg, 0.102 mmol) and EDCl (21 mg, 0.112 mmol) are added to a solution of the title B compound, (S)-2-amino-3-{4-[5-(4-methoxy-benzyl)-1,1,4-trioxo-1,2,5-thiadiazolidin-2-yl]-phenyl}-N-pentyl-propionamide (50 mg, 0.102 mmol) in CH$_2$Cl$_2$ (3 mL) and the reaction is stirred at RT for 2.5 h, then concentrated. The residue is taken up in EtOAc, washed with 1N aqueous HCl, saturated NaHCO$_3$ and brine, dried over anhydrous MgSO$_4$, filtered and concentrated to yield (S)-2-acetylamino-N-((S)-2-{4-[5-(4-methoxy-benzyl)-1,1,4-trioxo-1,2,5-thiadiazolidin-2-yl]-phenyl}-1-pentylcarbamoyl-ethyl)-3-phenyl-propionamide as a white foam: [M+1]$^+$=678.

D. (S)-2-Acetylamino-N-{(S)-1-pentylcarbamoyl-2-[4-(1,1,4-trioxo-1,2,5-thiadiazolidin-2-yl)-phenyl]-ethyl}-3-phenyl-propionamide A solution of the title C compound, (S)-2-acetylamino-N-((S)-2-{4-[5-(4-methoxy-benzyl)-1,1,4-trioxo-1,2,5-thiadiazolidin-2-yl]-phenyl}-1-pentylcarbamoyl-ethyl)-3-phenyl-propionamide (49 mg, 0.07 mmol) in TFA (1.4 mL) containing t-butyldimethylsilane (0.035 mL, 0.21 mmol) is heated at 80° C. for 1 h. The reaction is concentrated under nitrogen stream to give an oil which is taken up in 60% MeCN in water. Water (1 mL) is added, and the mixture filtered through a 0.1 micron Acrodisc filter. The resulting mixture is loaded onto a preparative reverse phase HPLC column (YMC CombiPrep Pro C18, 50×20 mm I.D., particle size S-5 micron, 12 nM) in three aliquots and eluted at 30 mL/min with a gradient of 90:10 (0.1% TFA in water: MeCN) to 10:90 over 5 min. Then held at 10:90 until 7 min. Fractions containing product are combined and concentrated on a Savant Speedvac to yield (S)-2-acetylamino-N-((S)-1-pentylcarbamoyl-2-[4-(1,1,4-trioxo-1,2,5-thiadiazolidin-2-yl)-phenyl]-ethyl)-3-phenyl-propionamide as a white solid: [M-1]$^-$=556.

EXAMPLE 49

[4-(2-{(S)-2-((S)2-Acetylamino-3-phenyl-propionylamino)-3-[4-(1,1,4-trioxo-1,2,5-thiadiazolidin-2-yl)-phenyl]-propionylamino}ethyl)-phenyl]-acetic

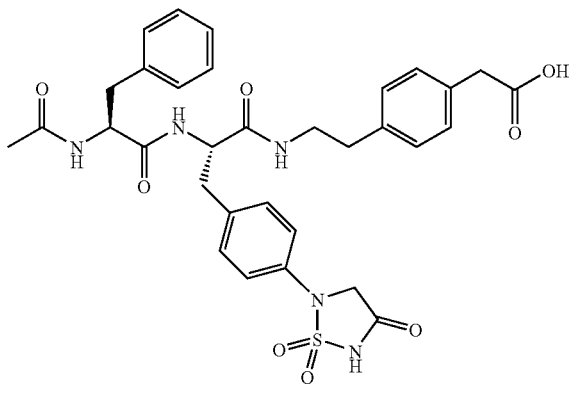

A. (S)-2-Amino-3-{4-[5-(4-methoxy-benzyl)-1,1,4-trioxo-1,2,5-thiadiazolidin-2-yl]-phenyl}-propionic acid benzyl ester The title B compound in Example 46, (S)-2-t-butoxycarbonylamino-3-(4-[S-(4-methoxy-benzyl)-1,1,4-trioxo-1,2,5-thiadiazolidin-2-yl]-phenyl}-propionic acid benzyl ester (100 mg, 0.164 mmol) is dissolved in a mixture of TFA (3.28 mL) and t-butyl-dimethylsilane (0.082 mL, 0.492 mmol) and after 5 min the vial is put on a Savant Speedvac to remove solvets. The residue is triturated with Et$_2$O to give a white solid. This is dissolved in CH$_2$Cl$_2$ and washed with 5% aqueous NaHCO$_3$ solution, dried over anhydrous Na$_2$SO$_4$ and evaporated to yield (S)-2-amino-3-{4-[5-(4-methoxy-benzyl)-1,1,4-trioxo-1,2,5-thiadiazolidin-2-yl]-phenyl}-propionic acid benzyl ester as an oil.

B. (S)-2-((S)-2-Acetylamino-3-phenyl-propionylamino)-3-{4-[5-(4-methoxy-benzyl)-1,1,4-trioxo-1,2,5-thiadiazolidin-2-yl]-phenyl}-propionic acid benzyl ester The title A compound, (S)-2-amino-3-{4-[5-(4-methoxy-benzyl)-1,1,4-trioxo-1,2,5-thiadiazolidin-2-yl]-phenyl}-propionic acid benzyl ester (79 mg, 0.155 mmol) and (S)-2-acetylamino-3-phenyl-propionic acid (33.7 mg, 0.162 mmol) are dissolved in CH$_2$Cl$_2$ (3.1 mL). HOBt (24.8 mg, 0.162 mmol) is added as a solid, followed by EDCl (31.0 mg, 0.162 mmol) and TEA (0.023 mL, 0.162 mmol) in a slurry of CH$_2$Cl$_2$ (1 mL). After 1 h, EtOAc (100 mL) is added and the mixture is washed three times with 2N aqueous HCl (50 mL) followed by saturated aqueous NaHCO$_3$ (50 mL). The EtOAc layer is dried over anhydrous Na$_2$SO$_4$ and concentrated to yield (S)-2-((S)-2-acetylamino-3-phenyl-propionylamino)-3-{4-[5-(4-methoxy-benzyl)-1,1,4-trioxo-1,2,5-thiadiazolidin-2-yl]-phenyl}-propionic acid benzyl ester as a white powder.

C. (S)-2-((S)-2-Acetylamino-3-phenyl-propionylamino)-3-{4-[5-(4-methoxy-benzyl)-1,1,4-trioxo-1,2,5-thiadiazolidin-2-yl]-phenyl}-propionic acid The title B compound, (S)-2-((S)-2-acetylamino-3-phenyl-propionylamino)-3-{4-[5-(4-methoxy-benzyl)-1,1,4-trioxo-1,2,5-thiadiazolidin-2-yl]-phenyl}-propionic acid benzyl ester (104.3 mg, 0.149 mmol) is dissolved in EtOAc:EtOH (50:50; 250 mL) and put in a Parr Shaker bottle along with 10% Palladium on carbon (30 mg). This gas in the bottle is evacuated and replaced with hydrogen at 45 psi and shaken for 1.5 h. The reaction mixture is filtered through celite and concentrated to yield (S)-2-((S)-2-acetylamino-3-phenyl-propionylamino)-3-{4-[5-(4-methoxy-benzyl)-1,1,4-trioxo-1,2,5-thiadiazolidin-2-yl]-phenyl}-propionic acid as a light yellow foam.

D. {4-[2-((S)-2-((S)-2-Acetylamino-3-phenyl-propionylamino)-3-{4-[5-4-methoxy-benzyl)-1,1,4-trioxo-1,2,5-thiadiazolidin-2-yl]-phenyl}-propionylamino)ethyl]-phenyl}-acetic acid t-butyl ester The title C compound, (S)-2-((S)-2-acetylamino-3-phenyl-propionylamino)-3-{4-[5-(4-methoxy-benzyl)-1,1,4-trioxo-1,2,5-thiadiazolidin-2-yl]-phenyl}-propionic acid (83.4 mg, 0.137 mmol) is dissolved in DMF (2 mL) and a solution of [4-(2-amino-ethyl)phenyl]-acetic acid t-butyl ester (32.2 mg, 0.137 mmol) in CH$_2$Cl$_2$ (0.5 mL) is added followed by a solution of HOBt (21.9 mg, 0.143 mmol) in DMF:CH$_2$Cl$_2$ (50:50, 0.5 mL), and finally EDCl (27.6 mg, 0.143 mmol) and TEA (0.020 mL, 0.143 mmol) as a slurry in CH$_2$Cl$_2$ (0.5 mL). The reaction is mixed well to give a homogeneous solution. After 3 h, EtOAc (100 mL) is added and the reaction is washed three times with 2N aqueous HCl (50 mL) and saturated aqueous NaHCO$_3$ (50 mL). EtOAc layer is dried over anhydrous Na$_2$SO$_4$ and concentrated to yield {4-[2-((S)-2-((S)-2-acetylamino-3-phenyl-propionylamino)-3-{4-[5-(4-methoxy-benzyl)-1,1,4-trioxo-1,2,5-thiadiazolidin-2-yl]-phenyl}-propionylamino)-ethyl]-phenyl}-acetic acid t-butyl ester as an oil.

E. [4-(2-{(S)-2-((S)-2-Acetylamino-3-phenyl-propionylamino-3-[4 (1,1,4-trioxo-1,2,5-thiadiazolidin-2-yl)-phenyl]-propionylamino}-ethyl)phenyl]-acetic The title D compound, {4-[2-((S)-2-((S)-2-Acetylamino-3-phenyl-propionylamino)-3-{4-[5-(4-methoxy-benzyl)-1,1,4-trioxo-1,2,5-thiadiazolidin-2-yl]-phenyl}-propionylamino)-ethyl]-phenyl}-acetic acid t-butyl ester (85.4 mg, 0.103 mmol) is dissolved in TFA (2.07 mL) containing t-butyidimethysilane (0.051 mL, 0.309 mmol) and heated in a sealed vial at 80° C. for 1 h. The solvent is removed on a Savant Speedvac, and trituration with Et$_2$O yields a white solid which is dissolved in DMSO:water (1:6, 12 mL) and loaded onto a preparative reverse phase HPLC column (YMC CombiPrep Pro C18, 50×20 mm I.D., particle size S-5 micron, 12 nM) in five aliquots and eluted at 30 mL/min with a gradient of 90:10 (0.1% TFA in water:MeCN) to 10:90 over 5 min. Then held at 10:90 until 7 min. Fractions containing product are combined and concentrated on a Savant Speedvac to give [4-(2-{(S)-2-((S)-2-acetylamino-3-phenyl-propionylamino)-3-[4-(1,1,4-trioxo-1,2,5-thiadiazolidin-2-yl)-phenyl]-propionylamino}-ethyl)-phenyl]-acetic as a white powder: [M−1]$^-$=648.22.

EXAMPLE 50

The following compounds are prepared analogously to Examples 48 and 49.

| Example | Chemical Name | MS [m/z] |
| --- | --- | --- |
| 50-1 | (S)-2-Acetylamino-3-phenyl-N-{(S)-1-(4-phenyl-butylcarbamoyl)-2-[4-(1,1,4-trioxo-1,2,5-thiadiazolidin-2-yl)-phenyl]-ethyl}-propionamide | [M − H]$^-$ = 618 |
| 50-2 | 2-[4-(2-Benzoylamino-2-{1-carbamoyl-2-[4-(1,1,4-trioxo-1,2,5-thiadiazolidin-2-yl)-phenyl]-ethylcarbamoyl}-ethyl)-phenoxy]-malonic acid | [M + 1]$^+$ = 668 |
| 50-3 | (S)-2-(Biphenyl-4-sulfonylamino)-N-pentyl-3-[4-(1,1,4-trioxo-1,2,5-thiadiazolidin-2-yl)-phenyl]-propionamide | [M − 1]$^-$ = 583 |
| 50-4 | (S)-2-(Biphenyl-4-sulfonylamino)-N-(4-phenyl-butyl)-3-[4-(1,1,4-trioxo-1,2,5-thiadiazolidin-2-yl)-phenyl]-propionamide | [M − 1]$^-$ = 645 |
| 50-5 | (S)-2-Benzenesulfonylamino-N-pentyl-3-[4-(1,1,4-trioxo-1,2,5-thiadiazolidin-2-yl)-phenyl]-propionamide | [M − 1]$^-$ = 507 |
| 50-6 | (S)-2-Benzenesulfonylamino-N-(4-phenyl-butyl)-3-[4-(1,1,4-trioxo-1,2,5-thiadiazolidin-2-yl)-phenyl]-propionamide | [M − 1]$^-$ = 569 |
| 50-7 | (S)-2-Benzenesulfonylamino-N-(3,3-diphenyl-propyl)-3-[4-(1,1,4-trioxo-1,2,5-thiadiazolidin-2-yl)-phenyl]-propionamide | [M − 1]$^-$ = 631 |
| 50-8 | (S)-2-Acetylamino-N-[(S)-2-[3-bromo-4-(1,1,4-trioxo-1,2,5-thiadiazolidin-2-yl)-phenyl]-1-(4-phenyl-butylcarbamoyl)-ethyl]-3-phenyl-propionamide | [M − 1]$^-$ = 696, 698 |
| 50-9 | (S)-2-((S)-2-Acetylamino-3-phenyl-propionylamino)-3-[3-bromo-4-(1,1,4-trioxo-1,2,5-thiadiazolidin-2-yl)-phenyl]-N-pentyl-propionamide | [M + 1]$^+$ = 636, 638 |
| 50-10 | (S)-2-Benzenesulfonylamino-3-[3-bromo-4-(1,1,4-trioxo-1,2,5-thiadiazolidin-2-yl)-phenyl]-N-(4-phenyl-butyl)-propionamide | [M + 1]$^+$ = 649, 651 |

EXAMPLE 51

(S)-2-Acetylamino-N-{(S)-1-pentylcarbamoyl-2-[3-(1,1,4-trioxo-1,2,5-thiadiazolidin-2-yl)-phenyl]-ethyl}-3-phenyl-propionamide

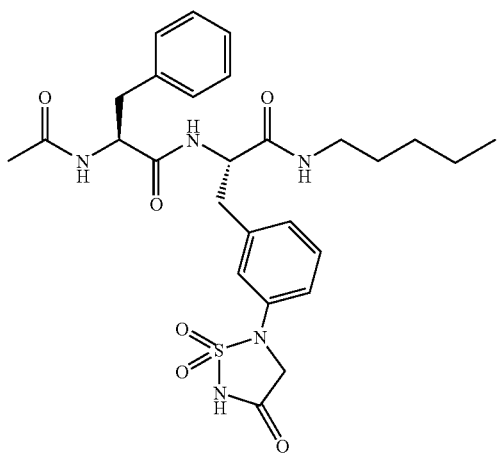

A. N-(2-Trimethylsilylethoxycarbonyl-sulfamoyl)-N-(3-iodo-phenyl)glycine methyl ester To a cooled (ice/salt/water bath) solution of chlorosulfonylisocyanate (3.23 mL, 37.1 mmol) in $CH_2Cl_2$ (100 mL) is added trimethylsilylethanol (5.32 mL, 37.1 mmol). After 1 h, a solution of (3-Iodo-phenylamino)-acetic acid methyl ester (2.7 g, 9.28 mmol) (obtained by alkylation of 3-iodoaniline using the method of Tohru Fukuyama et. al., Tett. Lett. 38 (33) pp. 5831-34,1997) and TEA (5.3 mL, 38.04 mmol) in $CH_2Cl_2$ (50 mL) is added and the reaction is stirred for 2.5 h. The mixture is poured into 400 mL of 1N aqueous HCl and extracted with EtOAc. The EtOAc layer is washed with 1N aqueous HCl, dried over anhydrous $Na_2SO_4$, filtered and concentrated. Chromatography on a 110 g silica gel RediSep (Isco Inc.) column with a 30 mL/min gradient elution of 10:90 (EtOAc:hexane) to 40:60 over 55 min gives an oil. Trituration with $Et_2O$ yields N-(2-trimethylsilylethoxycarbonyl-sulfamoyl)-N-(3-iodo-phenyl)glycine methyl ester as a white solid.

B. 5-(3-Iodo-phenyl)-1,1-dioxo-1,2,5-thiadiazolidin-3-one

A solution of tetrabutylammonium fluoride (5.88 g, 18.67 mmol) in THF (40 mL) is added a solution of the title A compound, N-(2-trimethylsilylethoxycarbonyl-sulfamoyl)-N-(3-iodo-phenyl)glycine methyl ester (2.33 g, 4.5 mmol) in THF (50 mL). The reaction is heated at 90° C. and monitored by reverse phase HPLC (YMC CombiScreen Pro C18, 50×4.6 mm I.D., particle size S-5 micron, 12 nM) eluting at 3 mL/min with a gradient of 90:10 (0.1% TFA in water: MeCN) to 10:90 at 7.0 min. Starting material has a retention time of 4.82 min and the product has a retention time of 2.81 min. After 24 h, the reaction is poured into 500 mL of 1N aqueous HCl and extracted with EtOAc. The organic solution is dried over anhydrous $MgSO_4$, filtered and concentrated to give a yellow solid. Trituration with EtOAc/hexane yields 5-(3-iodo-phenyl)-1,1-dioxo-1,2,5-thiadiazolidin-3-one as a white solid: $(M-H)^-=336.9$.

C. 5-(3-Iodo-phenyl)-2-(4-methoxy-benzyl)-1,1-dioxo-1,2,5-thiadiazolidin-3-one The title B compound, 5-(3-iodo-phenyl)-1,1-dioxo-1,2, 5-thiadiazolidin-3-one (932 mg, 2.76 mmol) is dissolved in tetrahydrofuran (20 mL) in a 40 mL capacity septum capped vial, stirred under argon balloon. Triphenylphosphine (1.47 g, 5.51 mmol) is added as a solid and stirred until dissolved, then 4-methyoxybenzyl alcohol (0.688 mL, 5.51 mmol) is added by syringe. The stirred reaction is cooled in an ice bath, and diethyl azodicarboxylate (0.867 mL, 5.51 mmol) is added slow dropwise by syringe. The reaction is stirred 16 h and then recooled and added more diethyl azodicarboxylate (0.433 mL, 2.26 mmol). After 5H, the reaction is concentrated in vacuo, then taken up in $CH_2Cl_2$ and chromatographed on a 35 g silica gel RediSep column (Isco, Inc.) with a 30 mL/min gradient elution of 0:100 (EtOAc:$CH_2Cl_2$) for 5 min, then to 5:95 over 35 min. Fractions containing product are combined, concentrated and recrystalized with EtOAc/hexanes to yield 5-(3-iodo-phenyl)-2-(4-methoxy-benzyl)-1,1-dioxo-1,2,5-thiadiazolidin-3-one as a white solid: $^1$H-NMR (300 MHz, DMSO-$d_6$) δ 3.76 (s, 3H), 4.79 (s, 2H), 4.88 (s, 2H), 6.92 (d, J=7.5, 2H), 7.27 (t, J=7.5, 1H), 7.33 (d, J=7.5, 2H), 7.39 (d, J=7.5, 1H), 7.63 (d, J=7.5, 1H), 7.67 (s, 1H).

D. (S)-2-t-Butoxycarbonylamino-3-{3-[5-(4-methoxy-benzyl)-1,1,4-trioxo-1,2,5-thiadiazolidin-2-yl]-phenyl}-propionic acid benzyl ester Onto zinc foil (99.9% Aldrich 35, 602-6,118.5 mg, 1.813 mmol) is cut in small pieces is added DMF (freshly distilled from $CaH_2$ under argon, 0.4 mL) and 1,2-dibromoethane (0.006 mL, 0.065 mmol) under argon. The mixture is heated at 50° C. for 10 min, then allowed to cool and trimethylsilyl chloride (0.003 mL, 0.026 mmol) is added. The reaction is stirred for 25 min and a solution of (R)-2-t-butoxycarbonylamino-3-iodo-propionic acid benzyl ester (Fluka, 342 mg, 0.844 mmol) in DMF (1 mL) is added. After 1 h, the mixture is decanted to a solution of the title C compound, 5-(3-iodo-phenyl)-2-(4-methoxy-benzyl)-1,1-dioxo-1,2,5-thiadiazolidin-3-one (300 mg, 0.65 mmol), tri-o-tolylphosphine (29.9 mg, 0.13 mmol) and tris(dibenzylideneacetone)-dipalladium (0) (29.9 mg, 0.033 mmol) in DMF (2 mL). After stirring for 1.5 h, the resulting reaction mixture is poured onto water (100 mL), extracted with EtOAc (2×100 mL). The combined EtOAc layers are washed with water (1×200 mL) and brine (1×200 mL), dried over anhydrous $MgSO_4$, filtered and concentrated to give a yellow oil. This is chromatographed on a 35 g silica gel RediSep column (Isco, Inc.) with a 30 mL/min gradient elution of 0:100 (EtOAc:$CH_2Cl_2$) to 12:88 over 40 min. Fractions containing product are combined and concentrated to yield (S)-2-t-butoxycarbonylamino-3-{3-[5-(4-methoxy-benzyl)-1,1,4-trioxo-1,2,5-thiadiazolidin-2-yl]-phenyl}-propionic acid benzyl ester as a clear oil: $[M+NH_4]^+=627.0$, $[M-HCO_2]^-=654.1$.

E. (S)-2-t-Butoxycarbonylamino-3-{3-[5-(4-methoxy-benzyl)-1,1,4-trioxo-1,2,5-thiadiazolidin-2-yl]-phenyl}-propionic acid The title D compound, (S)-2-t-butoxycarbonylamino-3-{3-[5-(4-methoxy-benzyl)-1,1,4-trioxo-1,2,5-thiadiazolidin-2-yl]-phenyl}-propionic acid benzyl ester (187 mg, 0.307 mmol) is dissolved in a 1:1 mixture of EtOAc:EtOH (50 mL) in a 200 mL Parr bottle. 10% Palladium on carbon (52 mg) is added as a solid and the reaction mixture is hydrogenated on a Parr Shaker Apparatus at 47 psi of hydrogen for 1.33 h. The reaction mixture is filtered through celite and concentrated in vacuo to give (S)-2-t-butoxycarbonylamino-3-{3-[5-(4-methoxy-benzyl)-1,1,4-trioxo-1,2,5-thiadiazolidin-2-yl]-phenyl}-propionic acid as a white foam: $[M-1]^-=518.1$.

F. ((S)-2-{3-[5-(4-Methoxy-benzyl)-1,1,4-trioxo-1,2,5-thiadiazolidin-2-yl]-phenyl}-1-pentylcarbamoyl-ethyl)-carbamic acid t-butyl ester HOBt (46.4 mg, 0.302 mmol), pentyl amine (0.035 mL, 0.302 mmol) and EDCl (63.7 mg, 0.332 mmol) are added to a solution of the title E compound, (S)-2-t-butoxycarbonylamino-3-{3-[5-(4-methoxy-benzyl)-1,1,4-trioxo-1,2,5-thiadiazolidin-2-yl]-phenyl}-propionic acid (157 mg, 0.302 mmol) in $CH_2Cl_2$ (10 mL) and this is stirred at room temperature for 1 h. The reaction is then concentrated in vacuo and the product is taken up in EtOAc. The organic solution is successively washed with 1N aqueous HCl, saturated aqueous $NaHCO_3$ solution and brine, dried over anhydrous $MgSO_4$, filtered and concentrated to yield ((S)-2-{3-[5-(4-methoxy-benzyl)-1,1,4-trioxo-1,2,5-thiadiazolidin-2-yl]-phenyl}-1-pentylcarbamoyl-ethyl)-carbamic acid t-butyl ester as a white film.

G. (S)-2-Amino-3-{3-[5-(4-methoxy-benzyl)-1,1,4-trioxo-1,2,5-thiadiazolidin-2-yl]-phenyl}-N-pentyl-propionamide A solution of the title F compound, ((S)-2-{3-[5-(4-methoxy-benzyl)-1,1,4-trioxo-1,2,5-thiadiazolidin-2-yl]-phenyl}-1-pentylcarbamoyl-ethyl)-carbamic acid t-butyl ester (156 mg, 0.265 mmol) in $CH_2Cl_2$ (1 mL) is treated with TFA (1 mL). After 30 min, the solvent is evaporated under stream of nitrogen. The residue is partitioned between EtOAc and saturated aqueous $NaHCO_3$. The organic solution is washed with brine, dried over anhydrous $MgSO_4$ and concentrated to yield (S)-2-amino-3-{3-[5-(4-methoxy-benzyl)-1,1,4-trioxo-1,2,5-thiadiazolidin-2-yl]-phenyl}-N-pentyl-propionamide as a white solid: $[M+1]^+=489$.

H. (S)-2-Acetylamino-N-((S)-2-{3-[5-(4-methoxy-benzyl)-1,1,4-trioxo-1,2,5-thiadiazolidin-2-yl]-phenyl}-1-pentylcarbamoyl-ethyl)-3-phenyl-propionamide HOBt (40.5 mg, 0.264 mmol), (S)-2-acetylamino-3-phenyl-propionic acid (54.7 mg, 0.264 mmol) and EDCl (50.6 mg, 0.264 mmol) are added to a solution of the title G compound, (S)-2-amino-3-{3-[5-(4-methoxy-benzyl)-1,1,4-trioxo-1,2,5-thiadiazolidin-2-yl]-phenyl}-N-pentyl-propionamide (129 mg, 0.264 mmol) in $CH_2Cl_2$ (5 mL) and stirred at RT for 2 h. The reaction is concentrated and the product is taken up in EtOAc, washed with 1N aqueous HCl, saturated aqueous $NaHCO_3$ and brine, dried over magnesium sulfate, filtered and concentrated to yield (S)-2-acetylamino-N-((S)-2-{3-[5-(4-methoxy-benzyl)-1,1,4-trioxo-1,2,5-thiadiazolidin-2-yl]-phenyl}-1-pentylcarbamoyl-ethyl)-3-phenyl-propionamide as a white solid: $[M+1]^+=678$.

I. (S)-2-Acetylamino-N-{(S)-1-pentylcarbamoyl-2-[3-(1,1,4-trioxo-1,2,5-thiadiazolidin-2-yl)-phenyl]-ethyl}-3-phenyl-propionamide A solution of the title H compound, (S)-2-acetylamino-N-((S)-2-{3-[5-(4-methoxy-benzyl)-1,1,4-trioxo-1,2,5-thiadiazolidin-2-yl]-phenyl}-1-pentylcarbamoyl-ethyl)-3-phenyl-propionamide (124 mg, 0.183 mmol) in TFA (3 mL) containing t-butyidimethylsilane (0.091 mL, 0.548 mmol) is heated at 80° C. for 30 min, then concentrated under nitrogen stream to give an oil containing a fine dark suspension. The product is taken up in 60% MeCN in water and water (1 mL) is added. The mixture filtered through a 0.1 micron Acrodisc filter and the filtrate is loaded onto a preparative reverse phase HPLC column (YMC CombiPrep Pro C18, 50×20 mm I.D., particle size S-5 micron, 12 nM) in five aliquots and eluted at 30 mL/min with a gradient of 90:10 (0.1% TFA in water:MeCN) to 10:90 over 5 min. Then held at 10:90 until 7 min. Fractions containing product are combined and concentrated on a Savant Speedvac to yield (S)-2-acetylamino-N-{(S)-1-pentylcarbamoyl-2-[3-(1,1,4-trioxo-1,2,5-thiadiazolidin-2-yl)-phenyl]-ethyl}-3-phenyl-propionamide as a white foam: $[M+1]^+=558$.

What is claimed is:
1. A compound of the formula

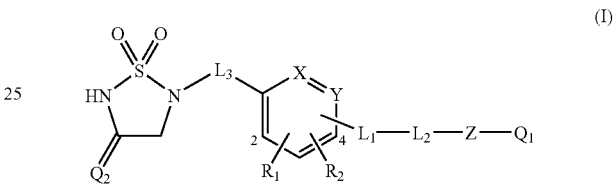

(I)

wherein $R_1$ is hydrogen, halogen, hydroxy, alkoxy, carboxy, cyano, nitro, trifluoromethyl, alkynyl, alkylthio, heteroaralkyl, heteroaralkoxy or heteroaryloxy provided that $R_1$ is located at the 2-position when $L_3$ is —(CHR)$_s$— in which s is zero; or $R_1$ is optionally substituted alkyl, alkenyl, optionally substituted amino, aralkyl, aralkoxy, aralkylthio, aryloxy, arylthio or cycloalkyl provided that a monocyclic aryl group which is substituted at the para position with a methylene or ethylene bridged nitrogen containing heterocycle does not constitute part of $R_1$ when (i) $R_1$ is located at the 2-position and $L_3$ is —(CHR)$_s$— in which s is zero;

(ii) X and Y each are CH; and (iii) $Q_2$ is oxygen; or

C—$R_1$ may be replaced with nitrogen or N→O; or $R_1$ and $R_2$ combined together with the carbon atoms to which $R_1$ and $R_2$ are attached form an optionally substituted fused 5- to 6-membered aromatic or heteroaromatic ring provided that $R_1$ and $R_2$ are attached to carbon atoms adjacent to each other; or $R_2$ is hydrogen, halogen, hydroxy, alkoxy, cyano, trifluoromethyl, nitro, optionally substituted amino, optionally substituted alkyl, alkylthio, aralkyl, heteroaralkyl, aralkoxy, heteroaralkoxy, aralkylthio, aryloxy, heteroaryloxy, arylthio or cycloalkyl; or $R_2$ is —C(O)$R_3$ wherein $R_3$ is hydroxy or optionally substituted alkoxy; or $R_3$ is —$NR_4R_5$ in which $R_4$ and $R_5$ are independently hydrogen, optionally substituted alkyl, alkenyl, alkynyl, cycloalkyl, aryl, heterocyclyl, aralkyl or heteroaralkyl;

$L_1$ is a single bond; or $L_1$ is carbon which combined together with $R_2$ and the carbon atoms to which $L_1$ and $R_2$ are attached form an optionally substituted fused 5- or 6-membered aromatic or heteroaromatic ring provided that $L_1$ and $R_2$ are attached to carbon atoms adjacent to each other; or $L_1$ is CH or nitrogen which taken together with $R_2$ and the carbon atoms to which $L_1$ and $R_2$ are attached form a fused 5- to 7-membered ring which may be interrupted with one or two heteroatoms selected from oxygen, nitrogen and sulfur provided that $L_1$ and $R_2$ are attached to carbon atoms adjacent to each other; or $L_1$ is CH, oxygen, sulfur or nitrogen and $L_2$ is carbon which combined together with $L_1$, $R_2$ and the carbon atoms to which $L_1$ and $R_2$ are attached form an optionally substituted fused 5- or 6-membered aromatic or heteroaromatic ring provided that $L_1$ and $R_2$ are attached to carbon atoms adjacent to each other; or $L_1$ is —$CH_2$—, oxygen, sulfur or —$NR_6$— and $L_2$ is CH which taken together with $L_1$, $R_2$ and the carbon atoms to which $L_1$ and $R_2$ are attached form a fused 5- to 7-membered ring which may be interrupted with one or two heteroatoms selected from oxygen, nitrogen and sulfur wherein $R_6$ is hydrogen, optionally substituted alkyl, aralkyl, heteroaralkyl, alkoxycarbonyl, aryloxycarbonyl, carbamoyl, sulfonyl or acyl provided that $L_1$ and $R_2$ are attached to carbon atoms adjacent to each other;

$L_2$ is —$(CHR_7)_n$— wherein $R_7$ is hydrogen, hydroxy, alkoxy, carboxy, optionally substituted alkyl, cycloalkyl, aryl or heteroaryl;

n is zero or an integer from 1 to 4;

Z is —$(CHR_8)_m$—, —$(CH_2)_mO(CHR_8)_r$—, —$(CH_2)_mS(CHR_8)_r$— or —$(CH_2)_mNR_9(CHR_8)_r$— wherein $R_8$ is hydrogen, optionally substituted alkyl, cycloalkyl, aryl or heterocyclyl;

$R_9$ is hydrogen, optionally substituted alkyl, cycloalkyl, aryl, heterocyclyl, aralkyl, heteroaralkyl, alkoxycarbonyl, aryloxycarbonyl, heteroaryloxycarbonyl, carbamoyl, sulfonyl, acyl or acylamino;

m and r are independently zero or an integer of 1 or 2;

$Q_1$ is hydrogen, optionally substituted alkyl, cycloalkyl, aryl or heterocyclyl provided that (i) $Q_1$ is not 2-phenyloxazol-4-yl when $R_1$ and $R_2$ are hydrogen;

X and Y each are CH;

$L_1$ is a single bond located at the 4-position;

$L_2$ is —$(CHR_7)_n$— wherein n is zero;

$L_3$ is —$(CHR)_s$— wherein s is zero;

Z is —$(CH_2)_mO(CHR_8)_r$— wherein $R_8$ is hydrogen, m is zero and r is 2; and $Q_2$ is oxygen; or (ii) $Q_1$ is not hydrogen when $R_1$ and $R_2$ are hydrogen;

X and Y each are CH;

$L_1$ is a single bond;

$L_2$ is —$(CHR_7)_n$— wherein n is zero;

$L_3$ is —$(CHR)_s$— wherein R is hydrogen and s is 1;

Z is —$(CHR_8)_m$— wherein m is zero; and $Q_2$ is oxygen; or $Q_1$ is $C(O)NR_{4a}R_{5a}$, —$C(O)R_{10}$, —$C(O)OR_{10}$ or —$S(O)_q R_{10}$ wherein $R_{4a}$ and $R_{5a}$ are as defined for $R_4$ and $R_5$; $R_{10}$ is optionally substituted alkyl, cycloalkyl, aryl, heterocyclyl, aralkyl or heteroaralkyl; q is an integer of 1 or 2; or $Q_1$ is a radical of the formula

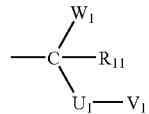

wherein $W_1$ is aryl, heteroaryl, aralkyl or heteroaralkyl; or $W_1$ is —$C(O)R_{3a}$ in which $R_{3a}$ is hydroxy or optionally substituted alkoxy; or $R_{3a}$ is —$NR_{4a}R_{5a}$ in which $R_{4a}$ and $R_{5a}$ are as defined for $R_4$ and $R_5$;

$R_{11}$ is hydrogen, alkyl or aryl;

$U_1$ is —$C(O)$—, —$S(O)_2$— or —$(CH_2)_r$— in which r is as defined for Z;

$V_1$ is hydroxy, alkoxy, aryl, heteroaryl, optionally substituted alkyl or cycloalkyl; or $V_1$ is —$NR_{4b}R_{5b}$ in which $R_{4b}$ and $R_{5b}$ are as defined for $R_4$ and $R_5$ provided that (i) $L_2$ is —$(CHR_7)_n$— in which n is an integer of 1 or 2; and (ii) Z is —$(CHR_8)_m$— in which m is zero; or $Q_1$ is a radical of the formula

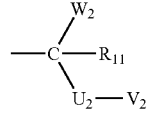

wherein $W_2$ is —$C(O)R_{3a}$ in which $R_{3a}$ is hydroxy or optionally substituted alkoxy; or $R_{3a}$ is —$NR_{4a}R_{5a}$ in which $R_{4a}$ and $R_{5a}$ are as defined for $R_4$ and $R_5$;

$R_{11}$ is hydrogen, alkyl or aryl;

$U_2$ is —$(CH_2)_p$— in which p is zero or 1;

$V_2$ is —$NR_{4b}C(O)R_{5b}$, —$NR_{4b}C(O)OR_{5b}$, —$NR_{4b}C(O)NR_{4c}R_{5b}$ or —$NR_{4b}S(O)_2R_{5b}$ in which $R_{4b}$ and $R_{4c}$ are as defined for $R_4$, and $R_{5b}$ has a meaning as defined for $R_5$ provided that (i) $L_2$ is —$(CHR_7)_n$— in which n is an integer of 1 or 2; and (ii) Z is —$(CHR)_m$— in which m is zero; or $Q_1$ is a radical of the formula

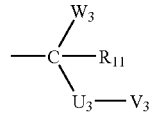

wherein $W_3$ is —$C(O)R_{3a}$ in which $R_{3a}$ is hydroxy or optionally substituted alkoxy; or $R_{3a}$ is —$NR_{4a}R_{5a}$ in which $R_{4a}$ and $R_{5a}$ are as defined for $R_4$ and $R_5$;

$R_{11}$ is hydrogen, alkyl or aryl;

$U_3$ is —$(CH_2)_p$— in which p is zero or 1;

$V_3$ is —NHC(O)CHR$_{4b}$NHC(O)R$_{12}$ wherein R$_{4b}$ is as defined for R$_4$; R$_{12}$ is hydrogen, aryl, heterocyclyl, aralkyl, heteroaralkyl, optionally substituted alkyl, alkoxy or cycloalkyl; or R$_{12}$ is —NR$_{4c}$R$_{5b}$, in which R$_{4c}$ and R$_{5b}$ are as defined for R$_4$ and R$_5$ provided that
(i) L$_2$ is —(CHR$_7$)$_n$— in which n is an integer of 1 or 2; and
(ii) Z is —(CHR)$_m$— in which m is zero;

L$_3$ is —(CHR)$_s$— wherein
R is hydrogen, carboxy, optionally substituted alkyl, cycloalkyl, aryl or heteroaryl;
s is zero or an integer from 1 to 3;

Q$_2$ is oxygen, sulfur or NR$_{13}$ wherein
R$_{13}$ is hydrogen, hydroxy or lower alkyl;

X and Y are —CH—;

or a pharmaceutically acceptable salt thereof; or a prodrug derivative thereof.

2. The compound according to claim 1 wherein
Q$_2$ is oxygen;
or a pharmaceutically acceptable salt thereof; or a prodrug derivative thereof.

3. The compound according to claim 2 of the formula

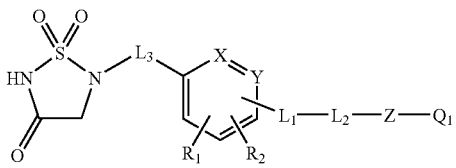

(IA)

wherein
R$_1$ is hydrogen, halogen, hydroxy, alkoxy, trifluoromethyl, alkylthio, heteroaralkyl or heteroaralkoxy provided that R$_1$ is located at the 2-position when L$_3$ is —(CHR)$_s$— in which s is zero; or R$_1$ is optionally substituted alkyl, aralkyl, aralkoxy or aryloxy provided that a monocyclic aryl group which is substituted at the para position with a methylene or ethylene bridged nitrogen containing heterocycle does not constitute part of R$_1$ when
(i) R$_1$ is located at the 2-position and L$_3$ is —(CHR)$_s$— in which s is zero; and
(ii) X and Y each are CH;

R$_2$ is hydrogen; or
R$_2$ is —C(O)R$_3$ wherein
R$_3$ is hydroxy or optionally substituted alkoxy; or
R$_3$ is —NR$_4$R$_5$ in which R$_4$ and R$_5$ are independently hydrogen, optionally substituted alkyl, cycloalkyl, aryl, heterocyclyl, aralkyl or heteroaralkyl;

L$_1$ is a single bond; or
L$_1$ is carbon which combined together with R$_2$ and the carbon atoms to which L$_1$ and R$_2$ are attached form an optionally substituted fused 5- or 6-membered aromatic or heteroaromatic ring provided that L$_1$ and R$_2$ are attached to carbon atoms adjacent to each other; or L$_1$ is CH or nitrogen which taken together with R$_2$ and the carbon atoms to which L$_1$ and R$_2$ are attached form a fused 5- to 7-membered ring which may be interrupted with one or two heteroatoms selected from oxygen, nitrogen and sulfur provided that L$_1$ and R$_2$ are attached to carbon atoms adjacent to each other; or L$_1$ is CH, oxygen, sulfur or nitrogen and L$_2$ is carbon which combined together with L$_1$, R$_2$ and the carbon atoms to which L$_1$ and R$_2$ are attached form an optionally substituted fused 5- or 6-membered aromatic or heteroaromatic ring provided that L$_1$ and R$_2$ are attached to carbon atoms adjacent to each other; or L$_1$ is —CH$_2$—, oxygen, sulfur or —NR$_6$— and L$_2$ is CH which taken together with L$_1$, R$_2$ and the carbon atoms to which L$_1$ and R$_2$ are attached form a fused 5- to 7-membered ring which may be interrupted with one or two heteroatoms selected from oxygen, nitrogen and sulfur wherein
R$_6$ is hydrogen, optionally substituted alkyl, aralkyl, heteroaralkyl, alkoxycarbonyl, aryloxycarbonyl, carbamoyl, sulfonyl or acyl provided that L$_1$ and R$_2$ are attached to carbon atoms adjacent to each other; or L$_2$ is —(CHR$_7$)$_n$— wherein
R$_7$ is hydrogen;
n is zero or an integer of 1 or 2;

Z is —(CHR$_8$)$_m$—, —(CH$_2$)$_m$O(CHR$_8$)$_r$—, —(CH$_2$)$_m$S(CHR$_8$)$_r$— or —(CH$_2$)$_m$NR$_9$(CHR$_8$)$_r$— wherein
R$_8$ is hydrogen or optionally substituted alkyl;
R$_9$ is hydrogen, optionally substituted alkyl, cycloalkyl, aryl, heterocyclyl or acyl;
m and r are independently zero or an integer of 1 or 2;

Q$_1$ is hydrogen, optionally substituted alkyl, cycloalkyl, aryl or heterocyclyl provided that
(i) Q$_1$ is not 2-phenyloxazol-4-yl when
R$_1$ and R$_2$ are hydrogen;
X and Y each are CH;
L$_1$ is a single bond located at the 4-position;
L$_2$ is —(CHR$_7$)$_n$— wherein n is zero;
L$_3$ is —(CHR)$_s$— wherein s is zero; and
Z is —(CH$_2$)$_m$O(CHR$_8$)$_r$— wherein R$_8$ is hydrogen, m is zero and r is 2; or
(ii) Q$_1$ is not hydrogen when
R$_1$ and R$_2$ are hydrogen;
X and Y each are CH;
L$_1$ is a single bond;
L$_2$ is —(CHR$_7$)$_n$— wherein n is zero;
L$_3$ is —(CHR)$_s$—wherein R is hydrogen and s is 1; and
Z is —(CHR$_8$)$_m$— wherein m is zero; or Q$_1$ is —C(O)NR$_{4a}$R$_{5a}$, —C(O)R$_{10}$, —C(O)OR$_{10}$ or —S(O)$_q$R$_{10}$ wherein R$_{4a}$ and R$_{5a}$ are as defined for R$_4$ and R$_5$; R$_{10}$ is optionally substituted alkyl, cycloalkyl, aryl, heterocyclyl, aralkyl or heteroaralkyl; q is an integer of 1 or 2; or Q$_1$ is a radical of the formula

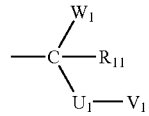

wherein
W$_1$ is aryl, heteroaryl, aralkyl or heteroaralkyl; or
W$_1$ is —C(O)R$_{3a}$ in which R$_{3a}$ is hydroxy or optionally substituted alkoxy; or
R$_{3a}$ is —NR$_{4a}$R$_{5a}$ in which R$_{4a}$ and R$_{5a}$ are as defined for R$_4$ and R$_5$;
R$_{11}$ is hydrogen, alkyl or aryl;
U$_1$ is —C(O)— or —(CH$_2$)$_r$— in which r is as defined for Z;
V$_1$ is hydroxy, alkoxy, aryl, heteroaryl, optionally substituted alkyl or cycloalkyl; or
V$_1$ is —NR$_{4b}$R$_{5b}$ in which R$_{4b}$ and R$_{5b}$ are as defined for R$_4$ and R$_5$ provided that (i) $L_2$ is —$(CHR_7)_n$— in which n is an integer of 1 or 2; and (ii) Z is —$(CHR_8)_m$— in which m is zero; or $Q_1$ is a radical of the formula

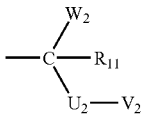

wherein $W_2$ is —$C(O)R_{3a}$ in which $R_{3a}$ is hydroxy or optionally substituted alkoxy; or $R_{3a}$ is —$NR_{4a}R_{5a}$ in which $R_{4a}$ and $R_{5a}$ are as defined for $R_4$ and $R_5$;

$R_{11}$ is hydrogen, alkyl or aryl;

$U_2$ is —$(CH_2)_p$— in which p is zero or 1;

$V_2$ is —$NR_{4b}C(O)R_{5b}$, —$NR_{4b}C(O)OR_{5b}$, —$NR_{4b}C(O)NR_{4c}R_{5b}$ or —$NR_{4b}S(O)_2R_{5b}$ in which $R_{4b}$ and $R_{4c}$ are as defined for $R_4$ and $R_{5b}$ has a meaning as defined for $R_5$ provided that (i) $L_2$ is —$(CHR_7)_n$— in which n is an integer of 1 or 2; and (ii) Z is —$(CHR_8)_m$— in which m is zero; or $Q_1$ is a radical of the formula

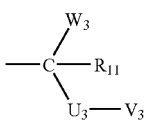

wherein $W_3$ is —$C(O)R_{3a}$ in which $R_{3a}$ is hydroxy or optionally substituted alkoxy; or $R_{3a}$ is —$NR_{3a}R_{4a}$ in which $R_{4a}$ and $R_{5a}$ are as defined for $R_4$ and $R_5$;

$R_{11}$ is hydrogen, alkyl or aryl;

$U_3$ is —$(CH_2)_p$— in which p is zero or 1;

$V_3$ is —$NHC(O)CHR_{4b}NHC(O)R_{12}$ wherein $R_{4b}$ is as defined for $R_4$; $R_{12}$ is hydrogen, aryl, heterocyclyl, aralkyl, heteroaralkyl, optionally substituted alkyl, alkoxy or cycloalkyl; or $R_{12}$ is —$NR_{4c}R_{5b}$, in which $R_{4c}$ and $R_{5b}$ are as defined for $R_4$ and $R_5$ provided that (i) $L_2$ is —$(CHR_7)_n$— in which n is an integer of 1 or 2; and (ii) Z is —$(CHR_8)_m$— in which m is zero;

$L_3$ is —$(CHR)_s$— wherein

R is hydrogen;

s is zero or an integer from 1 to 3;

X and Y each are CH;

or a pharmaceutically acceptable salt thereof; or a prodrug derivative thereof.

4. The compound according to claim 3 of the formula

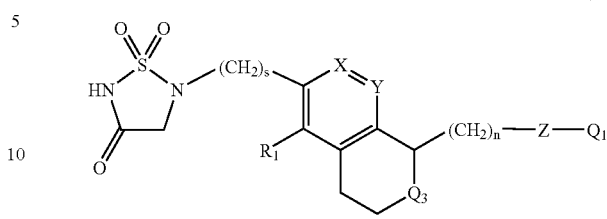

(IB)

wherein $R_1$ is hydrogen, halogen, hydroxy, alkoxy, trifluoromethyl, optionally substituted alkyl, alkylthio, aralkyl, aralkoxy, aryloxy, heteroaralkyl or heteroaralkoxy;

n is zero or an integer of 1 or 2;

Z is —$(CHR_8)_m$—, —$(CH_2)_mO(CHR_8)_r$—, —$(CH_2)_mS(CHR_8)_r$— or —$(CH_2)_mNR_9(CHR_8)_r$— wherein $R_8$ is hydrogen;

$R_9$ is hydrogen, optionally substituted alkyl, cycloalkyl, aryl, heterocyclyl or acyl;

m and r are independently zero or an integer of 1 or 2;

$Q_1$ is hydrogen, optionally substituted alkyl, cycloalkyl, aryl or heterocyclyl; or $Q_1$ is $C(O)NR_{4a}R_{5a}$, —$C(O)R_{10}$, —$C(O)OR_{10}$ or —$S(O)_q R_{10}$ wherein $R_{4a}$ and $R_{5b}$ are independently hydrogen, optionally substituted alkyl, cycloalkyl, aryl, heterocyclyl, aralkyl or heteroaralkyl;

$R_{10}$ is optionally substituted alkyl, cycloalkyl, aryl, heterocyclyl, aralkyl or heteroaralkyl;

q is an integer of 1 or 2;

s is zero or an integer of 1 or 2;

$Q_3$ is O, S or —$NR_{6a}$— wherein $R_{6a}$ is hydrogen, optionally substituted alkyl, aralkyl, heteroaralkyl, alkoxycarbonyl, aryloxycarbonyl, carbamoyl, sulfonyl or acyl;

X and Y each are CH;

or a pharmaceutically acceptable salt thereof; or a prodrug derivative thereof.

5. The compound according to claim 3 of the formula

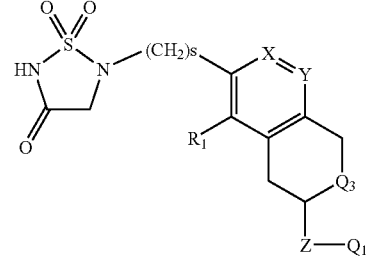

(IC)

wherein $R_1$ is hydrogen, halogen, hydroxy, alkoxy, trifluoromethyl, optionally substituted alkyl, alkylthio, aralkyl, aralkoxy, aryloxy, heteroaralkyl or heteroaralkoxy;

Z is —$(CHR_8)_m$—, —$(CH_2)_mO(CHR_8)_r$—, —$(CH_2)_mS(CHR_8)_r$— or —$(CH_2)_mNR_9(CHR_8)_r$— wherein $R_8$ is hydrogen;

$R_9$ is hydrogen, optionally substituted alkyl, cycloalkyl, aryl, heterocyclyl or acyl;

m and r are independently zero or an integer of 1 or 2;

$Q_1$ is hydrogen, optionally substituted alkyl, cycloalkyl, aryl or heterocyclyl; or $Q_1$ is —C(O)NR$_{4a}$R$_{5a}$, —C(O)R$_{10}$, —C(O)OR$_{10}$ or —S(O)$_q$R$_{10}$ wherein $R_{4a}$ and $R_{5a}$ are independently hydrogen, optionally substituted alkyl, cycloalkyl, aryl, heterocyclyl, aralkyl or heteroaralkyl;

$R_{10}$ is optionally substituted alkyl, cycloalkyl, aryl, heterocyclyl, aralkyl or heteroaralkyl;

q is an integer of 1 or 2;

s is zero or an integer of 1 or 2;

$Q_3$ is O, S or —NR$_{6a}$— wherein $R_{6a}$ is hydrogen, optionally substituted alkyl, aralkyl, heteroaralkyl, alkoxycarbonyl, aryloxycarbonyl, carbamoyl, sulfonyl or acyl;

X and Y are CH;

or a pharmaceutically acceptable salt thereof; or a prodrug derivative thereof.

6. The compound according to claim 3 wherein $R_2$ is hydrogen;

$L_1$ is a single bond;

$L_2$ is —(CH$_2$)$_n$— in which n is zero or an integer of 1 or 2;

or a pharmaceutically acceptable salt thereof; or a prodrug derivative thereof.

7. The compound according to claim 6 of the formula

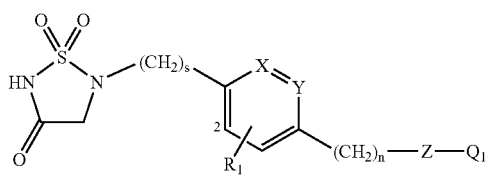

(ID)

wherein $R_1$ is hydrogen, halogen, hydroxy, alkoxy, trifluoromethyl or alkylthio provided that $R_1$ is located at the 2-position when s is zero; or $R_1$ is optionally substituted alkyl, aralkyl, aralkoxy or aryloxy provided that a monocyclic aryl group which is substituted at the para position with a methylene or ethylene bridged nitrogen containing heterocycle does not constitute part of $R_1$ when (i) $R_1$ is located at the 2-position and s is zero; and (ii) X and Y each are CH;

n is zero or an integer of 1 or 2;

s is zero or 1;

Z is —(CHF$_8$)$_m$—, —(CH$_2$)$_m$O(CHR$_8$)$_r$—, —(CH$_2$)$_m$S(CHR$_8$)$_r$— or —(CH$_2$)$_m$NR$_9$(CHR$_8$)$_r$— wherein $R_8$ is hydrogen;

$R_9$ is hydrogen, optionally substituted alkyl, cycloalkyl, aryl, heteroaryl or acyl;

m and r are independently zero or an integer of 1 or 2;

$Q_1$ is hydrogen, optionally substituted alkyl, cycloalkyl, aryl or heterocyclyl provided that (i) $Q_1$ is not 2-phenyloxazol-4-yl when $R_1$ is hydrogen;

X and Y each are CH;

n is zero;

s is zero; and

Z is —(CH$_2$)$_m$O(CHR$_8$)$_r$— wherein $R_8$ is hydrogen, m is zero and r is 2; or (ii) $Q_1$ is not hydrogen when $R_1$ is hydrogen;

X and Y each are CH;

n is zero;

s is 1;

Z is —(CHR$_8$)$_m$— wherein m is zero; or $Q_1$ is C(O)NR$_{4a}$R$_{5a}$, —C(O)R$_{10}$, —C(O)OR$_{10}$ or —S(O)$_q$R$_{10}$ wherein $R_{4a}$ and $R_{5a}$ are independently hydrogen, optionally substituted alkyl, cycloalkyl, aryl, heterocyclyl, aralkyl or heteroaralkyl;

$R_{10}$ is optionally substituted alkyl, cycloalkyl, aryl, heterocyclyl, aralkyl or heteroaralkyl;

q is an integer of 1 or 2; or $Q_1$ is a radical of the formula

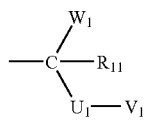

wherein $W_1$ is aryl, heteroaryl, aralkyl or heteroaralkyl; or $W_1$ is —C(O)R$_{3a}$ in which R$_{3a}$ is hydroxy or optionally substituted alkoxy; or $R_{3a}$ is —NR$_{4a}$R$_{5a}$ in which R$_{4a}$ and R$_{5a}$ are independently hydrogen, optionally substituted alkyl, cycloalkyl, aryl, heterocyclyl, aralkyl or heteroaralkyl;

$R_{11}$ is hydrogen, alkyl or aryl;

$U_1$ is —C(O)— or —(CH$_2$)$_r$— in which r is as defined for Z;

$V_1$ is hydroxy, alkoxy, aryl, heteroaryl, optionally substituted alkyl or cycloalkyl; or $V_1$ is —NR$_{4b}$R$_{5b}$ in which R$_{4b}$ and R$_{5b}$ are as defined for R$_{4a}$ and R$_{5a}$ provided that (i) n is an integer of 1 or 2; and (ii) Z is —(CHR$_8$)$_m$— in which m is zero; or $Q_1$ is a radical of the formula

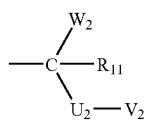

wherein $W_2$ is —C(O)R$_{3a}$ in which R$_{3a}$ is hydroxy or optionally substituted alkoxy; or $R_{3a}$ is —NR$_{4a}$R$_{5a}$ in which R$_{4a}$ and R$_{5a}$ are independently hydrogen, optionally substituted alkyl, cycloalkyl, aryl, heterocyclyl, aralkyl or heteroaralkyl;

$R_{11}$ is hydrogen, alkyl or aryl;

$U_2$ is —(CH$_2$)$_p$— in which p is zero or 1;

$V_2$ is —NR$_{4b}$C(O)R$_{5b}$, —NR$_{4b}$C(O)OR$_{5b}$, —NR$_{4b}$C(O)NR$_{4c}$R$_{5b}$ or —NR$_{4b}$S(O)$_2$R$_{5b}$ in which R$_{4b}$ and R$_{4c}$ are as defined for R$_{4a}$, and R$_{5b}$ has a meaning as defined for R$_{5a}$ provided that (i) n is an integer of 1 or 2; and (ii) Z is —(CHR$_8$)$_m$— in which m is zero; or $Q_1$ is a radical of the formula

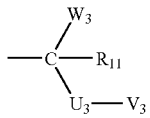

wherein
$W_3$ is —C(O)$R_{3a}$ in which $R_{3a}$ is hydroxy or optionally substituted alkoxy; or
$R_{3a}$ is —$NR_{4a}R_{5a}$ in which $R_{4a}$ and $R_{5a}$ are independently hydrogen, optionally substituted alkyl, cycloalkyl, aryl, heterocyclyl, aralkyl or heteroaralkyl;
$R_{11}$ is hydrogen, alkyl or aryl;
$U_3$ is —(CH$_2$)$_r$— in which r is zero or 1;
$V_3$ is —NHC(O)CHR$_{4b}$NHC(O)R$_{12}$ wherein $R_{4b}$ is as defined for $R_{4a}$; $R_{12}$ is hydrogen, aryl, heterocyclyl, aralkyl, heteroaralkyl, optionally substituted alkyl, alkoxy or cycloalkyl; or
$R_{12}$ is —$NR_{4c}R_{5b}$ in which $R_{4c}$ is as defined for $R_{4a}$, and $R_{5b}$ has a meaning as defined for $R_{5a}$ provided that
(i) n is an integer of 1 or 2; and
(ii) Z is —(CHR$_8$)$_m$— in which m is zero;
X and Y each are CH;
or a pharmaceutically acceptable salt thereof; or a prodrug derivative thereof.

8. The compound according to claim 7 wherein
$R_1$ is bromide;
X and Y each are CH;
or a pharmaceutically acceptable salt thereof; or a prodrug derivative thereof.

9. The compound according to claim 7 wherein
n is zero;
s is 1;
Z is —(CH$_2$)$_m$— in which m is zero;
$Q_1$ is —C(O)$NR_{4a}R_{5a}$, —C(O)$R_{10}$, —C(O)$OR_{10}$ or —S(O)$_q R_{10}$ wherein
$R_{4a}$ and $R_{5a}$ are independently hydrogen, optionally substituted alkyl, cycloalkyl, aryl, heterocyclyl, aralkyl or heteroaralkyl;
$R_{10}$ is optionally substituted alkyl, cycloalkyl, aryl, heterocyclyl, aralkyl or heteroaralkyl;
q is an integer of 1 or 2;
or a pharmaceutically acceptable salt thereof; or a prodrug derivative thereof.

10. The compound according to claim 7 wherein
n is an integer of 1 or 2;
Z is —(CH$_2$)$_m$O(CH$_2$)$_r$— or —(CH$_2$)$_m$S(CH$_2$)$_r$— wherein
m is zero;
r is zero or 1;
$Q_1$ is optionally substituted alkyl, cycloalkyl, aryl or heterocyclyl;
or a pharmaceutically acceptable salt thereof; or a prodrug derivative thereof.

11. The compound according to claim 7 wherein
n is an integer of 1 or 2;
Z is —(CH$_2$)$_m$NR$_9$(CH$_2$)$_r$— wherein $R_9$ is hydrogen, optionally substituted alkyl, cycloalkyl, aryl, heteroaryl or acyl;
m is zero;
r is zero or 1;
$Q_1$ is optionally substituted alkyl, cycloalkyl, aryl or heterocyclyl; or
$Q_1$ is C(O)$NR_{4a}R_{5a}$, —C(O)$R_{10}$, —C(O)$OR_{10}$ or —S(O)$_q R_{10}$ wherein
$R_{4a}$ and $R_{5a}$ are independently hydrogen, optionally substituted alkyl, cycloalkyl, aryl, heterocyclyl, aralkyl or heteroaralkyl;
$R_{10}$ is optionally substituted alkyl, cycloalkyl, aryl, heterocyclyl, aralkyl or heteroaralkyl;
q is an integer of 1 or 2;
or a pharmaceutically acceptable salt thereof; or a prodrug derivative thereof.

12. The compound according to claim 7 wherein
n is an integer of 1 or 2;
Z is —(CH$_2$)$_m$— wherein m is zero;
$Q_1$ is a radical of the formula

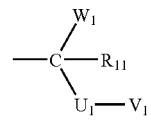

wherein
$W_1$ is aryl, heteroaryl, aralkyl or heteroaralkyl;
$R_{11}$ is hydrogen, alkyl or aryl;
$U_1$ is —C(O)— or —(CH$_2$)$_r$— in which r is zero;
$V_1$ is aryl, heteroaryl, optionally substituted alkyl or cycloalkyl;
or a pharmaceutically acceptable salt thereof; or a prodrug derivative thereof.

13. The compound according to claim 7 wherein
n is 1;
Z is —(CH$_2$)$_m$— wherein m is zero;
$Q_1$ is a radical of the formula

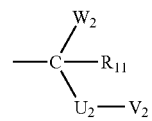

wherein
$W_2$ is —C(O)$R_{3a}$ in which $R_{3a}$ is —$NR_{4a}R_{5a}$, and $R_{4a}$ and $R_{5a}$ are independently hydrogen, optionally substituted alkyl, cycloalkyl, aryl, heterocyclyl, aralkyl or heteroaralkyl;
$R_{11}$ is hydrogen;
$U_2$ is —(CH$_2$)$_p$— in which p is zero;
$V_2$ is —NR$_{4b}$C(O)R$_{5b}$, —NR$_{4b}$C(O)OR$_{5b}$, —NR$_{4b}$C(O)NR$_{4c}$R$_{5b}$ or —NR$_{4b}$S(O)$_2$R$_{5b}$ in which $R_{4b}$ and $R_{4c}$ are as defined for $R_{4a}$, and $R_{5b}$ has a meaning as defined for $R_{5b}$;
or a pharmaceutically acceptable salt thereof; or a prodrug derivative thereof.

14. The compound according to claim 7 wherein
n is 1;
Z is —(CH$_2$)$_m$— wherein m is zero;
Q$_1$ is a radical of the formula

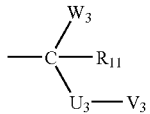

wherein
W$_3$ is —C(O)R$_{3a}$ in which R$_{3a}$ is —NR$_{4a}$R$_{5a}$, and R$_{4a}$ and R$_{5a}$ are independently hydrogen, optionally substituted alkyl, cycloalkyl, aryl, heterocyclyl, aralkyl or heteroaralkyl;
R$_{11}$ is hydrogen;
U$_3$ is —(CH$_2$)$_p$— in which p is zero;
V$_3$ is —NHC(O)CHR$_{4b}$NHC(O)R$_{12}$ wherein R$_{4b}$ is as defined for R$_{4a}$; R$_{12}$ is hydrogen, aryl, heterocyclyl, aralkyl, heteroaralkyl, optionally substituted alkyl or alkoxy; or
R$_{12}$ is —NR$_{4c}$R$_{5b}$ in which R$_{4c}$ and R$_{5b}$ are as defined for R$_{4a}$ and R$_{5a}$;
or a pharmaceutically acceptable salt thereof; or a prodrug derivative thereof.

15. The compound according to claim 1 which is selected from:
5-Naphthalen-1-ylmethyl-1,1-dioxo-1,2,5-thiadiazolidin-3-one;
N-[3-(1,1,4-Trioxo-1,2,5-thiadiazolidin-2-ylmethyl)-benzyl]-acetamide;
[3-(1,1,4-Trioxo-1,2,5-thiadiazolidin-2-ylmethyl)-benzyl]-carbamic acid t-butyl ester;
5-(4-Aminomethyl-benzyl)-1,1-dioxo-1,2,5-thiadiazolidin-3-one;
N-[4-(1,1,4-Trioxo-1,2,5-thiadiazolidin-2-ylmethyl)-benzyl]-acetamide;
[4-(1,1,4-Trioxo-1,2,5-thiadiazolidin-2-ylmethyl)-benzyl]-carbamic acid t-butyl ester;
3-Phenyl-N-[4-(1,1,4-trioxo-1,2,5-thiadiazolidin-2-ylmethyl)-benzyl]-propionamide;
5-(3-Iodo-benzyl)-1,1-dioxo-1,2,5-thiadiazolidin-3-one;
5-(3-Nitro-benzyl)-1,1-dioxo-1,2,5-thiadiazolidin-3-one;
5-(3-Amino-benzyl-1,1-dioxo-1,2,5-thiadiazolidin-3-one;
N-[3-(1,1,4-Trioxo-1,2,5-thiadiazolidin-2-ylmethyl)-phenyl]-acetamide;
5-(4-Amino-benzyl)-1,1-dioxo-1,2,5-thiadiazolidin-3-one;
N-[3-(1,1,4-Trioxo-1,2,5-thiadiazolidin-2-ylmethyl)-phenyl]-butyramide;
1-Propyl-3-[3-(1,1,4-trioxo-1,2,5-thiadiazolidin-2-ylmethyl)-phenyl]-urea;
4-(1,1,4-Trioxo-1,2,5-thiadiazolidin-2-ylmethyl)-benzoic acid methyl ester;
4-(1,1,4-Trioxo-1,2,5-thiadiazolidin-2-ylmethyl)-benzoic acid;
2-(1,1,4-Trioxo-1,2,5-thiadiazolidin-2-ylmethyl)-benzoic acid;
5-(2-Methyl-benzyl)-1,1-dioxo-1,2,5-thiadiazolidin-3-one;
5-(4-Methoxy-benzyl)-1,1-dioxo-1,2,5-thiadiazolidin-3-one;
5-(4-Amino-2-bromo-benzyl)-1,1-dioxo-1,2,5-thiadiazolidin-3-one;
N-[4-(1,1,4-Trioxo-1,2,5-thiadiazolidin-2-ylmethyl)-phenyl]-acetamide;
N-[4-(1,1,4-Trioxo-1,2,5-thiadiazolidin-2-ylmethyl)-phenyl]-methanesulfonamide;
N-[4-(1,1,4-Trioxo-1,2,5-thiadiazolidin-2-ylmethyl)-benzyl]-methanesulfonamide;
5-(4-Methyl-benzyl)-1,1-dioxo-1,2,5-thiadiazolidin-3-one;
Amino-[4-(1,1,4-trioxo-1,2,5-thiadiazolidin-2-ylmethyl)-phenyl]-acetic acid;
2-Amino-N-propyl-2-[2-(1,1,4-trioxo-1,2,5-thiadiazolidin-2-ylmethyl)-phenyl]-acetamide;
2-Amino-N-propyl-2-[4-(1,1,4-trioxo-1,2,5-thiadiazolidin-2-ylmethyl)-phenyl]-acetamide;
2,2,2-Trifluoro-N-{propylcarbamoyl-[4-(1,1,4-trioxo-1,2,5-thiadiazolidin-2-ylmethyl)-phenyl]-methyl}-acetamide;
2-Methanesulfonylamino-N-propyl-2-[4-(1,1,4-trioxo-1,2,5-thiadiazolidin-2-ylmethyl)-phenyl]-acetamide;
2-Acetylamino-N-propyl-3-[4-(1,1,4-trioxo-1,2,5-thiadiazolidin-2-ylmethyl)-phenyl]-propionamide;
2-Acetylamino-2-[4-(1,1,4-trioxo-1,2,5-thiadiazolidin-2-ylmethyl)-benzyl]-malonic acid diethyl ester;
2-Amino-N-propyl-3-[4-(1,1,4-trioxo-1,2,5-thiadiazolidin-2-ylmethyl)-phenyl]-propionamide;
2-Acetylamino-3-[4-(1,1,4-trioxo-1,2,5-thiadiazolidin-2-ylmethyl)-phenyl]-propionic acid ethyl ester;
Phenyl-(1,1,4-trioxo-1,2,5-thiadiazolidin-2-yl)-acetic acid;
1,1-Dioxo-5-phenethyl-1,2,5-thiadiazolidin-3-one;
5-[2-(4-Methyl-thiazol-5-yl)-ethyl]-1,1-dioxo-1,2,5-thiadiazolidin-3-one;
5-[2-(3,4-Dimethoxy-phenyl)-ethyl]-1,1-dioxo-1,2,5-thiadiazolidin-3-one;
5-[2-(2-Chloro-phenyl)-ethyl]-1,1-dioxo-1,2,5-thiadiazolidin-3-one;
5-[2-(4-Amino-phenyl)-ethyl]-1,1-dioxo-1,2,5-thiadiazolidin-3-one;
2,2,2-Trifluoro-N-{4-[2-(1,1,4-trioxo-1,2,5-thiadiazolidin-2-yl)ethyl]-phenyl}-acetamide;
N-{4-[2-(1,1,4-Trioxo-1,2,5-thiadiazolidin-2-yl)-ethyl]-phenyl}-butyramide;
3-Phenyl-2-(1,1,4-trioxo-1,2,5-thiadiazolidin-2-yl)-propionic acid;
5-[2-(3-Amino-phenyl)-ethyl]-1,1-dioxo-1,2,5-thiadiazolidin-3-one;
5-(4-Aminomethyl-naphthalen-1-ylmethyl)-1,1-dioxo-1,2,5-thiadiazolidin-3-one;
5-(1-Ethyl-2-methyl-1H-benzimidazol-5-ylmethyl)-1,1-dioxo-1,2,5-thiadiazolidin-3-one;
5-[2-Methyl-1-(3-methyl-butyl)-1H-benzimidazol-5-ylmethyl]-1,1-dioxo-1,2,5-thiadiazolidin-3-one;
5-(4-Methoxy-quinolin-7-ylmethyl)-1,1-dioxo-1,2,5-thiadiazolidin-3-one;
5-(4-Isobutoxy-quinolin-7-ylmethyl)-1,1-dioxo-1,2,5-thiadiazolidin-3-one;
{(1-Butylcarbamoyl-3-phenyl-propyl)-[4-(1,1,4-trioxo-1,2,5-thiadiazolidin-2-ylmethyl)-benzoyl]-amino}-acetic acid;
{[Butylcarbamoyl-(4-ethyl-phenyl)-methyl]-[4-(1,1,4-trioxo-1,2,5-thiadiazolidin-2-ylmethyl)-benzoyl]-amino}-acetic acid;
{[Butylcarbamoyl-(3-phenoxy-phenyl)-methyl]-[4-(1,1,4-trioxo-1,2,5-thiadiazolidin-2-ylmethyl)-benzoyl]-amino}-acetic acid;

{[Butylcarbamoyl-(4-methoxy-phenyl)-methyl]-[4-(1,1,4-trioxo-1,2,5-thiadiazolidin-2-ylmethyl)-benzoyl]-amino}-acetic acid;
{[(2-Bromo-phenyl)-butylcarbamoyl-methyl]-[4-(1,1,4-trioxo-1,2,5-thiadiazolidin-2-ylmethyl)-benzoyl]-amino}-acetic acid;
(Butylcarbamoyl-naphthalen-2-yl-methyl)-[4-(1,1,4-trioxo-1,2,5-thiadiazolidin-2-ylmethyl)-benzoyl]-amino}-acetic acid;
{[Butylcarbamoyl-(4-chloro-phenyl)-methyl]-[4-(1,1,4-trioxo-1,2,5-thiadiazolidin-2-ylmethyl)-benzoyl]-amino}-acetic acid;
{[(3-Benzyloxy-phenyl)-butylcarbamoyl-methyl]-[4-(1,1,4-trioxo-1,2,5-thiadiazolidin-2-ylmethyl)-benzoyl]-amino}-acetic acid;
{((E)-1-Butylcarbamoyl-3-phenyl-allyl)-[4-(1,1,4-trioxo-1,2,5-thiadiazolidin-2-ylmethyl)-benzoyl]-amino}-acetic acid;
N-(1-Butylcarbamoyl-3-phenyl-propyl)-N-(4-(1,1,4-trioxo-1,2,5-thiazodiazolidin-2-ylmethyl)-benzoyl)amino-acetic acid;
4-(1,1,4-Trioxo-1,2,5-thiadiazolidin-2-ylmethyl)-benzoic acid 4-methanesulfonyl-benzyl ester;
4-(1,1,4-Trioxo-1,2,5-thiadiazolidin-2-ylmethyl)-benzoic acid 3-chloro-benzyl ester;
4-(1,1,4-Trioxo-1,2,5-thiadiazolidin-2-ylmethyl)-benzoic acid 4-butyl-benzyl ester;
4-(1,1,4-Trioxo-1,2,5-thiadiazolidin-2-ylmethyl)-benzoic acid 4-hydroxymethyl-benzyl ester;
4-(1,1,4-Trioxo-1,2,5-thiadiazolidin-2-ylmethyl)-benzoic acid 2-phenethyl-benzyl ester;
4-(1,1,4-Trioxo-1,2,5-thiadiazolidin-2-ylmethyl)-benzoic acid biphenyl-2-ylmethyl ester;
4-(1,1,4-Trioxo-1,2,5-thiadiazolidin-2-ylmethyl)-benzoic acid 4-difluoromethoxy-benzyl ester;
4-(1,1,4-Trioxo-1,2,5-thiadiazolidin-2-ylmethyl)-benzoic acid 5-(carboxy-difluoro-methyl)-thiophen-2-ylmethyl ester;
[4-(1,1,4-Trioxo-1,2,5-thiadiazolidin-2-ylmethyl)-phenylmethanesulfonyl]-acetic acid ethyl ester;
[4-(1,1,4-Trioxo-1,2,5-thiadiazolidin-2-ylmethyl)-benzylsulfanyl]-acetic acid ethyl ester;
5-[4-(3-Methyl-butylsulfanylmethyl)-benzyl]-1,1-dioxo-1,2,5-thiadiazolidin-3-one;
4-(1,1,4-Trioxo-1,2,5-thiadiazolidin-2-ylmethyl)-benzoic acid 2-ethyl-butyl ester;
4-(1,1,4-Trioxo-1,2,5-thiadiazolidin-2-ylmethyl)-benzoic acid cyclobutylmethyl ester;
4-(1,1,4-Trioxo-1,2,5-thiadiazolidin-2-ylmethyl)-benzoic acid cyclopentylmethyl ester;
4-(1,1,4-Trioxo-1,2,5-thiadiazolidin-2-ylmethyl)-benzoic acid 2-methyl-pentyl ester;
4-(1,1,4-Trioxo-1,2,5-thiadiazolidin-2-ylmethyl)-benzoic acid 2,4,4-trimethyl-pentyl ester;
4-(1,1,4-Trioxo-1,2,5-thiadiazolidin-2-ylmethyl)-benzoic acid cyclohexylmethyl ester;
4-(1,1,4-Trioxo-1,2,5-thiadiazolidin-2-ylmethyl)-benzoic acid 1,2-dimethyl-propyl ester;
4-(1,1,4-Trioxo-1,2,5-thiadiazolidin-2-ylmethyl)-benzoic acid cyclopentyl ester;
4-(1,1,4-Trioxo-1,2,5-thiadiazolidin-2-ylmethyl)-benzoic acid 2-methyl-butyl ester;
4-(1,1,4-Trioxo-1,2,5-thiadiazolidin-2-ylmethyl)-benzoic acid 2-methylsufanyl-ethyl ester;
4-(1,1,4-Trioxo-1,2,5-thiadiazolidin-2-ylmethyl)-benzoic acid 2-carboxymethylsulfanyl-ethyl ester;
4-(1,1,4-Trioxo-1,2,5-thiadiazolidin-2-ylmethyl)-benzoic acid 5-nitro-furan-2-ylmethyl ester;
4-(1,1,4-Trioxo-1,2,5-thiadiazolidin-2-ylmethyl)-benzoic acid pyridin-2-ylmethyl ester;
4-(1,1,4-Trioxo-1,2,5-thiadiazolidin-2-ylmethyl)-benzoic acid 3-hydroxymethyl-benzyl ester;
4-(1,1,4-Trioxo-1,2,5-thiadiazolidin-2-ylmethyl)-benzoic acid 3-methanesulfonyl-benzyl ester;
(4-{4-[4-(1,1,4-Trioxo-1,2,5-thiadiazolidin-2-ylmethyl)-benzoylamino]-butyl}phenyl)-acetic acid;
(4-{3-[4-(1,1,4-Trioxo-1,2,5-thiadiazolidin-2-ylmethyl)-benzoylamino]-propyl}-phenyl)-acetic acid;
4-(1,1,4-Trioxo-1,2,5-thiadiazolidin-2-ylmethyl)-benzoic acid 5-dimethylaminomethyl-furan-2-ylmethyl ester;
(S)-2-Acetylamino-N{(S)-1-pentylcarbamoyl-2-[3-(1,1,4-trioxo-1,2,5-thiadiazolidin-2-ylmethyl)-phenyl]-ethyl}-3-phenyl-propionamide;
5-(1H-Indol-5-ylmethyl)-1,1-dioxo-1,2,5-thiadiazolidin-3-one;
1,1-Dioxo-5-(3,4,5-trimethoxy-benzyl)-1,2,5-thiadiazolidin-3-one;
5-[4-(4-Benzyl-piperazin-1-ylmethyl)-benzyl]-1,1-dioxo-1,2,5-thiadiazolidin-3-one;
[4-(1,1,4-Trioxo-1,2,5-thiadiazolidin-2-ylmethyl)-phenyl]-acetic acid;
5-(4-Benzoyl-benzyl)-1,1-dioxo-1,2,5-thiadiazolidin-3-one;
5-Naphthalen-2-ylmethyl-1,1-dioxo-1,2,5-thiadiazolidin-3-one;
5-[4-(4-Methyl-pentanoyl)-benzyl]-1,1-dioxo-1,2,5-thiadiazolidin-3-one;
5-[3-(2-Fluoro-phenoxy)-benzyl]-1,1-dioxo-1,2,5-thiadiazolidin-3-one;
3-{2-[4-(1,1,4-Trioxo-1,2,5-thiadiazolidin-2-ylmethyl)-phenyl]-ethoxy}-benzoic acid;
1-(3-Methyl-butyl)-6-(1,1,4-trioxo-1,2,5-thiadiazolidin-2-ylmethyl)-1H-quinolin-2-one;
2-Amino-N-[4-(1,1,4-trioxo-1,2,5-thiadiazolidin-2-ylmethyl)-benzyl]-acetamide;
4-(1,1,4-Trioxo-1,2,5-thiadiazolidin-2-ylmethyl benzoic acid 4-carboxy-benzyl ester;
1,1-Dioxo-5-(3-phenoxy-benzyl)-1,2,5-thiadiazolidin-3-one;
3-Nitro-4-(1,1,4-trioxo-1,2,5-thiadiazolidin-2-ylmethyl)-benzoic acid;
5-(4-Hydroxymethyl-benzyl)-1,1-dioxo-1,2,5-thiadiazolidin-3-one;
2-Amino-4-(1,1,4-trioxo-1,2,5-thiadiazolidin-2-ylmethyl)-benzoic acid methyl ester;
5-(4-Hydroxy-benzyl)-1,1-dioxo-1,2,5-thiadiazolidin-3-one;
5-Nitro-2-(1,1,4-trioxo-1,2,5-thiadiazolidin-2-ylmethyl)-benzoic acid;
5-Amino-2-(1,1,4-trioxo-1,2,5-thiadiazolidin-2-ylmethyl)-benzoic acid;
5-(4-Chloro-3-methoxy-5-nitro-benzyl)-1,1-dioxo-1,2,5-thiadiazolidin-3-one;
5-(2-Nitro-benzyl)-1,1-dioxo-1,2,5-thiadiazolidin-3-one;
5-(3-Methyl-2-nitro-benzyl)-1,1-dioxo-1,2,5-thiadiazolidin-3-one;
5-(3-Methyl-benzyl)-1,1-dioxo-1,2,5-thiadiazolidin-3-one;
1,1-Dioxo-5-(3-phenyl-propyl)-1,2,5-thiadiazolidin-3-one;
5-(4-Butoxy-benzyl)-1,1-dioxo-1,2,5-thiadiazolidin-3-one;

1,1-Dioxo-5-(2-trifluoromethyl-benzyl)-1,2,5-thiadiazolidin-3-one;
3-Amino-4-(1,1,4-trioxo-1,2,5-thiadiazolidin-2-ylmethyl)-benzoic acid;
4-[5-Amino-2-(1,1,4-trioxo-1,2,5-thiadiazolidin-2-ylmethyl)-phenyl]-butyric acid;
5-(2-Methyl-3-nitro-benzyl)-1,1-dioxo-1,2,5-thiadiazolidin-3-one;
5-(4-Methyl-3-nitro-benzyl)-1,1-dioxo-1,2,5-thiadiazolidin-3-one;
5-(5-Methyl-2-nitro-benzyl)-1,1-dioxo-1,2,5-thiadiazolidin-3-one;
5-(2-Amino-benzyl)-1,1-dioxo-1,2,5-thiadiazolidin-3-one;
2-[4-(1,1,4-Trioxo-1,2,5-thiadiazolidin-2-ylmethyl)-benzyl]-isoindole-1,3-dione;
2-[3-(1,1,4-Trioxo-1,2,5-thiadiazolidin-2-ylmethyl)-benzyl]-isoindole-1,3-dione;
5,5'-[1,4-Phenylenebis(methylene)bis[1,2,5-thiadiazolidine-3-one], 1,1-dioxide;
N-[2-(1,1,4-Trioxo-1,2,5-thiadiazolidin-2-ylmethyl)-phenyl]-oxalamic acid;
5-(3-Hydroxy-benzyl)-1,1-dioxo-1,2,5-thiadiazolidin-3-one;
2-Amino-4-(1,1,4-trioxo-1,2,5-thiadiazolidin-2-ylmethyl)-benzoic acid;
5-[5-(4-Nitro-phenyl)-furan-2-ylmethyl]-1,1-dioxo-1,2,5-thiadiazolidin-3-one;
5-(4-Fluoro-2-trifluoromethyl-benzyl)-1,1-dioxo-1,2,5-thiadiazolidin-3-one;
5-(3-Hydroxymethyl-benzyl)-1,1-dioxo-1,2,5-thiadiazolidin-3-one;
5-(3-Amino-5-hydroxymethyl-benzyl)-1,1-dioxo-1,2,5-thiadiazolidin-3-one;
5-(3-Amino-4-methyl-benzyl)-1,1-dioxo-1,2,5-thiadiazolidin-3-one;
5-(2-Amino-3-methyl-benzyl)-1,1-dioxo-1,2,5-thiadiazolidin-3-one;
5-(3-Amino-2-methyl-benzyl)-1,1-dioxo-1,2,5-thiadiazolidin-3-one;
5-(2-Amino-5-methyl-benzyl)-1,1-dioxo-1,2,5-thiadiazolidin-3-one;
2,2,2-Trifluoro-N-[4-(1,1,4-trioxo-1,2,5-thiadiazolidin-2-ylmethyl)-benzyl]-acetamide;
5-(3,4-Dimethoxy-benzyl)-1,1-dioxo-1,2,5-thiadiazolidin-3-one;
5-(3-Amino-5-hydroxy-benzyl)-1,1-dioxo-1,2,5-thiadiazolidin-3-one;
5-(3,5-Dimethyl-benzyl)-1,1-dioxo-1,2,5-thiadiazolidin-3-one;
(S)-3-Phenyl-2-[3-(1,1,4-trioxo-1,2,5-thiadiazolidin-2-ylmethyl)-benzylamino]-propionic acid ethyl ester;
(S)-3-Phenyl-2-[4-(1,1,4-trioxo-1,2,5-thiadiazolidin-2-ylmethyl)-benzylamino]-propionic acid ethyl ester;
2-Amino-5-(1,1,4-trioxo-1,2,5-thiadiazolidin-2-ylmethyl)-benzoic acid methyl ester;
2-Acetylamino-4-(1,1,4-trioxo-1,2,5-thiadiazolidin-2-ylmethyl)-benzoic acid methyl ester;
5-(2-Benzyl-benzyl)-1,1-dioxo-1,2,5-thiadiazolidin-3-one;
5-(2,4-Bis-trifluoromethyl-benzyl)-1,1-dioxo-1,2,5-thiadiazolidin-3-one;
1,1-Dioxo-5-(2,4,6-trifluoro-benzyl)-1,2,5-thiadiazolidin-3-one;
5-(2-Bromo-benzyl)-1,1-dioxo-1,2,5-thiadiazolidin-3-one;
5,5'-[[1,1'-biphenyl]-2,2'-diyl]bis(methylene)bis[1,2,5-thiadiazolidine-3-one], 1,1-dioxide;
5-(4-Ethylaminomethyl-benzyl)-1,1-dioxo-1,2,5-thiadiazolidin-3-one;
2-Acetylamino-4-(1,1,4-trioxo-1,2,5-thiadiazolidin-2-ylmethyl)-benzoic acid;
2-Amino-4-(1,1,4-trioxo-1,2,5-thiadiazolidin-2-ylmethyl)-benzoic acid ethyl ester;
1,1-Dioxo-5-[4-(phenethylamino-methyl)-benzyl]-1,2,5-thiadiazolidin-3-one;
5-(4-Diethylaminomethyl-benzyl)-1,1-dioxo-1,2,5-thiadiazolidin-3-one;
2-Amino-4-(1,1,4-trioxo-1,2,5-thiadiazolidin-2-ylmethyl)-benzoic acid benzyl ester;
N-Benzyl-4-(1,1,4-trioxo-1,2,5-thiadiazolidin-2-ylmethyl)-benzamide;
5-(5-Dimethylaminomethyl-furan-2-ylmethyl)-1,1-dioxo-1,2,5-thiadiazolidin-3-one;
N-[2-(3-Trifluoromethyl-phenyl)-ethyl]-4-(1,1,4-trioxo-1,2,5-thiadiazolidin-2-ylmethyl)-benzamide;
N-(3-Methyl-butyl)-4-(1,1,4-trioxo-1,2,5-thiadiazolidin-2-ylmethyl)-benzamide;
(S)-3-Phenyl-2-(1,1,4-trioxo-1,2,5-thiadiazolidin-2-yl)-propionic acid;
(R)-3-Phenyl-2-(1,1,4-trioxo-1,2,5-thiadiazolidin-2-yl)-propionic acid;
4-(1,1,4-Trioxo-1,2,5-thiadiazolidin-2-ylmethyl)-benzoic acid benzyl ester;
[4-(1,1,4-Trioxo-1,2,5-thiadiazolidin-2-ylmethyl)-phenoxy]-acetic acid;
4-(1,1,4-Trioxo-1,2,5-thiadiazolidin-2-ylmethyl)-benzoic acid isobutyl ester;
2-Amino-4-(1,1,4-trioxo-1,2,5-thiadiazolidin-2-ylmethyl)-benzoic acid isobutyl ester;
[4-(1,1,4-Trioxo-1,2,5-thiadiazolidin-2-ylmethyl)-phenoxy]-acetic acid methyl ester;
4-(1,1,4-Trioxo-1,2,5-thiadiazolidin-2-ylmethyl)-benzoic acid 4-carboxymethoxy-benzyl ester;
4-{2-[4-(1,1,4-Trioxo-1,2,5-thiadiazolidin-2-ylmethyl)-benzylamino]-ethyl}benzoic acid;
[4-(1,1,4-Trioxo-1,2,5-thiadiazolidin-2-ylmethyl)-phenoxy]-acetic acid isobutyl ester;
[4-(1,1,4-Trioxo-1,2,5-thiadiazolidin-2-ylmethyl)-phenoxy]-acetic acid benzyl ester;
N-Isobutyl-4-(1,1,4-trioxo-1,2,5-thiadiazolidin-2-ylmethyl)-benzamide;
5-(5-Diethylaminomethyl-thiophen-2-ylmethyl)-1,1-dioxo-1,2,5-thiadiazolidin-3-one;
3-Nitro-4-(1,1,4-trioxo-1,2,5-thiadiazolidin-2-ylmethyl)-benzoic acid methyl ester;
3-Nitro-4-(1,1,4-trioxo-1,2,5-thiadiazolidin-2-ylmethyl)-benzoic acid ethyl ester;
3-Nitro-4-(1,1,4-trioxo-1,2,5-thiadiazolidin-2-ylmethyl)-benzoic acid isobutyl ester;
5-(4-Ethoxy-benzyl)-1,1-dioxo-1,2,5-thiadiazolidin-3-one;
1,1-Dioxo-5-(3-trifluoromethyl-benzyl)-1,2,5-thiadiazolidin-3-one;
4-(1,1,4-Trioxo-1,2,5-thiadiazolidin-2-ylmethyl)-benzoic acid 4-carboxymethyl-benzyl ester;
4-(1,1,4-Trioxo-1,2,5-thiadiazolidin-2-ylmethyl)-benzoic acid phenethyl ester;
4-(1,1,4-Trioxo-1,2,5-thiadiazolidin-2-ylmethyl)-benzoic acid 2-phenylamino-ethyl ester;
4-(1,1,4-Trioxo-1,2,5-thiadiazolidin-2-ylmethyl)-benzoic acid 2-(3-methoxy-phenyl)ethyl ester;

4-(1,1,4-Trioxo-1,2,5-thiadiazolidin-2-ylmethyl)-benzoic acid 4-(1,1,4-trioxo-1,2,5-thiadiazolidin-2-ylmethyl)-benzyl ester;
4-(1,1,4-Trioxo-1,2,5-thiadiazolidin-2-ylmethyl)-benzoic acid 2,2-dimethyl-propyl ester;
4-(1,1,4-Trioxo-1,2,5-thiadiazolidin-2-ylmethyl)-benzoic acid 2-methoxycarbonyl-2-methyl-propyl ester;
4-(1,1,4-Trioxo-1,2,5-thiadiazolidin-2-ylmethyl)-benzoic acid 2,2,4-trimethyl-pentyl ester;
4-(1,1,4-Trioxo-1,2,5-thiadiazolidin-2-ylmethyl)-benzoic acid 3-dimethylamino-2,2-dimethyl-propyl ester;
4-(1,1,4-Trioxo-1,2,5-thiadiazolidin-2-ylmethyl)-benzoic acid (3aR,4S,5R,6aS)-5-benzoyloxy-2-oxo-hexahydro-cyclopenta[b]furan4-ylmethyl ester;
4-(1,1,4-Trioxo-1,2,5-thiadiazolidin-2-ylmethyl)-benzoic acid 3-methyl-4-nitro-benzyl ester;
4-(1,1,4-Trioxo-1,2,5-thiadiazolidin-2-ylmethyl)-benzoic acid 3-chloro-4-methyl-benzyl ester;
4-(1,1,4-Trioxo-1,2,5-thiadiazolidin-2-ylmethyl)-benzoic acid 5-ethoxycarbonyl-pentyl ester;
4-(1,1,4-Trioxo-1,2,5-thiadiazolidin-2-ylmethyl)-benzoic acid 2-(3-chloro-phenyl)-ethyl ester;
4-(1,1,4-Trioxo-1,2,5-thiadiazolidin-2-ylmethyl)-benzoic acid 2-m-tolyl-ethyl ester;
4-(1,1,4-Trioxo-1,2,5-thiadiazolidin-2-ylmethyl)-benzoic acid 2-(3-trifluoromethyl-phenyl)-ethyl ester;
(R)-3-Phenyl-2-[4-(1,1,4-trioxo-1,2,5-thiadiazolidin-2-ylmethyl)-benzylamino]-propionic acid ethyl ester;
5-[4-(Benzylamino-methyl)-benzyl]-1,1-dioxo-1,2,5-thiadiazolidin-3-one;
4-(1,1,4-Trioxo-1,2,5-thiadiazolidin-2-ylmethyl)-benzoic acid 4-methyl-benzyl ester;
4-[(1,1,4-trioxido-1,2,5-thiadiazolidin-2-yl)methyl]-benzoic acid [4-(methoxycarbonyl)-phenyl]methyl ester;
4-(1,1,4-Trioxo-1,2,5-thiadiazolidin-2-ylmethyl)-benzoic acid 2-cyclohexyl-2-methyl-propyl ester;
4-(1,1,4-Trioxo-1,2,5-thiadiazolidin-2-ylmethyl)-benzoic acid 2-phenoxy-propyl ester;
4-(1,1,4-Trioxo-1,2,5-thiadiazolidin-2-ylmethyl)-benzoic acid 4-trifluoromethyl-benzyl ester;
4-(1,1,4-Trioxo-1,2,5-thiadiazolidin-2-ylmethyl)-benzoic acid 3-trifluoromethyl-benzyl ester;
4-[(1,1,4-trioxido-1,2,5-thiadiazolidin-2-yl)methyl]-benzoic acid 2-(4-carboxyphenyl)ethyl ester;
3-[[[4-[(1,1,4-Trioxido-1,2,5-thiadiazolidin-2-yl)methyl]benzoyl]-oxy]methyl]benzoic acid;
5-[4-(Isobutylamino-methyl)-benzyl]-1,1-dioxo-1,2,5-thiadiazolidin-3-one;
5-{4-[(2,2-Dimethyl-propylamino)-methyl]-benzyl}-1,1-dioxo-1,2,5-thiadiazolidin-3-one;
4-(1,1,4-Trioxo-1,2,5-thiadiazolidin-2-ylmethyl)-benzoic acid naphthalen-1-ylmethyl ester;
4-(1,1,4-Trioxo-1,2,5-thiadiazolidin-2-ylmethyl)-benzoic acid 4-nitro-benzyl ester;
(4-{2-[4-(1,1,4-Trioxo-1,2,5-thiadiazolidin-2-ylmethyl)-benzoylamino]-ethyl}-phenyl)-acetic acid;
4-(1,1,4-Trioxo-1,2,5-thiadiazolidin-2-ylmethyl)-benzoic acid 3-nitro-benzyl ester;
4-(1,1,4-Trioxo-1,2,5-thiadiazolidin-2-ylmethyl)-benzoic acid 3-(carboxymethyl-amino)-2,2-dimethyl-propyl ester;
5-[4-(1,1,4-Trioxo-1,2,5-thiadiazolidin-2-ylmethyl)-benzoyloxymethyl]-thiophene-2-carboxylic acid;
5-[4-(4-Benzyl-piperazin-1-ylmethyl)-benzyl]-1,1-dioxo-1,2,5-thiadiazolidin-3-one;
4-(1,1,4-Trioxo-1,2,5-thiadiazolidin-2-ylmethyl)-benzoic acid biphenyl-4-ylmethyl ester;
4-(1,1,4-Trioxo-1,2,5-thiadiazolidin-2-ylmethyl)-benzoic acid 4-acetylamino-benzyl ester;
4-(1,1,4-Trioxo-1,2,5-thiadiazolidin-2-ylmethyl)-benzoic acid 2-benzyl-benzyl ester;
4-(1,1,4-Trioxo-1,2,5-thiadiazolidin-2-ylmethyl)-benzoic acid 2-methyl-benzyl ester;
4-(1,1,4-Trioxo-1,2,5-thiadiazolidin-2-ylmethyl)-benzoic acid 2-methyl-3-nitro-benzyl ester;
Glycine, N-(aminosulfonyl)-N-[[4-[[(2-phenylethyl)thio]methyl]phenyl]methyl]-, methyl ester;
4-(1,1,4-Trioxo-1,2,5-thiadiazolidin-2-ylmethyl)-benzoic acid 3-carboxymethyl-benzyl ester;
4-(1,1,4-Trioxo-1,2,5-thiadiazolidin-2-ylmethyl)-benzoic acid 4-methyl-3-nitro-benzyl ester;
4-(1,1,4-Trioxo-1,2,5-thiadiazolidin-2-ylmethyl)-benzoic acid 4-fluoro-2-trifluoromethyl-benzyl ester;
4-[5-(2,4-Dimethoxy-benzyl)-1,1,4-trioxo-1,2,5-thiadiazolidin-2-ylmethyl]-benzoic acid 4-(1,1,4-trioxo-1,2,5-thiadiazolidin-2-yl)-benzyl ester;
4-(1,1,4-Trioxo-1,2,5-thiadiazolidin-2-ylmethyl)-benzoic acid 4-(1,1,4-trioxo-1,2,5-thiadiazolidin-2-yl)-benzyl ester;
4-(1,1,4-Trioxo-1,2,5-thiadiazolidin-2-ylmethyl)-benzoic acid 5-methyl-2-nitro-benzyl ester;
4-(1,1,4-Trioxo-1,2,5-thiadiazolidin-2-ylmethyl)-benzoic acid o-tolyl ester;
4-(1,1,4-Trioxo-1,2,5-thiadiazolidin-2-ylmethyl)-benzoic acid 3-(carboxymethyl-methyl-amino)-2,2-dimethyl-propyl ester;
4-(1,1,4-Trioxo-1,2,5-thiadiazolidin-2-ylmethyl)-benzoic acid phenyl ester 4-(1,1,4-Trioxo-1,2,5-thiadiazolidin-2-ylmethyl)-benzoic acid 5-isobutylcarbamoyl-thiophen-2-ylmethyl ester;
4-(1,1,4-Trioxo-1,2,5-thiadiazolidin-2-ylmethyl)-benzoic acid naphthalen-2-ylmethyl ester;
N,N-Diisobutyl-4-(1,1,4-trioxo-1,2,5-thiadiazolidin-2-ylmethyl)-benzamide;
{4-[4-(1,1,4-Trioxo-1,2,5-thiadiazolidin-2-ylmethyl)-benzoyl]-piperazin-1-yl}-acetic acid;
4-(1,1,4-Trioxo-1,2,5-thiadiazolidin-2-ylmethyl)-benzoic acid naphthalen-2-yl ester;
5-[4-(1,1,4-Trioxo-1,2,5-thiadiazolidin-2-ylmethyl)-benzoyloxymethyl]-thiophene-2-carboxylic acid isobutyl ester;
4-(1,1,4-Trioxo-1,2,5-thiadiazolidin-2-ylmethyl)-benzoic acid 5-carbamoyl-thiophen-2-ylmethyl ester;
5-[4-(4-Benzyl-piperazine-1-carbonyl)-benzyl]-1,1-dioxo-1,2,5-thiadiazolidin-3-one;
4-(1,1,4-Trioxo-1,2,5-thiadiazolidin-2-ylmethyl)-benzoic acid 5-(3-phenyl-propionyl)-thiophen-2-ylmethyl ester;
4-(1,1,4-Trioxo-1,2,5-thiadiazolidin-2-ylmethyl)-benzoic acid 5-benzylcarbamoyl-thiophen-2-ylmethyl ester;
1,1-Dioxo-5-phenyl-1,2,5-thiadiazolidin-3-one;
5-(2,4-Diamino-phenyl)-1,1-dioxo-1,2,5-thiadiazolidin-3-one;
3-(1,1,4-Trioxo-1,2,5-thiadiazolidin-2-yl)-benzoic acid methyl ester;
3-(1,1,4-Trioxo-1,2,5-thiadiazolidin-2-yl)-benzoic acid;
5-(4-Aminomethyl-phenyl)-1,1-dioxo-1,2,5-thiadiazolidin-3-one;
[2-(1,1,4-Trioxo-1,2,5-thiadiazolidin-2-yl)-phenyl]-acetic acid methyl ester;
[2-(1,1,4-Trioxo-1,2,5-thiadiazolidin-2-yl)-phenyl]-acetic acid;
5-(2,4-Dimethoxyphenyl)-1,1-dioxo-[1,2,5]thiadiazolidin-3-one potassium salt;

N-Benzyl-2-[3-methyl-4-(1,1,4-trioxo-[1,2,5]thiadiazolidin-2-yl)-phenoxy]-acetamide;

3-[3-Hydroxy-4-(1,1,4-trioxo-[1,2,5]thiadiazolidin-2-yl)-benzyl]-3,4-dihydro-1H-benzo[1,4]diazepine-2,5-dione;

5-(4-Iodo-phenyl)-1,1-dioxo-1,2,5-thiadiazolidin-3-one;

(S)-2-Amino-3-[4-(1,1,4-trioxo-1,2,5-thiadiazolidin-2-yl)-phenyl]-propionic acid benzyl ester;

(S)-2-Amino-3-[4-(1,1,4-trioxo-1,2,5-thiadiazolidin-2-yl)-phenyl]-propionic acid;

(S)-2-Acetylamino-N{(S)-1-pentylcarbamoyl-2-[4-(1,1,4-trioxo-1,2,5-thiadiazolidin-2-yl)-phenyl]-ethyl}-3-phenyl-propionamide;

(S)-2-Acetylamino-3-phenyl-N-{(S)-1-(4-phenyl-butylcarbamoyl-2-[4-(1,1,4-trioxo-1,2,5-thiadiazolidin-2-yl)-phenyl]-ethyl}propionamide;

[4-(2-{(S)-2-((S)-2-Acetylamino-3-phenyl-propionylamino)-3-[4-(1,1,4-trioxo-1,2,5-thiadiazolidin-2-yl)-phenyl]-propionylamino}-ethyl)-phenyl]-acetic acid;

2-[4-(2-Benzoylamino-2-{1-carbamoyl-2-[4-(1,1,4-trioxo-1,2,5-thiadiazolidin-2-yl)-phenyl]-ethylcarbamoyl}-ethyl)-phenoxy]-malonic acid;

(S)-2-(Biphenyl-4-sulfonylamino)-N-pentyl-3-[4-(1,1,4-trioxo-1,2,5-thiadiazolidin-2-yl)-phenyl]-propionamide;

(S)-2-(Biphenyl-4-sulfonylamino)-N-(4-phenyl-butyl)-3-[4-(1,1,4-trioxo-1,2,5-thiadiazolidin-2-yl)-phenyl]-propionamide;

(S)-2-Benzenesulfonylamino-N-pentyl-3-[4-(1,1,4-trioxo-1,2,5-thiadiazolidin-2-yl)-phenyl]-propionamide;

(S)-2-Benzenesulfonylamino-N-(4-phenyl-butyl)-3-[4-(1,1,4-trioxo-1,2,5-thiadiazolidin-2-yl)-phenyl]-propionamide;

(S)-2-Benzenesulfonylamino-N-(3,3-diphenyl-propyl-3-[4-(1,1,4-trioxo-1,2,5-thiadiazolidin-2-yl)-phenyl]-propionamide;

(S)-2-Acetylamino-N-[(S)-2-[3-bromo-4-(1,1,4-trioxo-1,2,5-thiadiazolidin-2-yl)-phenyl]-1-(4-phenyl-butylcarbamoyly)-ethyl]-3-phenyl-propionamide;

(S)-2-Benzenesulfonylamino-3-[3-bromo-4-(1,1,4-trioxo-1,2,5-thiadiazolidin-2-yl)-phenyl]-N-(4-phenyl-butyl)-propionamide;

(S)-2-((S)-2-Acetylamino-3-phenyl-propionylamino)-3-[3-bromo-4-(1,1,4-trioxo-1,2,5-thiadiazolidin-2-yl)-phenyl]-N-pentyl-propionamide; and (S)-2-Acetylamino-N{(S)-1-pentylcarbamoyl-2-[3-(1,1,4-trioxo-1,2,5-thiadiazolidin-2-yl)-phenyl]-ethyl}-3-phenyl-propionamide;

or a pharmaceutically acceptable salt thereof; or a prodrug derivative thereof.

16. A pharmaceutical composition, comprising:
a therapeutically effective amount of a compound of claim 1 in combination with one or more pharmaceutically acceptable carriers.

* * * * *